(12) United States Patent
Klaus et al.

(10) Patent No.: US 10,882,827 B2
(45) Date of Patent: Jan. 5, 2021

(54) ENHANCED ERYTHROPOIESIS AND IRON METABOLISM

(71) Applicant: FibroGen, Inc., San Francisco, CA (US)

(72) Inventors: Stephen J Klaus, Boston, MA (US); Christopher J Molineaux, San Francisco, CA (US); Thomas B Neff, Atherton, CA (US); Volkmar Guenzler-Pukall, Marburg (DE); Robert C Stephenson, Foster City, CA (US); Todd W Seeley, Moraga, CA (US); Ingrid Langsetmo Parobok, Fremont, CA (US)

(73) Assignee: FIBROGEN, INC., San Francisco, CA (US)

(*) Notice: Subject to any disclaimer, the term of this patent is extended or adjusted under 35 U.S.C. 154(b) by 275 days.

(21) Appl. No.: 15/882,772

(22) Filed: Jan. 29, 2018

(65) Prior Publication Data

US 2018/0162819 A1 Jun. 14, 2018

Related U.S. Application Data

(60) Continuation of application No. 14/084,443, filed on Nov. 19, 2013, now Pat. No. 9,920,011, which is a division of application No. 10/861,590, filed on Jun. 3, 2004, now Pat. No. 8,614,204.

(60) Provisional application No. 60/569,797, filed on May 10, 2004, provisional application No. 60/566,488, filed on Apr. 29, 2004, provisional application No. 60/566,237, filed on Apr. 29, 2004, provisional application No. 60/476,704, filed on Jun. 6, 2003.

(51) Int. Cl.
| | |
|---|---|
| C07D 217/24 | (2006.01) |
| A61K 31/00 | (2006.01) |
| A61K 31/165 | (2006.01) |
| A61K 31/395 | (2006.01) |
| C07C 275/40 | (2006.01) |
| A61K 31/472 | (2006.01) |
| A61K 31/17 | (2006.01) |

(52) U.S. Cl.
CPC ............ *C07D 217/24* (2013.01); *A61K 31/00* (2013.01); *A61K 31/165* (2013.01); *A61K 31/17* (2013.01); *A61K 31/395* (2013.01); *A61K 31/472* (2013.01); *C07C 275/40* (2013.01)

(58) Field of Classification Search
None
See application file for complete search history.

(56) References Cited

U.S. PATENT DOCUMENTS

| | | | |
|---|---|---|---|
| 4,732,889 A * | 3/1988 | Cynshi | C07K 14/505 514/13.5 |
| 5,607,954 A | 3/1997 | Weidmann et al. | |
| 5,610,172 A | 3/1997 | Weidmann et al. | |
| 5,620,995 A | 4/1997 | Weidmann et al. | |
| 5,620,996 A | 4/1997 | Weidmann et al. | |
| 5,658,933 A | 8/1997 | Weidmann et al. | |
| 5,719,164 A | 2/1998 | Weidmann et al. | |
| 5,726,305 A | 3/1998 | Weidmann et al. | |
| 5,942,434 A | 8/1999 | Ratcliffe et al. | |
| 5,985,913 A | 11/1999 | Williams et al. | |
| 6,020,350 A | 2/2000 | Weidmann et al. | |
| 6,093,730 A | 7/2000 | Weidmann et al. | |
| 6,124,131 A | 9/2000 | Semenza | |
| 6,432,927 B1 | 8/2002 | Gregory | |
| 6,562,799 B1 | 5/2003 | Semenza | |
| 6,855,510 B2 | 2/2005 | Kaelin | |
| 7,618,940 B2 | 11/2009 | Fourney et al. | |
| 7,696,223 B2 | 4/2010 | Deng et al. | |
| 7,713,986 B2 | 5/2010 | Seeley et al. | |
| 7,928,120 B2 | 4/2011 | Arend et al. | |
| 8,017,625 B2 | 9/2011 | Arend et al. | |
| 8,217,043 B2 | 7/2012 | Deng et al. | |
| 8,269,008 B2 | 9/2012 | Arend et al. | |
| 8,298,026 B2 | 10/2012 | Ochiai | |
| 8,318,703 B2 | 11/2012 | Klaus et al. | |
| 8,324,405 B2 | 12/2012 | Ho et al. | |
| 8,466,172 B2 | 6/2013 | Guenzler-Pukall et al. | |
| 8,604,012 B2 | 12/2013 | Klaus et al. | |
| 8,604,013 B2 | 12/2013 | Klaus et al. | |
| 8,609,646 B2 | 12/2013 | Klaus et al. | |
| 8,614,204 B2 | 12/2013 | Klaus et al. | |
| 8,629,131 B2 | 1/2014 | Klaus et al. | |

(Continued)

FOREIGN PATENT DOCUMENTS

| | | |
|---|---|---|
| DE | 10010423 A1 | 9/2001 |
| DE | 10010425 A1 | 9/2001 |

(Continued)

OTHER PUBLICATIONS

Warnecke et al. "Activation of the hypoxia-inducible factor pathway and stimulation of angiogenesis by application of prolyl hydroxylase inhibitors," The FASEB Journal published Apr. 22, 2003 (Year: 2003).*

(Continued)

*Primary Examiner* — Jeffrey S Lundgren
*Assistant Examiner* — Michael J Schmitt
(74) *Attorney, Agent, or Firm* — Troutman Pepper Hamilton Sanders LLP

(57) ABSTRACT

The present invention relates to methods and compounds for regulating or enhancing erythropoiesis and iron metabolism, and for treating or preventing iron deficiency and anemia of chronic disease.

24 Claims, 36 Drawing Sheets

(56) References Cited

U.S. PATENT DOCUMENTS

| | | | |
|---|---|---|---|
| 8,759,373 | B2 | 6/2014 | Arend et al. |
| 8,927,591 | B2 | 1/2015 | Ho et al. |
| 8,952,160 | B2 | 2/2015 | Zhou et al. |
| 9,174,974 | B2 | 11/2015 | Zhang et al. |
| 9,920,011 | B2 | 3/2018 | Klaus et al. |
| 10,626,090 | B2 | 4/2020 | Klaus et al. |
| 2003/0153503 | A1 | 8/2003 | Klaus et al. |
| 2004/0146964 | A1 | 7/2004 | Maxwell et al. |
| 2006/0199836 | A1 | 9/2006 | Turtle et al. |
| 2010/0331362 | A1 | 12/2010 | Klaus et al. |
| 2011/0166178 | A1 | 7/2011 | Klaus et al. |

FOREIGN PATENT DOCUMENTS

| | | | | |
|---|---|---|---|---|
| DE | 10010426 | A1 | 9/2001 | |
| DE | 10010430 | A1 | 9/2001 | |
| EP | 0083129 | B1 | 2/1986 | |
| EP | 0650960 | B1 | 3/1997 | |
| EP | 0650961 | B1 | 3/1997 | |
| NZ | 252738 | | 8/1996 | |
| WO | WO2000050390 | A1 | 8/2000 | |
| WO | WO2000069908 | A1 | 11/2000 | |
| WO | WO2000074725 | A1 | 12/2000 | |
| WO | 2001000598 | A1 | 1/2001 | |
| WO | 2001000601 | A1 | 1/2001 | |
| WO | 2001064652 | A1 | 9/2001 | |
| WO | WO-02074981 | A2 * | 9/2002 | ............. A61K 31/21 |
| WO | WO2002074249 | A1 | 9/2002 | |
| WO | WO2002074981 | A1 | 9/2002 | |
| WO | 2002088363 | A2 | 11/2002 | |
| WO | 2002089799 | A2 | 11/2002 | |
| WO | WO2002089809 | A1 | 11/2002 | |
| WO | WO2003049686 | A1 | 6/2003 | |
| WO | WO2003057820 | A1 | 7/2003 | |
| WO | WO2003053997 | A1 | 9/2003 | |

OTHER PUBLICATIONS

And Vreugdenhil et al. "Tumor necrosis factor alpha is associated with disease activity and the degree of anemia in patients with rheumatoid arthritis," European Journal of Clinical Investigation (1992) 22, 488-493 (Year: 1992).*
Frazer, DM et al. "Hepcidin Expression Inversely Correlates with the Expression of Duodenal Iron Transporters and Iron Absorption in Rats." Gastroenterology; vol. 123(3) Sep. 2002.
Friedman, Lisa, et al. "Prolyl 4-Hydroxylase is Required for Viability and Morphogenesis in Caenorhabditis elegans." PNAS vol. 97(9) Apr. 25, 2000.
Fuchs, D. et al. "Immune Activation and the Anaemia Associated with Chronic Inflammatory Disorders," Eur. J. Hematol. (1991) 46 1991.
Ganz, T. "Hepcidin, a Key Regulator of Iron Metabolism and Mediator of Anemia of Inflammation," Blood; vol. 102(3) Aug. 1, 2003.
Ganz, T. "The Role of Hepcidin in Iron Sequestration During Infections and in the Pathogenesis of Anemia of Chronic Disease," IMAJ 2003 vol. Nov. 4, 2002.
Genc et al. "Soluble Transferrin Receptor and Soluble Transferrin Receptor-Ferritin Index for Evaluation of the Iron Status in Elderly Patients," Tohoku J. Exp. Med. vol. 202 2004.
Giaccia, Amato, et al. "HIF-1 as a Target for Drug Development." Nature Reviews vol. 2 Oct. 2003.
Goch, J. et al., "Treatment of Erythropoietin-Resistant Anaemia with Desferrioxamine in Patients on Haemofiltration," Eur J. Hematol. 55 1995.
Goldman, L., C. Cecil, Textbook of Medicine, 21st ed. 2000.
Goswami, Tapasree, et al., "Iron Transport: Emerging Roles in Health and Disease," Biochem. Cell Biol, vol. 80 2002.
Griffiths, et al. "Intestinal iron uptake determined by divalent metal transporter is enhanced in HFE-deficient mice with hemochromatosis," Gastroenterology, vol. 120(6) May 2001.
Gubler, Clark J. et al., "The Anemia of Infection" J Biol Chem.; 184(2) Jun. 1950.
Sunshin, Hiromi, et al., "Iron-dependent Regulation of the Divalent Metal Ion Transporter," FEBS Letters 509 Nov. 21, 2001.
Gupta, "High Serum Transferrin Receptor Level in Anemia of Chronic Disorders Indicates Coexistent Iron Deficiency," American Journal of Hematology, vol. 72 2003.
Haase, Volker. "Oxygen regulates epithelial-to-mesenchymal transition: insights into molecular mechanisms and relevance to disease." Kidney Int. ;76(5):492-499 Sep. 2009.
Haile, David J., "Regulation of Genes of Iron Metabolism by the Iron-Response Proteins," Am J. Med. Sci. vol. 318(4) Oct. 1999.
Hanson, Eric S. et al., "Hypoxia Post-translationally Activates Iron-regulatory Protein 2," J. Biol. Chem. vol. 274(8) Feb. 19, 1999.
Harris, A.L., "Hypoxia—a key regulatory factor in tumour growth." Nat Rev Cancer.2(1) Jan. 2002.
Harris, et al. "Targeted gene disruption reveals an essential role for ceruloplasmin in cellular iron efflux." Proc Natl Acad Sci U S A.;vol. 96(19) Sep. 14, 1999.
Heikkinen, J et al., "Lysyl Hydroxylase 3 Is a Multifunctional Protein Possessing Collagen Glucosyltransferase Activity", J Biol. Chem.; vol. 275(46) Nov. 17, 2000.
Heinecke,K. et al., "The Cellular Answer to Oxygen Deficiency," German J. Sports Med.; vol. 53(10) 2002.
Hirsila, Maija, et al. "Characterization of the Human Prolyl 4-Hydroxylases that Modify the Hypoxia-Inducible Factor," J. Biol. Chem. vol. 278(33) Aug. 15, 2003.
Hofer, T. et al. "Oxygen Sensing, HIF-lalpha Stabilization and Potential Therapeutic Strategies," Eur. J. Physiol. 443 2002.
Hofer et al. "Hypoxic up-regulation of erythroid 5-aminolevulinate synthase." Blood.; vol. 101(1) Jan. 1, 2003.
Huang, et al."Regulation of hypoxia-inducible factor lalpha is mediated by an O2-dependent degradation domain via the ubiquitin-proteasome pathway"PNAS; vol. 95(14) Jul. 7, 1998.
Huebers, et al. "The physiology of transferrin and transferrin receptors." Physiol Reviews; vol. 67(2) Apr. 1987.
Humes, H. David, "Kelley's Essentials of Internal Medicine" Lippincott, Williams & Wilkins 2001.
Gafter-Gvili, et al. "Non-transferrin-bound serum iron (NTBI) in megaloblastic anemia: effect of vitamin B(12) treatment." Hematol J.; 5(1) 2004.
Imagawa, Shigehiko, et al. "Basics of Erythropoietin," Mole. Cytological Treatment 1(6) 2000.
Ivan, Mircea, et al., "HIF alpha Targeted for VHL-Mediated Destruction by Proline Hydroxylation: Implications for O2 Sensing," Science; vol. 292 Apr. 20, 2001.
Ivan, Mircea, et al., "Biochemical Purification and Pharmacological Inhibition of a Mammalian Prolyl Hydroxylase . . . " PNAS; vol. 99(21) Oct. 15, 2002.
Jaakola, Panu, et al., "Targeting of HIF-alpha to the von Hippel-Lindau Ubiquitylation Complex by O2-regulated Prolyl Hydroxylation," Science vol. 292 Apr. 20, 2001.
Jandl et al. "The plasma-to-cell cycle of transferrin." J Clin Invest.; vol. 42(3) Mar. 1963.
Jelkmann, Wolfgang B., et al., "Inhibition of Erythropoietin Production by Cytokines," Annals NY Acad. Sci.; 718 1991.
Jia, Steve, et al., "A Fully Active Catalytic Domain of Vobine Aspartyl (Asparaginyl) Beta-Hydroxylase Expressed in *Escherichia Coli*. . . " PNAS USA vol. 91(15) Jul. 1994.
Kaule, Gunhild and Gunzler, Volkmar, "Assay for 2-Oxoglutarate Decarboxylating Enzymes Based on the Determination of [1-14C] Succinate: Application to Prolyl 4-Hydroxylase" Analytical Biochem. 184 1990.
Kivirikko, Kari I. and Myllyharju, Johanna, "Prolyl 4-Hydroxylases and Their Protein Disulfide Isomerase Subunit," Matrix Biol. vol. 16 1997.
Klaus et al. "Induction of erythropoiesis in rodents by novel and distinct families of orally active HIF prolyl hydroxylase Inhibitors", Poster 301, Keystone Conference Jan. 2008.
Klausner, Richard D., et al., "Regulating the Fate of mRNA: The Control of Cellular Iron Metabolism," Cell; vol. 72 Jan. 15, 1993.
Krause, et al., "LEAP-1, a novel highly disulfide-bonded human peptide, exhibits antimicrobial activity," FEBS Letters; 480 2000.

(56) References Cited

OTHER PUBLICATIONS

Laftah, Ah et al. "Effect of hepcidin on intestinal iron absorption in mice." Blood.; vol. 103(10) May 15, 2004.
Lee, et al. "The human Nramp2 gene: characterization of the gene structure, alternative splicing, promoter region and polymorphisms." Blood Cells Mol Dis.; 24(9) May 15, 1998.
Little, D.R. "Ambulatory Management of Common Forms of Anemia," American Family Physician; 59(6) Mar. 1999.
Lok, et al. "Identification of a hypoxia response element in the transferrin receptor gene", J.Biol.Chem.; vol. 274(34) Aug. 20, 1999.
Looker AC, et al. "Prevalence of iron deficiency in the United States." JAMA.; vol. 277(12) Mar. 26, 1997.
MacDougall, I et al., "Poor response to treatment of renal anaemia with erythropoietin corrected by iron given intravenously," Br. Med. J., vol. 299 Jul. 15, 1989.
MacDougall, Lain C. and Cooper, Angela C., "Erythropoietin Resistance: The Role of Inflammation . . . ," Nephrol. Dial. Trans.; 17(11) 2002.
Majamaa, Kari, et al., "The 2-Oxoglutarate Binding Site of Prolyl 4-Hydroxylase," Eur. J. Biochem. 138 1984.
Majamaa, Kari et al., "Differences Between Collagen Hydroxylases and 2-Oxoglutarate Dehydrogenases in their inhibition by structural analogues of 2-oxoglutarate," Biochem. J.; 229 1985.
Masson et al., "HIF prolyl and asparaginyl hydroxylases in the biological response to intracellular O2 levels," Journal of Cell Science, 116(15) 2003.
Semenza, Gregg L., "Perspectives on Oxygen Sensing," Cell, vol. 98 Aug. 6, 1999.
Semenza, Gregg L., Hypoxia-inducible factor 1: master regulator of O2 homeostasis, Current Opinion in Genetics & Development, 8 1998.
Sogowa, Kazuhiro, "Transcriptional regulatory mechanism by the transcription factor, hypoxia-inducible factor 1 . . . " Japanese J. Thrombosis and Hemastasis; 9(6) 1998.
Sorond, et al."Ironing-out mechanisms of neuronal injury under hypoxic-ischemic conditions and potential role of iron chelators as . . . " Antioxid Redox Signal. vol. 2(3) 2000.
Strohmeyer et al. "Effects of Hypdxia on Iron Absorption and Mobilization in the Rat." Am J Physiol.; 207 Jul. 1964.
Sulkowski, M. "Anemia in the treatment of hepatitis C virus infection." Clin Infect Dis.; 37 Suppl 4 2003.
Taylor, Martin S., "Characterization and comparative analysis of the EGLN gene family" Gene 275(1) 2001.
Testa, Ugo. "Recent developments in the understanding of iron metabolism." Hematol J. 2002;3(2) 2002.
Thornburg, Lora D., et al. "A non-heme iron protein with heme tendencies: An investigation of the substrate specificityof thymine hydroxlase," Biochem.; vol. 32(50) 1993.
Tran, Tanya, et al., "Dietary iron status has little effect on expression of ceruloplasmin but alters that of ferritin in rats," J. Nutr.; 132 2002.
Vannucchi, A.M., et al., "Inhibition of erythropoietin production in vitro by human interferon gamma," Br.J. Haematol; 87 1994.
Vassar, et al. "Effects of hypoxia on iron absorption in rats." Proc Soc Exp Biol Med.; 93(3) Dec. 1956.
Vreugdenhil et al. "Iron chelators may enhance erythropoiesis by increasing iron delivery to haematopoietic issue . . . ," Acta Haematologica, 89 (2) 1993.
Vreugdenhil et al., "Iron stores and serum transferrin receptor levels during recombinant human erythropoietin treatment of anemia in rheumatoid arthritis," Ann. Hematol. vol. 65 1992.
Vulpe, et al. "Hephaestin, a ceruloplasmin homologue implicated in intestinal iron transport, is defective in the sla mouse." Nat Genet.; vol. 21(2) Feb. 1999.
Wang et al., "General involvement of hypoxia—inducible factor 1 in transcriptional response to hypoxia," Proc. Natl. Acad. Sci. USA; vol. 90 May 1993.

Wang, Guang L. and Semenza, Gregg L., "Desferrioxamine induces erythropoietin gene expression and hypoxia-inducible factor 1 DNA-binding . . . ," Blood; vol. 82(12) Dec. 15, 1993.
Wanner, et al. "Epolones induce erythropoietin expression via hypoxia-inducible factor-1 alpha activation." Blood.; vol. 96(4) Aug. 15, 2000.
Warnecke, C. et al. "Activation of the hypoxia-inducible factor-pathway . . . ," FASEB J.; vol. 17(9) (Epub Apr. 22, 2003) Jun. 2003.
Weinstein et al., "Inappropriate expression of hepcidin is associated with iron refractory anemia: implications for the anemia of chronic disease," Blood; vol. 100(10) (Epub Jun. 28, 2002) Nov. 15, 2002.
Werning, "Medizin für Apotheker" Deutchland: Wissenschaftliche Verlagsgesellschaft mbH Stuttgart 1987.
Wick, M, "Iron Metabolism, Anemias Diagnosis and Therapy: Novel Concepts for Renal Anemias and Rheumatoid Arthritis," Springer Wien 2000, 4th Ed 2000.
Wick, M, "Clinical Aspects and Laboratory. Iron Metabolism, Anemias. Novel concepts in the anemias of malignancies and renal and rheumatoid diseases" Springer-Verlag 2003 5th Ed 2003.
Wiesener, et al. "HIF and oxygen sensing:as important to life as the air we breathe?" Ann.Med.; 35 2003.
Woo, Kyung Jin, et al., "Desferrioxamine, an iron chelator, enhances HIF-1alpha accumulation via cyclooxygenase-2 signaling pathway," Biochem. Biophys. res. Comm. 343 2006.
Yamanishi, et al. "Total iron-binding capacity calculated from serum transferrin concetration or serum iron concentration . . . " Clin Chem. 49(1) 2003.
Yin, Xiaohong and Dailey, Harry A., "Erythroid 5-aminolevulinate synthase is required for erythroids . . . ," Blood Cells, Molecules and Diseases; 24(3) Feb. 15, 1998.
Opposition Decision in EP 2322153 2017.
Masuda, Seiji and Sasaki, Ryuzo, "Regulation of Erythropoietin Gene Expression; Oxygen-Dependent Gene Regulation," Bio Clinica vol. 13(13) 1998.
Mccarty MF, "Hyperinsulinemia May Boost Both Hematocrit and Iron Absorption by up-regulating Activity of Hypoxia-inducible factor-1alpha." Med Hypotheses. Nov.-Dec. 2003; 61(5-6 2003.
Mckie, et al. "A novel duodenal iron-regulated transporter, IREG1, implicated in the basolateral transfer of iron to the circulation." Mol Cell; vol. 5(2) Feb. 2000.
Mckie, Andrew T., et al., "An Iron-Regulated Ferric Reductase Associated with the Absorption of Dietary Iron," Science; vol. 291 Mar. 2, 2001.
Means, Robert T., Jr., "Pathogeneis of the Anemia of Chronic Diseas: A Cytokine-mediated Anemia," Stem Cells; 13 1995.
Means, Robert T., Jr., "Advances in the Anemia of Chronic Disease," Int. J. Hematol.; 70 1999.
Means, Robert T., Jr. "Recent Developments in the Anemia of Chronic Disease," Curr. Hematol. Reports; 2 2003.
Medicines Compendium; ABPI 2004.
MedLine Plus "Total iron binding capacity: MedLine Plus Medical Encyclopedia" Feb. 24, 2014.
Mendel, G. "Studies on iron absorption. I. The relationships between the rate of erythropoiesis, hypoxia and iron absorption."Blood.;Dec. 18, 1961.
Menon,et al. "Treatment of posttransplantation recurrence of hepatitis C with interferon and ribavirin:lessons on tolerability and efficacy." Liver Transpl.; vol. 8(7) Jul. 2002.
Michal, Gerhard. "Biochemical Pathways" Berlin: Spektrum Akad. Verl., Figs. 3.8-2, 3.8-3 1999.
Mole, David R. et al. "2-oxoglutarate analogue inhibitors of HIF prolyl hydroxylase." Bioorg Med Chem Lett.; 13(16) Aug. 18, 2003.
Muir A, et al. "Regional specificity of iron uptake by small intestinal brush-border membranes from normal and iron—deficient mice." Am J Physiol.; 248(3 Pt 1): Mar. 1985.
Myllyharju, J., et al. "Characterization of the Iron- and 2-Oxoglutarate-binding sites of human prolyl 4-Hyroxylase," EMBO J; vol. 16(6) 1997.
Myllyharju, Johanna. "HIF prolyl 4-hydroxylases and their potential as drug targets." Curr Pharm Design; vol. 15 (33) 2009.
Nemeth, et al. "Hepcidin, a putative mediator of anemia of inflammation, is a type II acute-phase protein." Blood.; vol. 101(7) Apr. 1, 2003.

(56) References Cited

OTHER PUBLICATIONS

Nemeth, et al. "IL-6 mediates hypoferremia of inflammation by inducing the synthesis of the iron regulatory hormone hepcidin." J Clin Invest.; vol. 113(9) May 2004.

Nguyen LK et al. "A dynamic model of the hypoxia-inducible factor 1α (HIF-1α) network." J Cell Sci.;126(Pt 6) Mar. 15, 2013.

Nicolas, et al. "Hepcidin, a new iron regulatory peptide," Blood Cells Mol Dis. Nov.-Dec. 2002; 29(3) 2002.

Nicolas et al., "Lack of hepcidin gene expression and severe tissue Exhibit List, p. 3 iron overload in upstream stimulatory factor 2 (USF2) knockout mice," PNAS, vol. 98(15) Jul. 17, 2001.

Nicolas et al., "Severe iron deficiency anemia in transgenic mice expressing liver hepcidin," Proc. Natl. Acad. Sci. USA., vol. 99(7) Apr. 2, 2002.

Nicholas, G. et al. "The gene encoding the iron regulatory peptide hepcidin is regulated by anemia, hypoxia . . . " J. Clin. Invest.; vol. 110(7) Oct. 2002.

Oldenburg, B., et al. "Iron and inflammatory bowel disease." Aliment Phamiacol. Ther. ,15 2001.

Opposition Brief from EP 1633333, filed May 20, 2015 by Akebia Therapeutics 2015.

Opposition Decision in EP1633333 2017.

Opposition Brief from EP 2322153, filed Jul. 8, 2015 by Bayer Intellectual Property GMBH, et al. 2015.

Opposition Brief from EP 2322153, filed Jul. 6, 2015 by Akebia Therapeutics 2015.

Opposition Brief from EP 2322153, filed Jul. 6, 2015 by GlaxoGroup LTD 2015.

Opposition Brief from EP 2322155, filed May 13, 2015 by Bayer 2015.

Opposition Decision in EP 2322155 2017.

Palmerini, C.A., et al., "High-performance liquid chromatographic analysis of free hydroxyproline and proline in blood plasma and of free peptide-bound in hydroxyproline urine" J. Chromatog.; vol. 339 1985.

Park, et al., "Hepcidin, a urinary antimicrobial peptide synthesized in the liver" The Journal of Biological Chemistry, Exhibit List, p. 4; vol. 276(11) Mar. 16, 2001.

Peeters et al., "Effect of recombinant human erythropoietin on anaemia and disease activity in patients with rheumatoid arthritis and anaemia of chronic disease: a randomized placebo controlled double blind 52 weeks clinical trial," Ann Rheum Dis; vol. 55 1996.

Pigeon, et al. "Genes: Structure and regulation." A new mouse liver-specific gene, encoding a protein homologous to human antimicrobial peptide hepcidin, is overexpressed during iron overload, J. Biol. Chem.; vol. 276(11) Mar. 16, 2001.

Pugh CW, Ratcliffe PJ. "Regulation of angiogenesis by hypoxia: role of the HIF system." Nat Med.; vol. 9(6) Jun. 2003.

Punnonen et al., "Serum Transferrin Receptor and Its Ratio to Serum Ferritin in the Diagnosis of Iron Deficiency," Blood; vol. 89(3) Feb. 1, 1997.

Raja et al., "In vivo studies on the relationship between intestinal iron (Fe3+) absorption, hypoxia and erythropoiesis in the mouse," British J. Haematology, 68 1988.

Ren, Xiaohui, et al., "Effects of Desferrioxamine on Serum Erythropoietin and Veltilagtory Sensitvity to Hypoxia in Humans," J. Appl. Physiol; vol. 89 2000.

Roodman, G.D., et al., "Tumor Necrosis Factor alpha and the Anemia of Chronic Disease: Effect of Chronic Exposure . . . ," Adv. Exp. Med. Bioil.; vol. 271 1989.

Roy, et al. "The molecular biology of the anemia of chronic disease: a hypothesis." Pediatr Res.; vol. 53(3) Mar. 3, 2003.

Ratcliffe, P.J., "From erythropoietin to oxygen: hypoxia-inducible factor hydroxylases and the hypoxia signal pathway." Blood Purif.; vol. 20(5) 2002.

Salvarani, C et al., "Effects of Desferrioxamine Therapy on Chronic Disease Anemia Associated with Rheumatoid Arthritis," Rheumatol. Int.; vol. 16 1996.

Schuster, SJ et al. "Stimulation of erythropoietin gene transcription during hypoxia and cobalt exposure." Blood; vol. 73(1) Jan. 1989.

Schwartz et al., "The effects of recombinant human erythropoietin on mean corpuscular volume in patients with the anemia of chronic renal failure," Clin Nephrol.; vol. 43(4) Apr. 1995.

Semenza and Wang, "A Nuclear Factor Induced by Hypoxia via De Novo Protein Synthesis Binds to the Human Erythropoietin Gene Enhancer at a Site Required for Transcriptional Activation," Mol Cell Biol.; vol. 12(12: Dec. 1992.

Semenza, Gregg L., "Oxygen-Regulated Erythropoietin Gene Expression" in Zon, Hematopoiesis: A developmental approach, Oxford University Press, Chap. 25 2001.

Semenza, Gregg L., "HIF-1 and human disease: one highly involved factor." Genes & Dev.; Jul. 14, 2000.

Semenza, Gregg L., "HIF-1, O2, and the 3 PHDs: How Animal Cells Signal Hypoxia to the Nucleus." Cell; vol. 107 Oct. 5, 2001.

Semenza, Gregg L., "Hypoxia-inducible factor 1: oxygen homeostasis and disease pathophysiology," Trends Mole. Med; vol. 7(8) Aug. 2001.

Abboud, et al., "A novel mammalian iron-regulated protein involved in intracellular iron metabolism.,", J Biol Chem. Jun. 30, 2000;275(26): 19906-12 Jun. 30, 2000.

Adamson, J.W., "Regulation of Red Blood Cell Production," Am. J. Med., vol. 101, (suppl. 2A) Aug. 26, 1996.

Anderson, J., "Pathophysiology of Anemia of Malignancy," in Wingard, et al. Clinical Applications of Cytokines and Growth Factors, Kluwer Academic Publishers 1999.

Andrews PA. "Disorders of iron metabolism.," N Engl J Med. ;342(17):1293 Apr. 27, 2000.

Annex O22 filed as D1 with Opposition Brief filed in EP10182249.2 by Opponent Akebia Therapeutics May 13, 2015.

Anonymous. Centers for Disease Control and Prevention, "Iron Deficiency—United States 1999-2000," MMWR vol. 51 No. 40 Oct. 11, 2002.

Aravind, L. and Koonin, E.V., "The DNA Repair Protein AlkB, EGLN-9 and Leprecan Define New Families of 2-Oxoglutarate- and Iron-dependent Dioxygenases," Genome Biol. vol. 2(3) Feb. 19, 2001.

Arndt, U., et al., "Correction of Iron-deficient Erythropoiesis in the Treatment of Anemia of Chronic Disease with Recombinant Human Erythropoietin," Ann. Hematol. (2005) 84:159-166 2005.

Aucella, Filippo, et al., "Synergistic Effect of Desferrioxamine and Recombinant Erythropoietin on Erythroid Precursor Proliferation in Chronic Renal Failure," Nephrol. Dial. Trans. (1999) 14:1171-1175 1999.

Ausman DC. "Cobalt-Iron Therapy for Iron-Deficiency Anemia." J Am Geriatr Soc.; vol. 13 May 1965.

Beard, John L. "Does Iron Deficiency Cause Low Birth Weight, Prematurity, Anemia, and Mortality in Early Infancy?" Nestle Nutrition Workshop Series, vol. 52 2003.

Beutler, "Production and Destruction of Erythrocytes,". in Williams, Hematology McGraw-Hill, Ed. 6th Chapter 29 2001.

Bianchi L, et al."HIF-1-mediated activation of transferrin receptor gene transcription by iron chelation," Nucleic Acids Res.; vol. 27(21) Nov. 1, 1999.

Bickel, Martin, et al. "Selective Inhibition of Hepatic Collagen Accumulation in Experimental Liver Fibrosis in Rats by a New Prolyl 4-Hydroxylase Inhibitor," Hepatol. (1998) vol. 28(2) 1998.

Bonneau et al. "Bilateral cataract and high serum ferritin; a new genetic disorder." J Med Genet 1995, vol. 32 Oct. 1995.

Bottomley, Sylvia S. and Muller-Eberhard, Ursula, "Pathophysiology of Heme Synthesis," Seminars in Hematol. vol. 25(4) Oct. 1988.

Bowie EA, Hurley PJ. "Cobalt chloride in the treatment of refractory anaemia in patients undergoing long-term haemodialysis,"Aust N Z J Med.; vol. 5(4) Aug. 1975.

Brenda, "Enzyme reaction database excerpt" Host: BRENDA—The Comprehensive Enzyme Information System (www.brenda-enzymes. org), 3 pages 2015.

British National Formulary 45; "Iron overload" 2003.

Brown RG. "Determining the cause of anemia. General approach, with emphasis on microcytic hypochromic anemias," Postgrad Med. May 1, 1991;89(6) May 1, 1991.

Brugnara. "Iron Deficiency and Erythropoiesis: New Diagnostic Approaches," Clinical Chemistry, 49(10) 2003.

(56) References Cited

OTHER PUBLICATIONS

Bruick, Richard K. and McKnight, Steven L., "A Conserved Family of Prolyl-4-Hydroxylases that Modify HIF," Science vol. 294 Nov. 9, 2001.
Canonne-Hergaux F. et al. "Cellular and Subcellular Localization of the Nramp2 Iron Transporter in the Intestinal Brush Border and Regulation by Dietary Iron," Blood vol. 93(12) Jun. 15, 1999.
Canonne-Hergaux F. et al. "Expression of the DMT1 (NRAMP2/DCT1) Iron Transporter in Mice with Genetic Iron Overload Disorders." Blood.; vol. 97(4) Feb. 15, 2001.
Cantrill, et al. "Iron absorption from the intestinal tract. The influence of the haemoglobin concentration and of hypoxia." Aust J Exp Biol Med Sci. vol. 40 Feb. 1962.
Cavill, et al. "Correspondence: Functional Iron Deficiency." Blood Au. vol. 82(4) Aug. 15, 1993.
Chung, et al. "Molecular mechanisms and regulation of iron transport." Crit Rev Clin Lab Sci.; vol. 40(2) Apr. 2003.
Clibon, Unamarie, et al., "Erythropoietin Fails to to Reverse the Anemia in Mice Continuously Exposed to Tumor Necrosis Factor-alpha in vivo," Exp. Hematol., 18 1990.
Coles, B.L. "The use of cobalt in some common anaemias of childhood," Arch Dis Child.; 30(150) Apr. 1955.
Coles, B.L. et al., "The effect of cobalt and iron salts on the anaemia of prematurity." Arch Dis Child.; 29(144) Apr. 1954.
Communication from the Applicant Jan. 13, 2014 for EP Application 10182249.2 Jan. 13, 2014.
Cotter, S., Quick Look Series in Veterinary Medicine: Hematology. Teton New Media Jun. 2001.
Cullis, J. "Anaemia of chronic disease," Clin. Med. 2013, vol. 13 (2) 2013.
Cunliffe, C. Jane, et al., "Assay of Prolyl 4-Hydroxylase by the Chromatographic Determination of [14C]succinic Acid on Ion-exchange Minicolumns," Biochem. J. vol. 240 1986.
Cunliffe, C. Jane, et al., "Novel Inhibitors of Prolyl 4-hydroxylase 31 Inhibition by the Substrate Analogue . . . ," J. Med. Chem.; vol. 35(14) 1992.
Donovan, et al. "Positional cloning of zebrafish ferroportin 1 identifies a conserved vertebrate iron exporter." Nature.; vol. 403 (6771) Feb. 17, 2000.
Edwards MS, et al "Use of cobaltous chloride in anaemia of maintenance hemodialysis patients," Lancet.; 2(7724) Sep. 11, 1971.
Epstein, Andrew C.R., et al. "C Elegans EGL-9 and Mammalian Homologs Define a Family of Dioxygenases that Regulate HIF by Prolyl Hydroxylation, "Cell vol. 107 Oct. 5, 2001.
Erslev, Allen. "Anemia of Chronic Disease," in Williams, Hematology, McGraw-Hill, 2001, Ed. 6th 2001.
Eschbach et al., "Recombinant Human Erythropoietin in Anemic Patients with End-Stage Renal Disease", Annals of Internal Medicine, vol. 111(12) Dec. 15, 1989.
Eschbach, et al. "Correction of the Anemia of End Stage Renal Disease with Recombinant Human Erythropoietin" The New England Journal of Medicine, vol. 316(2) Jan. 8, 1987.
Expert Declaration of Lynda Szczech filed in EP Application 04754383.0 with response of Nov. 12, 2013 Nov. 12, 2013.
Fairbanks, et al. "Iron Deficiency" in Williams, Hematology, McGraw-Hill, 2001, Ed. 6th Chapter 38 2001.
Fairbanks, et al. "Iron Metabolism" in Williams, Hematology, McGraw-Hill, 2001, Ed. 6th Chapter 24 2001.
Fleming, et al. "Microcytic anaemia mice have a mutation in Nramp2, a candidate iron transporter gene." Nature Genetics; vol. 16(4) Aug. 1997.
Fleming, et al "Hepcidin: A Putative Iron-Regulatory Hormone Relevant to Hereditary Hemochromatosis and the Anemia of Chronic Disease," vol. 98(15) Jul. 17, 2001.
Franklin et al., "Hormone-induced Desensitisation of Hormonal Control of Cyclic AMP Levels in Human Diploid Fibroblasts" Nature New Biology, vol. 246(153) Dec. 5, 1973.
Franklin et al., "Inhibition of collagen hydroxylation by 2,7,8-trihydroxyanthraquinone in embryonic-chick tendon cells" Biochem J., vol. 261 1989.
Franklin, Trevor J. et al., "Approaches to the Design of Anti-Fibrotic Drugs," Biochem, Soc. Trans., vol. 19 1991.
Franklin, Trevor J. et al. "Inhibition of Proly 4-Hydroxylase in Vitro and in Vivo by Members of a Novel Series of Phenanthrolinones," Biochem. J.; 353 Jan. 15, 2001.
Ang et al. "Von Hippel-Lindau protein, Chuvash polycythemia and oxygen sensing" 2001, Blood (abstract 3115).
Beguin et al. "Acute Functional Iron Deficiency in Obses Subjects During a Very-Low_Energy All-Protein Diet" Jul. 1997, Am. J. Clin. Nutrition 66(1):75-79 (abstract).
Bothwell et al. "Erythrokinetics IV The plasma iron turnover as a measure of erythropoiesia" May 1, 1957, Blood 12 (5):409-427.
Anonymous, British National Formulary, vol. 45, Pharmaceutical Press London, "Oral Iron" and "Parenteral Iron" pp. 439-440, 442 Mar. 2003.
Rodriguez "Erythropoietin acute reaction and haematological adaptations to short, intermittant ypobaric hypoxia" 2000, Eur. J. Appl. Physiol. 82:170-177.
Calamia et al. "Endoscopic YAG Laser Treatment of Watermelon Stomach Gastric Antral Vascular Ectasia in Patients with Systemic Sclerosis" Sep.-Oct. 2000, Clin. Exper. Rheumatology 18(5):605-608.
Canadian Impeachment Statement of Claim from Akebia Therapeutics, Inc. dated May 29, 2018.
Colehour et al. "Effect of hypoxia on serum iron and the unsaturated iron-binding capacity of serum in rates" 1957, Am. J. Physiol. 191-113-114.
Crowley "Introduction to Human Disease" 1986, Chapter 14, 377-404.
Deicher et al. "Hepcidin: A Molecular link between inflammation and ariaemia" 2004, Nephrol. Dial. Transplant 19:521-529.
Eckardt "Anaemia in end-stage renal disease: pathophysiological considerations" 2001, Nephrol. Dial. Transplant 16 (supp 7):2-8.
Eckardt "Production of erythropoietin by liver cells in vivo and in vitro" 1994, Ann. NY Acad. Sci. 78:50-63.
Eschbach "Improvement in the anemia of chronic renal failure with fluoxymesterone" 1973, Ann. Intern. Med. 78:527-532.
European Patent Court Decision Case Nos. HP-2018-0000036, IL-2019-000031 Dated Apr. 20, 2020: Between : (1) Akebia Therapeutics Inc(2) Otsuka Pharmaceutical Company Limited Claimants-and-Fibrogen, Inc Defendant and between :Astellas Pharma Inc Claimant- and-(1) Akebia Therapeutics Inc (2) Otsuka Pharmaceutical Company Limited (3) Fibrogen, Inc Defendants.
Fabian et al. "Watermelon Stomach as a Cause of Chronic Iron Deficiency Anemia in a Patient with Systemic Sclerosis" Mar. 1999, J. Eur. Acad. Dermatol. Venereology 12(2):161-164 (abstract).
Fisher "A quest for erythropoietin over nine decades" 1998, Ann. Rev. Pharmacol. Toxicol. 36:1-20.
Forsythe et al. "Activation of Vascular Endothelial Growth Factor Gene Transcription by Hypoxia-inducible Factor 1" 1996, Mol. Cell Biol. 16:4804-4813.
Fried "The liver as a source of extrarenal erythropoietin production" 1972 Blood 40:671-677.
Goldberg "Regulation of the erythropoietin gene eveidence that th oxygensensor is a heme protein" 1968, Science 242:1412-1415.
Green-Hernandez et al. "Primary Care Pediatrics" 2001, pp. 496.
Guzman "Prolyl-4-Hydroxylase: An overview" 1999, Guzman, Prolylhydroxylase, Protein Disulfide Isomerase, and Other Structurally Related Proteins 1-34.
Hathom et al. "The influence of hypoxia on iron absorption in the rat" 1971, Gastroenterology 66:76-81.
IPR 2016-01319 decision of Jan. 11, 2017 for U.S. Pat. No. 8,614,204 B2 (GlaxoSmithKline LLC).
IPR 2016-01320 decision of Jan. 11, 2017 for U.S. Pat. No. 8,604,013 B2 (GlaxoSmithKline LLC).
IPR 2016-01322 decision of Jan. 11, 2017 for U.S. Pat. No. 8,604,012 B2 (GlaxoSmithKline LLC).
IPR 2016-01323 decision of Jan. 11, 2017 for U.S. Pat. No. 8,629,131 B2 (GlaxoSmithKline LLC).

(56) References Cited

OTHER PUBLICATIONS

IPR 2016-1315 decision of Jan. 11, 2017 for U.S. Pat. No. 8,466,172 B2 (GlaxoSmithKline LLC).
IPR 2016-1318 decision of Jan. 11, 2017 for U.S. Pat. No. 8,609,646 B2 (GlaxoSmithKline LLC).
Janoff et al. "Levels of plasma bound iron in experimental shock in the rabbit and dog" 1960, Am. J. Physiol. 198:1161-1165.
JP Invalidation No. 2018-800079 preliminary decision with English translation (606).
JP Invalidation No. 2018-800093 preliminary decision with English translation (606.2).
JP Invalidation No. 2018-800102 preliminary decision with English translation (606.1).
Kaelin et al. "Molecular basis of the VHL hereditary cancer syndrome" 2002, Nat. Rev. Cancer 2:673-682.
Kling et al. "Iron Deprivation Increases Erythropoietin Production in Vitro in Normal Subjects and Patients with Malignancy" 1995, Br. Haematol. 95:241-248.
Lawrence et al. "A physiological study in the Peruvian Andes" 1952, Acta Medica Scand. 142:117-131.
Lee "The anemia of chronic disease" 1983, Semin. Hematol. 2:61-80.
Madan "Regulated basal, inducible, and tissue-specific human erythropoietin gene expression in transgenic mice requires multiple cis DNA sequences" May 1, 1995, Blood 85(10):2735-2741.
Mazur et al. "The mechanism of iron release from ferritin as related to its biological properties" 1956, J. Biol. Chem. 213:147-160.
Mazza et al. "Manual of Clinical Hematology" 3rd Edition, The Anemias, 2002, pp. 1-44, 34.35.
Meberg et al. "Smoking during pregnancy-haematological observations in the newborn" 1979, Acta Paediatr. Scand. 68:291-292.
Minet et al. "Role of HIF-1 as a transcription factor involved in embryonic development, cancer progression and apoptosis" 2000, Intl. J. Molec. Med. 5:253-259.
Mole et al. "Regulation of HIF by the von Hippel-Lindau Tumour Suppressor: Implications for Cellular Oxygen Sensing" 2001, IUBMB Life 52(1-2):43-47.
Morgan "Effect of hypoxia on serum concentration of transfferrin and other serum proteins in human subjects" 1970, J. Lab. Clin. Med. 75:1006-1012.
Morris et al. "Erythropoietin Therapy in Peritoneal Dialysis Patients" May 23-26, 2000, Peritoneal Dialysis International 20(supp 2):S178-S182.
Robinson et al. "The effect of oral therapy with cobaltous chloride on the blood of patients suffering with chronic supperative infectoin" 1949, New Eng. J. Med. 240:749-753.
Pietrangelo et al. "Mechanisms of Disease: the role of hepcidin in iron homeostasis implications for hemochromatosis and other disorders" 2004, Nature Clinical Practice Gastroenterology & Hepatology 1:39-45.
Rapetti et al. "Correction of Iron Deficiency with an Iron-Fortified Fluid Whole Cow's Milk in Children: Results of Pilot Study" May-Jun. 1997, J. Pediat. Hemat./Oncol. 19(3):192-196 (abstract).
Roach et al. "Hypoxia: From Genes to the Bedside" 2003, NY Kluwer Academic vol. 502.
Ryhanen et al. "Lysl hydroxylase further purification and Charaacterizatoin of the enzyme from chick embryos and chick embryo cartilage" 1976, Biochem. Biophys. Acta 438:71-89.
Samaja "Hypoxia-dependent Protein Expression: Erythropoietin" 2001, High Alt. Med. Biol. 2(2):155-163.
Schaefer "Hypochromic red blood cells and reticulocytes" 1999, Kidney Intl. 55:S44-S48.
Schulz et al. "Investigations on latent erythropoietin (ESF) deficiency in non-anaemic patients with chronic renal disease using hypoxic stimulation methods" 1978, Klin. Wschr. 56:337-340.
Semenza et al. "Regulation of Cardiovascular Development and Physiology by Hypoxia-Inducible Factor 1a" 1999, Ann. NY Acad. Sci. 874:262-288.
Simpson "Effect of hypoxic exposure on iron absorption in heterozygous hypotransferrinaemic mice" 1992, Ann. Hematol. 65:260-264.
St. Clair et al. "Rheumatoid Arthritis" 2004 textbook extract, pp. 16-17, 492-493.
Suominen et al. "Single Values of Serum Transferring Receptor and Transferrin Receptor Ferritin Index Can be Used to Detect True and Functional Iron Deficiency in Rheumatoid Arthritis Patients with Anemia" May 2000, Arth. & Rheumatism 43(5):1016-1020.
Tokuriki et al., Stability effects of mutations and protein evolvability; Current Opinion in Structural Biology, 19:596-604 (2009).
Wang et al. "Hypoxia-Inducible Factor 1 is a basic helix-loop-helix-PAS heterodimer regulated by cellular O2 tension" 1996, PNAS 92:5510-5514.
Ward et al. "Serum Level of Erythropoietin in Anemias Associated with Chronic Infection, Malignancy, and Primary Haematopoietic Disease" 1971, J. Clin. Investig. 50:332-335.
Wenger et al. "Oxygen(es) and the Hypoxia-Inducible Factor-1" 1997, Biol. Chem. 378:609-616.

\* cited by examiner

ENHANCED ERYTHROPOIESIS AND IRON METABOLISM

This application is a continuation of U.S. application Ser. No. 14/084,443, filed on 19 Nov. 2013, now U.S. Pat. No. 9,920,011, which is a divisional of U.S. application Ser. No. 10/861,590, filed on 3 Jun. 2004, now U.S. Pat. No. 8,614,204, which application claims the benefit of U.S. Provisional Application Ser. No. 60/476,704, filed on 6 Jun. 2003; U.S. Provisional Application Ser. No. 60/566,488, filed on 29 Apr. 2004; U.S. Provisional Application Ser. No. 60/566,237, filed on 29 Apr. 2004; and U.S. Provisional Application Ser. No. 60/569,797, filed on 10 May 2004, each of which is incorporated by reference herein in its entirety.

FIELD OF THE INVENTION

The present invention relates to methods and compounds for regulating or enhancing erythropoiesis and iron metabolism, and for treating or preventing iron deficiency and anemia of chronic disease.

BACKGROUND OF THE INVENTION

Anemia generally refers to any abnormality in hemoglobin or erythrocytes that leads to reduced oxygen levels in the blood. Anemia can also develop in association with chronic diseases, e.g., chronic infection, neoplastic disorders, chronic inflammatory disorders, including disorders with consequent inflammatory suppression of marrow, etc. Anemia of chronic disease is one of the most common syndromes in medicine.

Anemia of chronic disease (ACD) is often associated with iron deficiencies. ACD can develop from inadequate availability of iron (e.g., anemia of iron deficiency) or, in cases where total body iron is adequate but the requirements for hemoglobin production are defective (e.g., functional iron deficiency). Iron is required for production of red blood cell hemoglobin in erythropoietic precursor cells of the bone marrow.

Numerous physiologic deficiencies are observed in patients with anemia of chronic disease, including reduced erythropoietin (EPO) production, reduced EPO responsiveness of the bone marrow, and reduced iron metabolism, including reduced iron absorption from the gut, reduced iron trans-enterocyte transport, reduced iron oxidation to the ferric state by hephaestin or ceruloplasmin, reduced iron binding and uptake by transferrin and transferrin receptor, and reduced iron transport to the marrow where iron utilization occurs, including heme synthesis. Individually and together, these physiologic deficiencies contribute to ineffective or impaired erythropoiesis, which can lead to microcytic anemia and hypochromic red blood cells associated with reduced hemoglobin production and reduced oxygen transport.

Anemia of chronic disease is associated with increased production of inflammatory cytokines (Means (1995) Stem cells 13:32-37 and Means (1999) Int J Hematol 70:7-12.), including, for example, tumor necrosis factor-α (TNF-α), interleukin-1β (IL-1β), IL-6, and interferon-γ (IFN-γ). In several in vitro and in vivo animal model systems, inflammatory cytokines negatively affected the ability to mediate EPO production, EPO responsiveness, and the coordinate regulation of iron metabolism (Roodman et al. (1989) Adv Exp Med Biol 271:185-196; Fuchs et al. (1991) Eur J Hematol 46:65-70; Jelkmann et al. (1994) Ann NY Acad Sci 718:300-311; Vannucchi et al. (1994) Br J Hematol 87:18-23; and Oldenburg et al. (2001) Aliment Pharmacol Ther 15:429-438.) Administration of erythropoietin failed to reverse anemia in mice continuously exposed to TNF-α (Clibon et al. (1990) Exp Hematol 18:438-441). Increased levels of inflammatory cytokines, such as TNF-α, IL-1β, and INF-γ, contribute to defective EPO production and EPO resistance observed in patients with anemia of chronic disease (Jelkmann et al. (1991) Ann NY Acad Sci 718:300-311 and Macdougall and Cooper (2002) Neprol Dial Transplant 17(11):39-43.). Therefore, various cytokines, e.g., inflammatory cytokines and cytokines associated with inflammation, are involved in many aspects of the pathogenesis of anemia of chronic disease, including inhibition of erythroid progenitors, inhibition of EPO production, and impairment of iron release and iron availability for erythropoiesis.

There is thus a need in the art for methods of treating or preventing anemia of chronic disease. There is a need in the art for methods of overcoming the deficiencies in current use of recombinant EPO to treat anemia of chronic disease. In particular, there remains a need for methods and compounds effective at overcoming suppressed EPO production and decreased EPO responsiveness associated with anemia of chronic disease, for methods and compounds effective at enhancing regulation of iron metabolism and overcoming deficiencies of altered or abnormal iron metabolism and utilization, and for methods and compounds effective at enhancing total or complete erythropoiesis by improving the metabolic pathways related to EPO production, EPO responsiveness and signaling, and iron availability, utilization, uptake, transport, processing, etc. There is a need in the art for methods of overcoming or of ameliorating the consequences of cytokine-induced effects in subjects having anemia of chronic disease.

Iron deficiency is one of the most common nutritional deficiencies worldwide and is the leading cause of anemia on a global basis. Iron balance is fundamentally regulated by the rate of erythropoiesis and the size of iron stores. Iron deficiency can occur with or without anemia, and has been associated with impaired cognitive development.

Iron deficiency is defined as inadequate iron supply (levels or stores) or as inadequate availability or utilization of iron in the body. This can be due to nutritional deficiencies, e.g., lack of iron in the diet; to iron malabsorption, due, for example, to surgery (post-gastrectomy) or disease (Crohn's disease); or to a depletion in iron supply or increased iron loss due to chronic or acute blood loss resulting from injury or trauma, menses, blood donation, phlebotomy (such as due to various procedures, surgeries); from increased iron demand, e.g., due to rapid growth in infancy or adolescence, pregnancy, erythropoietin therapy, etc.

Iron deficiency can also be functional iron deficiency, e.g., iron deficiency characterized by the subject's impaired ability to access and utilize iron stores. Iron is not available at a rate sufficient to allow normal hemoglobinization of erythrocytes, leading to reduced reticulocyte and erythrocyte cellular hemoglobin content. Functional iron deficiency is often seen in healthy individuals with apparently normal or even increased iron stores but with impaired iron availability, as measured, e.g., by low levels of percent transferrin saturation. This type of iron deficiency is frequently associated with acute or with chronic inflammation.

Iron deficiency of any kind can lead to iron-deficient or iron-restricted erythropoiesis, in which red blood cell numbers decrease and circulating red blood cells are smaller than normal (microcytic) and lack adequate hemoglobin, and as such are pale in color (hypochromic).

Subjects with iron deficiency, including functional iron deficiency, can develop impaired hemoglobin synthesis, reduced % transferrin saturation, and decreased hemoglobin and hematocrit levels, leading to iron deficiency anemia. Iron deficiency anemia is the most common anemia in the world. Iron is an essential component of hemoglobin; without iron, the marrow is unable to produce hemoglobin effectively. Iron deficiency anemia may occur in subjects with depleted or impaired iron supply, or may occur in subjects having functional iron deficiency, when iron is present in storage but is unavailable, e.g., for hemoglobin production.

In view of the above, there is a need in the art for methods of treating or preventing disorders associated with iron metabolism, and a need in the art for methods of enhancing iron metabolism. There is a need for methods of treating or preventing iron deficiency, including functional iron deficiency, and for treating or preventing associated conditions such as microcytosis and iron deficiency anemia.

The present invention provides methods and compounds for enhancing the metabolic and physiologic pathways that contribute to complete and effective erythropoiesis, and in particular, for treating anemia of chronic disease. Methods and compounds for overcoming the suppressive/inhibitory effects of inflammatory cytokines on EPO production and responsiveness are also provided. Additionally the present invention provides methods and compounds for enhancing iron metabolism, and for treating or preventing conditions associated with impaired iron metabolism, such as iron deficiency, including functional iron deficiency, iron deficiency anemia, microcytosis, iron-deficient erythropoiesis, etc.

SUMMARY OF THE INVENTION

The present invention relates to methods and compounds for inducing enhanced or complete erythropoiesis in a subject. In particular, the methods comprise inducing enhanced or complete erythropoiesis by stabilizing HIFα in a subject. Methods of inducing enhanced erythropoiesis by inhibiting HIF prolyl hydroxylase are specifically contemplated. In specific embodiments, the methods comprise administering to a subject a compound of the invention. In various embodiments, the subject can be a cell, tissue, organ, organ system, or whole organism.

The subject is, in various embodiments, a cell, tissue, organ, organ system, or whole organism. In particular embodiments, the organism is a mammal, preferably, a human.

In one aspect, the method increases the production of factors required for differentiation of erythrocytes from hematopoietic progenitor cells including, e.g., hematopoietic stem cells (HSCs), CFU-GEMM (colony-forming-unit-granulocyte/erythroid/monocyte/megakaryocyte) cells, etc. Factors that stimulate erythropoiesis include, but are not limited to, erythropoietin. In another aspect, the methods increase the production of factors required for iron uptake, transport, and utilization. Such factors include, but are not limited to, erythroid aminolevulinate synthase, transferrin, transferrin receptor, ceruloplasmin, etc. In yet another aspect, the method increases factors required for differentiation of erythrocytes and additionally factors required for iron uptake, transport, and utilization.

In another embodiment, the methods of the invention enhance responsiveness of hematopoietic precursors to erythropoietin. As described above, such precursors include HSCs, CFU-GEMMs, etc. The responsiveness of the precursor cells can be augmented, e.g., by altering expression of erythropoietin receptors, intracellular factors involved in erythropoietin signaling, and secreted factors that facilitate interaction of erythropoietin with the receptors.

In another aspect, the methods can be used to overcome inhibition of erythropoiesis induced by inflammatory cytokines such as tumor necrosis factor-α (TNF-α), interleukin-1β (IL-1β), and the like. In particular aspects, the methods can be used to treat anemia that is refractive to treatment with exogenously administered erythropoietin. Such anemia can be caused, e.g., by chronic inflammatory or autoimmune disorders including, but not limited to, chronic bacterial endocarditis, osteomyelitis, rheumatoid arthritis, rheumatic fever, Crohn's disease, and ulcerative colitis.

In certain embodiments, the methods of the invention can be used to treat anemia of chronic disease. Methods for inducing enhanced or complete erythropoiesis in patients with anemia of chronic disease are specifically provided. In particular embodiments, the methods increase the amount of iron available to make new red blood cells.

In another aspect, the present invention provides methods for enhancing EPO responsiveness of the bone marrow.

Methods for inhibiting TNFα suppression of EPO are specifically provided, as are methods for inhibiting IL-1β suppression of EPO.

The present invention relates to methods for the treatment/prevention of anemia of chronic disease, and methods for regulation of iron processing and treatment/prevention of conditions associated with deficiencies in iron and/or iron processing.

In one aspect, the invention provides a method for treating anemia of chronic disease in a subject, the method comprising administering to the subject an effective amount of a compound that stabilizes the alpha subunit of hypoxia inducible factor (HIF), thereby treating anemia of chronic disease in the subject. Methods for achieving specific physiological effects in a subject having anemia of chronic disease are also provided; in particular, methods for increasing reticulocytes, increasing mean corpuscular cell volume, increasing mean corpuscular hemoglobin, increasing hematocrit, increasing hemoglobin, and increasing red blood cell count, etc., in a subject having anemia of chronic disease, each method comprising administering to the subject an effective amount of a compound that stabilizes the alpha subunit of hypoxia inducible factor (HIF), thereby achieving the desired physiological effect. In various aspects, the anemia of chronic disease is associated with, e.g., inflammation, autoimmune disease, iron deficiency, microcytosis, malignancy, etc.

In various embodiments, the subject is a cell, tissue, or organ. In other embodiments, the subject is an animal, preferably a mammal, most preferably a human. When the subject is a cell, the invention specifically contemplates that the cell can be an isolated cell, either prokaryotic or eukaryotic. In the case that the subject is a tissue, the invention specifically contemplates both endogenous tissues and in vitro tissues, e.g., tissues grown in culture. In preferred embodiments, the subject is an animal, particularly, an animal of mammalian species including rat, rabbit, bovine, ovine, porcine, murine, equine, and primate species. In a most preferred embodiment, the subject is human.

Stabilization of HIFα can be accomplished by any of the methods available to and known by those of skill in the art, and can involve use of any agent that interacts with, binds to, or modifies HIFα or factors that interact with HIFα, including, e.g., enzymes for which HIFα is a substrate. In certain aspects, the present invention contemplates providing a constitutively stable HIFα variant, e.g., stable HIF muteins, etc, or a polynucleotide encoding such a variant. In other aspects, the present invention contemplates that stabilizing HIFα comprises administering an agent that stabilizes HIFα. The agent can be composed of polynucleotides, e.g. antisense sequences; polypeptides; antibodies; other proteins; carbohydrates; fats; lipids; and organic and inorganic substances, e.g., small molecules, etc. In a preferred embodiment, the present invention contemplates stabilizing HIFα, e.g., in a subject, by administering to the subject an agent that stabilizes HIFα wherein the agent is a compound, e.g., small molecule compound, etc., that stabilizes HIFα.

In various aspects, HIFα is HIF1α, HIF2α, or HIF3α. In a preferred aspect, stabilizing HIFα comprises administering to the subject an effective amount of a compound that inhibits HIF hydroxylase activity. In certain aspects, the HIF hydroxylase is selected from the group consisting of EGLN1, EGLN2, and EGLN3.

In one embodiment, the invention provides a method for increasing mean corpuscular volume in a subject, the method comprising administering to the subject an effective amount of a compound that stabilizes the alpha subunit of hypoxia inducible factor (HIF). In a further embodiment, the invention provides a method for increasing mean corpuscular hemoglobin levels in a subject, the method comprising administering to the subject an effective amount of a compound that stabilizes the alpha subunit of hypoxia inducible factor (HIF). In another embodiment, the present invention encompasses a method for reducing microcytosis in a subject, the method comprising administering to the subject an effective amount of a compound that stabilizes the alpha subunit of hypoxia inducible factor (HIF).

The invention further provides a method for treating or preventing microcytic anemia, the method comprising administering to the subject an effective amount of a compound that stabilizes the alpha subunit of hypoxia inducible factor (HIF).

In one aspect, the invention relates to a method for treating or preventing a condition associated with iron deficiency in a subject, the method comprising administering to the subject an effective amount of a compound that stabilizes the alpha subunit of hypoxia inducible factor (HIF). In a particular aspect, the invention provides a method for improving iron processing in a subject, the method comprising administering to the subject an effective amount of a compound that stabilizes the alpha subunit of hypoxia inducible factor (HIF). A method for treating or preventing a condition associated with compromised iron availability in a subject is also provided, the method comprising administering to the subject an effective amount of a compound that stabilizes the alpha subunit of hypoxia inducible factor (HIF).

In other embodiments, the invention relates to a method for overcoming cytokine-induced effects in a subject. In particular, the invention provides in one aspect a method for overcoming cytokine-suppression of EPO production in a subject, the method comprising administering to the subject an effective amount of a compound that stabilizes the alpha subunit of hypoxia inducible factor (HIF). The invention further provides a method for overcoming cytokine-suppression of iron availability in a subject, the method comprising administering to the subject an effective amount of a compound that stabilizes the alpha subunit of hypoxia inducible factor (HIF). In another aspect, the present invention encompasses a method for treating or preventing cytokine-associated anemia in a subject, the method comprising administering to the subject an effective amount of a compound that stabilizes the alpha subunit of hypoxia inducible factor (HIF). Methods for increasing EPO production in the presence of a cytokine in a subject, the methods comprising administering to the subject an effective amount of a compound that stabilizes the alpha subunit of hypoxia inducible factor (HIF), are also provided. In specific embodiments, the cytokine is selected from the group consisting of TNF-α and IL-1β.

In one aspect, the invention provides a method for reducing cytokine-induced VCAM expression in a subject, the method comprising administering to the subject an effective amount of a compound that stabilizes the alpha subunit of hypoxia inducible factor (HIF). In a specific aspect, the cytokine is TNF-α or IL-1β. In one aspect, the method applies to reduction of cytokine-induced VCAM expression in endothelial cells in the subject. In another aspect, the subject has a condition selected from the group consisting of inflammatory disease, autoimmune disease, and anemia of chronic disease.

In another aspect, the invention provides a method for reducing cytokine-induced E-selectin expression in a subject, the method comprising administering to the subject an effective amount of a compound that stabilizes the alpha subunit of hypoxia inducible factor. In a specific aspect, the cytokine is TNF-α or IL-1β. In one aspect, the method applies to reduction of cytokine induced E-selectin expression in endothelial cells in the subject. In another aspect, the subject has a condition selected from the group consisting of inflammatory disease, autoimmune disease, and anemia of chronic disease.

The invention provides various methods of regulating/enhancing iron processing and iron metabolism. In one aspect, the invention provides methods for increasing iron transport, uptake, utilization, and absorption in a subject, each of the methods comprising administering to the subject an effective amount of a compound that stabilizes the alpha subunit of hypoxia inducible factor (HIF). In particular embodiments, the invention provides methods for increasing transferrin expression, transferrin receptor expression, IRP-2 expression, ferritin expression, ceruloplasmin expression, NRAMP2 expression, sproutin expression, and ALAS-2 expression in a subject, each method comprising administering to the subject an effective amount of a compound that stabilizes the alpha subunit of hypoxia inducible factor (HIF). In other embodiments, the invention provides methods for decreasing hepcidin expression, the method comprising administering to the subject an effective amount of a compound that stabilizes the alpha subunit of hypoxia inducible factor (HIF). Methods for increasing heme synthesis in a subject by administering to the subject an effective amount of a compound that stabilizes the alpha subunit of hypoxia inducible factor (HIF) are also provided.

In certain aspects, the invention contemplates methods for increasing serum iron, increasing transferrin saturation, increasing soluble transferrin receptor levels, and increasing serum ferritin levels in a subject, the methods comprising administering to the subject an effective amount of a compound that stabilizes the alpha subunit of hypoxia inducible factor (HIF). In a further aspect, the invention provides a method for increasing iron transport to bone marrow in a subject, the method comprising administering to the subject an effective amount of a compound that stabilizes the alpha subunit of hypoxia inducible factor (HIF).

In one aspect, the present methods are applied to treatment of or manufacture of a medicament for a subject, preferably a human subject, having any of the disorders and conditions discussed herein. It is to be understood that various parameters associated with clinical conditions vary according to age, gender, etc. In one aspect, the subject has a serum ferritin level below normal range, e.g., below 50-200 µg/L; thus, a subject having serum ferritin levels below 200 ng/ml, below 150 ng/ml, below 100 ng/ml, below 75 ng/ml, and below 50 ng/ml could be a suitable subject for treatment with the methods or use of medicaments provided by the present invention. Alternatively, a suitable subject could be identified by demonstrating a total iron-binding capacity (TIBC) of less than normal range, e.g., less than TIBC 300-360 µg/dL.

In another embodiment, the subject has a serum iron level below the normal range, e.g., below serum iron levels of 50-150 m/dL. Other appropriate parameters for identifying suitable subjects include transferrin saturation measurements of below 30-50%, marrow sideroblast measurements of below 40-60%, and hemoglobin levels of below about 10 to 11 g/dL. Any of the above parameters are measured, e.g., as in standard hematological tests, blood chemistry and complete blood count (CBC) analysis, typically presented as a measurement of several blood parameters, and obtained, e.g., by analysis of blood by an automated instrument which measures, for example, red blood cell count, white blood cell count, platelet count, and red cell indices. Measurement may be by any standard means of measurement of hematological and/or biochemical blood analysis, including, e.g., automated systems such as the CELL DYN 4000 analyzer (Abbott Laboratories, Abbott Park Ill.), the Coulter GenS analyzer (Beckman Coulter, Inc., Fullerton Calif.), the Bayer ADVIA 120 analyzer (Bayer Healthcare AG, Leverkusen, Germany), etc.

In one aspect, the invention encompasses a method for treating or preventing iron deficiency in a subject, the method comprising administering to the subject an effective amount of a compound that stabilizes HIFα, thereby treating or preventing iron deficiency in the subject. In further aspects, the iron deficiency is functional iron deficiency; is associated with anemia; is associated with a disorder selected from the group consisting of an inflammation, infection, immunodeficiency disorder, and neoplastic disorder; or is associated with a disorder selected from the group consisting of anemia of chronic disease, iron deficiency anemia (IDA), and microcytic anemia.

A subject of the invention could be a subject with any clinically accepted standard measurement indicative of iron deficiency or of a risk for developing iron deficiency. For example, in certain embodiments, the subject has low serum ferritin levels (<20 ng/ml), or reduced % transferrin saturation, e.g., less than 16% (in adults). Serum ferritin levels of below 50 ng/ml, below 40 ng/ml, below 30 ng/ml, and below 20 ng/ml are specifically contemplated. It is noted that if the subject has or is at risk for having an iron deficiency that is functional iron deficiency, the serum ferritin levels could be increased above normal range, e.g., 200 ng/ml and above. Iron deficiency can be observed through onset of iron-restricted/iron-deficient erythropoiesis (impairment of hemoglobin synthesis that is observed typically when % transferrin saturation falls below 15 to 20%). These iron parameters can be measured using any standard CBC or biochemical analysis described above, and/or by use of automated devices more specifically directed to iron analysis, e.g., the Unimate 5 Iron and Unimate 7 UIBC kits (Roche, Switzerland).

A subject that might benefit from the present methods of treating or preventing could be a subject having or at risk for having iron deficiency anemia; for example, a subject having a transferrin saturation % of 10-15% or of below 10%.

In one aspect, the subject having or at risk for having iron deficiency has or is at risk for having functional iron deficiency. A reticulocyte hemoglobin content of less than 28 picograms/cell could be indicative of such a condition. In another aspect, the subject having or at risk for having functional iron deficiency displays greater than 5% hypochromic red cells.

In certain embodiments, the subject is one having or at risk for having anemia of chronic disease. Such a subject could display mild or moderate anemia, e.g., hemoglobin levels of around 10-13 g/dL, or, more particularly, 10-11 g/dL. In other embodiments, more acute anemia is displayed, e.g., hemoglobin levels below 10 g/dL, including levels below 5 g/dL, and levels below 3 g/dL. In some embodiments, the subject having or at risk for having anemia of chronic disease displays abnormalities in iron distribution. Such abnormalities could be, e.g., serum iron levels below around 60 µg/dL, or serum ferritin levels above normal range, e.g., of above 200 ng/ml, above 300 ng/ml, or above 400 ng/ml.

In certain aspects, the subject could have or be at risk for having microcytic anemia. Such a subject may, for example, demonstrate a mean corpuscular volume of less than 80 femtoliters measured, e.g., as part of complete blood count analysis. In other aspects, the subject has a mean corpuscular volume of less than the normal value of 90+/−8 femtoliters. The subject can have, in various aspects, a reduced mean cell hemoglobin count, for example, a mean cell hemoglobin count of less than 30+/−3 picograms of hemoglobin/cell; or a reduced mean cell hemoglobin concentration, e.g., a mean cell hemoglobin concentration of less than 33+/−2%.

A method for treating or preventing functional iron deficiency in a subject, the method comprising administering to the subject an effective amount of a compound that stabilizes HIFα, thereby treating or preventing functional iron deficiency, is also provided.

In one embodiment, the present invention provides a method for regulating or enhancing iron metabolism or an iron metabolic process in a subject, the method comprising administering to the subject an effective amount of a compound that stabilizes HIFα, thereby regulating or enhancing iron metabolism or the iron metabolic process in the subject. In another embodiment, the invention provides a method for regulating or enhancing an iron metabolic process selected from the group consisting of iron uptake, iron absorption, iron transport, iron storage, iron processing, iron mobilization, and iron utilization, the method comprising administering to the subject an effective amount of a compound that stabilizes HIFα, thereby regulating or enhancing the iron metabolic process in the subject.

A method for increasing iron absorption in a subject, the method comprising administering to the subject an effective amount of a compound that stabilizes HIFα, thereby increasing iron absorption in the subject, is also provided herein. In certain aspects, the iron absorption is in the intestine; is absorption of dietary iron; or is in duodenal enterocytes.

The following methods are also contemplated herein: a method for increasing iron transport in a subject, the method comprising administering to the subject an effective amount of a compound that stabilizes HIFα, thereby increasing iron transport in the subject; a method for increasing iron storage in a subject, the method comprising administering to the subject an effective amount of a compound that stabilizes HIFα, thereby increasing iron storage in the subject; a method for increasing iron uptake in a subject, the method comprising administering to the subject an effective amount of a compound that stabilizes HIFα, thereby increasing iron uptake in the subject; a method for increasing iron processing in a subject, the method comprising administering to the subject an effective amount of a compound that stabilizes HIFα, thereby increasing iron processing in the subject; a method for increasing iron mobilization in a subject, the method comprising administering to the subject an effective amount of a compound that stabilizes HIFα, thereby increasing iron mobilization in the subject; and a method for increasing iron utilization in a subject, the method comprising administering to the subject an effective amount of a compound that stabilizes HIFα, thereby increasing iron utilization in the subject.

In one embodiment, the invention contemplates a method for increasing iron availability for erythropoiesis in a subject, the method comprising administering to the subject an effective amount of a compound that stabilizes HIFα, thereby increasing iron availability for erythropoiesis in the subject. In various embodiments, the increasing iron availability for erythropoiesis is increasing iron availability for heme synthesis; is increasing iron availability for hemoglobin production; or is increasing iron availability for red blood cell production.

The invention further provides methods for regulating expression of iron regulatory factors in a subject, the method comprising administering to the subject an effective amount of a compound that stabilizes HIFα, thereby regulating expression of iron metabolic factors in the subject.

Methods for increasing expression of certain iron regulatory factors are encompassed herein, including: a method for increasing transferrin receptor expression in a subject, the method comprising administering to the subject an effective amount of a compound that stabilizes HIFα, thereby increasing transferrin receptor expression in the subject; a method for increasing transferrin expression in a subject, the method comprising administering to the subject an effective amount of a compound that stabilizes HIFα, thereby increasing transferrin expression in the subject; a method for increasing ceruloplasmin expression in a subject, the method comprising administering to the subject an effective amount of a compound that stabilizes HIFα, thereby increasing ceruloplasmin expression in the subject; a method for increasing NRAMP2 (slc11a2) expression in a subject, the method comprising administering to the subject an effective amount of a compound that stabilizes HIFα, thereby increasing NRAMP2 expression in the subject; a method for increasing duodenal cytochrome b reductase 1 expression in a subject, the method comprising administering to the subject an effective amount of a compound that stabilizes HIFα, thereby increasing duodenal cytochrome b reductase 1 expression in the subject; and a method for increasing 5-aminolevulinate synthase expression in a subject, the method comprising administering to the subject an effective amount of a compound that stabilizes HIFα, thereby increasing 5-aminolevulinate synthase expression in the subject.

In one embodiment, the invention provides a method for increasing serum iron in a subject, the method comprising administering to the subject an effective amount of a compound that stabilizes HIFα, thereby increasing serum iron in the subject. In certain embodiments, the subject is a human, and the serum iron levels are increased to a value between 50 to 150 μg/dL.

In another aspect, the present invention provides methods for increasing total iron-binding capacity (TIBC) in a subject. The method comprising administering to the subject an effective amount of a compound that stabilizes HIFα, thereby increasing TIBC in the subject. In a preferred aspect, the subject is a human and the total iron-binding capacity is increased to a value between 300 to 360 μg/dL.

Methods and compounds for modulating serum ferritin levels in a subject are provided. In a certain embodiment, the subject is a human, and the serum ferritin levels are increased above 15 μg/L. In a further embodiment, the subject is a human adult male, and the serum ferritin level is increased to a value of about 100 μg/L. In another embodiment, the subject is a human adult female, and the serum ferritin level is increased to a level of about 30 μg/L.

In one aspect, the invention includes a method for increasing transferrin saturation in a subject, the method comprising administering to the subject an effective amount of a compound that stabilizes HIFα, thereby increasing transferrin saturation in the subject. In one aspect, the transferrin saturation is increased above a level selected from the group consisting of 10%, 15%, 20%, 30%, 40%, and 50%. The present invention encompasses methods for increasing percent transferrin saturation in a subject. In one embodiment, the subject is a human and the percent transferrin saturation is increased to a value above 18%. In another embodiment, the percent transferrin saturation is increased to a value between 25 to 50%. Percent transferrin is typically calculated using the formula: (serum iron)(100)/(TIBC).

Methods for increasing soluble transferrin receptor levels in a subject, the methods comprising administering to the subject an effective amount of a compound that stabilizes HIFα, thereby increasing soluble transferrin receptor levels in the subject, are also provided. The invention further provides methods for increasing total erythroid marrow mass as measured by, e.g., serum transferrin receptor levels. In one aspect, the subject is human and the serum transferrin receptor level is increased to 4 to 9 μg/L as determined by immunoassay.

A method for decreasing hepcidin expression in a subject is provided, the method comprising administering to the subject an effective amount of a compound that stabilizes HIFα, thereby decreasing hepcidin expression in the subject.

In one embodiment, the invention provides a method for treating or preventing a disorder associated with iron deficiency in a subject, the method comprising administering to the subject an effective amount of a compound that stabilizes HIFα, thereby treating or preventing the disorder associated with iron deficiency in the subject. In one embodiment, the iron deficiency is functional iron deficiency. In various embodiments, the disorder is selected from the group consisting of an inflammation, an infection, an immunodeficiency disorder, and a neoplastic disorder; or is selected from the group consisting of anemia of chronic disease, iron deficiency anemia, and microcytic anemia.

The invention provides a method for enhancing erythropoiesis in a subject having or at risk for having iron deficiency, the method comprising administering to the subject an effective amount of a compound that stabilizes HIFα, thereby enhancing erythropoiesis in the subject. It is contemplated in a certain aspect that the iron deficiency is functional iron deficiency.

The invention further provides a method for enhancing erythropoiesis in a subject, wherein the subject has or is at risk for having functional iron deficiency, the method comprising administering to the subject an effective amount of a compound that stabilizes HIFα, thereby enhancing erythropoiesis in the subject. In various aspects, the chronic disease is selected from the group consisting of an inflammation, an infection, an immunodeficiency disorder, and a neoplastic disorder.

A method for enhancing erythropoiesis in a subject, wherein the subject has or is at risk for having anemia of chronic disease, is additionally provided, the method comprising administering to the subject an effective amount of a compound that stabilizes HIFα, thereby enhancing erythropoiesis in the subject.

In one embodiment, the invention encompasses a method for enhancing erythropoiesis in a subject wherein the subject is refractory to EPO therapy, the method comprising administering to the subject an effective amount of a compound that stabilizes HIFα, thereby enhancing erythropoiesis in the subject.

A method for treating or preventing anemia of chronic disease in a subject, the method comprising administering to the subject an effective amount of a compound that stabilizes HIFα, thereby treating or preventing anemia of chronic disease in the subject, is also provided. It is contemplated in certain aspects that the anemia of chronic disease is associated with a condition selected from the group consisting of an inflammation, an infection, an immunodeficiency disorder, and a neoplastic disorder.

The invention specifically contemplates the following: a method for increasing reticulocytes in a subject having a chronic disease, the method comprising administering to the subject an effective amount of a compound that stabilizes HIFα, thereby increasing reticulocytes in the subject; a method for increasing hematocrit in a subject having a chronic disease, the method comprising administering to the subject an effective amount of a compound that stabilizes HIFα, thereby increasing hematocrit in the subject; a method for increasing hemoglobin in a subject having a chronic disease, the method comprising administering to the subject an effective amount of a compound that stabilizes HIFα, thereby increasing hemoglobin in the subject; a method for increasing red blood cell count in a subject having a chronic disease, the method comprising administering to the subject an effective amount of a compound that stabilizes HIFα, thereby increasing red blood cell count in the subject; a method for increasing mean corpuscular volume in a subject having a chronic disease, the method comprising administering to the subject an effective amount of a compound that stabilizes HIFα, thereby increasing mean corpuscular volume in the subject; a method for increasing mean corpuscular hemoglobin in a subject having a chronic disease, the method comprising administering to the subject an effective amount of a compound that stabilizes HIFα, thereby increasing mean corpuscular hemoglobin in the subject; a method for increasing serum iron in a subject having a chronic disease, the method comprising administering to the subject an effective amount of a compound that stabilizes HIFα, thereby increasing serum iron in the subject; and a method for increasing transferrin saturation in a subject having a chronic disease, the method comprising administering to the subject an effective amount of a compound that stabilizes HIFα, thereby increasing transferrin saturation in the subject. In any one of these methods, the chronic disease is in certain embodiments selected from the group consisting of an inflammation, an infection, an immunodeficiency disorder, and a neoplastic disorder; or is selected from the group consisting of anemia of chronic disease, anemia of iron deficiency, iron deficiency, functional iron deficiency, and microcytic anemia.

The following methods are additionally provided: a method for increasing reticulocytes in a subject having iron deficiency, the method comprising administering to the subject an effective amount of a compound that stabilizes HIFα, thereby increasing reticulocytes in the subject; a method for increasing hematocrit in a subject having iron deficiency, the method comprising administering to the subject an effective amount of a compound that stabilizes HIFα, thereby increasing hematocrit in the subject; a method for increasing hemoglobin in a subject having iron deficiency, the method comprising administering to the subject an effective amount of a compound that stabilizes HIFα, thereby increasing hemoglobin in the subject; a method for increasing red blood cell count in a subject having iron deficiency, the method comprising administering to the subject an effective amount of a compound that stabilizes HIFα, thereby increasing red blood cell count in the subject; a method for increasing mean corpuscular volume in a subject having iron deficiency, the method comprising administering to the subject an effective amount of a compound that stabilizes HIFα, thereby increasing mean corpuscular volume in the subject; a method for increasing mean corpuscular hemoglobin in a subject having iron deficiency, the method comprising administering to the subject an effective amount of a compound that stabilizes HIFα, thereby increasing mean corpuscular hemoglobin in the subject; a method for increasing serum iron in a subject having iron deficiency, the method comprising administering to the subject an effective amount of a compound that stabilizes HIFα, thereby increasing serum iron in the subject; and a method for increasing transferrin saturation in a subject having iron deficiency, the method comprising administering to the subject an effective amount of a compound that stabilizes HIFα, thereby increasing transferrin saturation in the subject. In any one of these methods, the iron deficiency in certain embodiments is functional iron deficiency.

The following methods are further contemplated: a method for increasing reticulocytes in a subject having functional iron deficiency, the method comprising administering to the subject an effective amount of a compound that stabilizes HIFα, thereby increasing reticulocytes in the subject; a method for increasing hematocrit in a subject having functional iron deficiency, the method comprising administering to the subject an effective amount of a compound that stabilizes HIFα, thereby increasing hematocrit in the subject; a method for increasing hemoglobin in a subject having functional iron deficiency, the method comprising administering to the subject an effective amount of a compound that stabilizes HIFα, thereby increasing hemoglobin in the subject; a method for increasing red blood cell count in a subject having functional iron deficiency, the method comprising administering to the subject an effective amount of a compound that stabilizes HIFα, thereby increasing red blood cell count in the subject; a method for increasing mean corpuscular volume in a subject having functional iron deficiency, the method comprising administering to the subject an effective amount of a compound that stabilizes HIFα, thereby increasing mean corpuscular volume in the subject; a method for increasing mean corpuscular hemoglobin in a subject having functional iron deficiency, the method comprising administering to the subject an effective amount of a compound that stabilizes HIFα, thereby increasing mean corpuscular hemoglobin in the subject; a method for increasing serum iron in a subject having functional iron deficiency, the method comprising administering to the subject an effective amount of a compound that stabilizes HIFα, thereby increasing serum iron in the subject; and a method for increasing transferrin saturation in a subject having functional iron deficiency, the method comprising administering to the subject an effective amount of a compound that stabilizes HIFα, thereby increasing transferrin saturation in the subject.

In one aspect, the invention includes a method for overcoming or ameliorating the consequences of a cytokine-induced impairment of erythropoiesis in a subject, the method comprising administering to the subject an effective amount of a compound that stabilizes HIFα, thereby overcoming or ameliorating the consequences of the cytokine-induced impairment of erythropoiesis in the subject. In various aspects, the cytokine-induced impairment of erythropoiesis is suppression of EPO production; or impairment of iron metabolism. In any of the above-described methods, the cytokine is an inflammatory cytokine. In further embodiments, the cytokine is selected from the group consisting of TNF-α, IL-1β, and IFN-γ.

Methods for decreasing cytokine induction of VCAM-1 expression or/and E-selectin expression are also provided, the methods comprising administering to a subject in need an effective amount of a compound that stabilizes HIFα, thus decreasing cytokine induction of VCAM-1 expression or/and E-selectin expression.

In any of the above-described methods, the cytokine is an inflammatory cytokine. In further embodiments, the cytokine is selected from the group consisting of TNF-α, IL-1β, and IFN-γ.

Methods for treating or preventing a disorder associated with cytokine activity in a subject, wherein the disorder is selected from the group consisting of iron deficiency, functional iron deficiency, iron deficiency anemia, anemia of chronic disease, and micocytic anemia, are provided herein, the methods comprising administering to the subject an effective amount of a compound that stabilizes HIFα, thereby treating or preventing the disorder associated with cytokine activity. In any of the above-described methods, the cytokine is an inflammatory cytokine. In further embodiments, the cytokine is selected from the group consisting of TNF-α, IL-1β, and IFN-γ.

Methods for treating or preventing a disorder associated with cytokine activity in a subject, wherein the disorder is associated with a condition selected from the group consisting of an inflammation, an infection, an immunodeficiency, and a neoplastic disorder, the methods comprising administering to the subject an effective amount of a compound that stabilizes HIFα, thereby treating or preventing the disorder associated with cytokine activity, are also provided. In any of the above-described methods, the cytokine is an inflammatory cytokine. In further embodiments, the cytokine is selected from the group consisting of TNF-α, IL-1β, and IFN-γ.

In one aspect, the invention encompasses a method for increasing EPO production in the presence of a cytokine in a subject, the method comprising administering to the subject an effective amount of a compound that stabilizes HIFα, thereby increasing EPO production in the subject. A method for treating or preventing microcytosis in a subject, the method comprising administering to the subject an effective amount of a compound that stabilizes HIFα, thereby treating or preventing microcytosis in a subject, is also provided herein. In further aspects, the microcytosis is associated with a disorder selected from the group consisting of chronic disease, anemia of chronic disease, iron deficiency, functional iron deficiency, and anemia of iron deficiency. In any of the above-described methods, the cytokine is an inflammatory cytokine. In further embodiments, the cytokine is selected from the group consisting of TNF-α, IL-1β, and IFN-γ.

In any of the present methods for treating or preventing, it is contemplated that a compound of the invention can be administered as part of a combinatorial therapy, additionally comprising administration of another therapeutic agent, for example, EPO, iron, and vitamins, e.g., B vitamins, etc.

A kit, comprising a compound that stabilizes HIFα and at least one other supplement is provided herein. In one aspect, the supplement is selected from the group consisting of erythropoietin, iron, and B vitamins, is provided herein, as is a pharmaceutical composition comprising a compound that stabilizes HIFα and at least one supplement selected from the group consisting of erythropoietin, iron, and B vitamins.

The present invention provides compounds and methods for treating or preventing anemia of chronic disease, wherein the anemia of chronic disease is associated with increased cytokine levels. In particular, the invention provides methods and compounds for use in overcoming or ameliorating the consequences of cytokine-induced effects in a subject having increased cytokine levels, e.g., cytokine suppression of EPO production, cytokine-induced expression of various cell adhesion factors, etc.

In one embodiment, the invention provides methods and compounds for overcoming cytokine suppression of EPO production. These methods and compounds are useful in overcoming TNFα and/or IL-1β suppression of EPO production, as measured, e.g., by the ability to overcome TNFα and/or IL-1β suppression of EPO production in cultured Hep3B cells.

In one embodiment, the invention provides methods and compounds for reducing cytokine-induced increase in expression of various cell adhesion factors. The methods and compounds can be used to overcome TNFα, IL-1β, and IFN-γ-induced increases in expression of endothelial cell adhesion factors, e.g., VCAM-1 and E-selectin, as measured by, e.g., a decrease in expression level of VCAM-1 or E-selectin in endothelial cells (HUVEC, etc.).

The invention provides methods and compounds for treating or preventing iron deficiency in a subject. In particular, the present methods and compounds can be used to enhance iron metabolism, or to treat or prevent diseases and disorders associated with impaired iron metabolism, e.g., impaired iron uptake, storage, processing, transport, mobilization, and utilization, etc.

In one aspect, the methods and compounds modulate expression of factors involved in iron metabolism, e.g., transport, utilization, storage, etc. For example, the methods and compounds increase expression of transferrin receptor, as measured by, e.g., increased expression of transferrin receptor in liver cells (e.g., Hep3B, HepG2), kidney cells (e.g., HK-2), or lymphocytes (e.g., THP-1), or by increased soluble transferrin receptor levels in human subjects. The present methods and compounds increase ceruloplasmin gene expression, as measured, e.g., by increased gene expression in mouse kidney and in Hep3B cells. In one aspect, the invention provides methods and compounds that decrease hepcidin gene expression, for example, as measured by reduced gene expression of hepcidin in mouse liver. In a further aspect, methods and compounds of the present invention are used to increase expression of factors including NRAMP2, duodenal cytochrome b reductase 1, etc., as measured, e.g., by increased gene expression in mouse intestine. The present methods and compounds increase expression of 5-aminolevulinate synthase, the first enzyme in the heme synthetic pathway and rate-limiting enzyme for heme synthesis, as measured, e.g., by increased gene expression in mouse intestine.

The present methods and compounds can be used to enhance iron metabolism. In particular, the present methods and compounds enhance iron metabolism, as measured by, e.g., increased serum iron levels, increased percent transferrin saturation, and reduced microcytosis in a rat model of impaired iron metabolism.

The present invention provides methods and compounds for inducing enhanced erythropoiesis. In particular, the present methods and compounds enhance erythropoiesis, e.g., as measured by increases in reticulocyte count, hematocrit, and red blood cell count, in a rat model of impaired erythropoiesis and in human subjects, or as measured by, e.g., increased hemoglobin levels in a rat model of impaired erythropoiesis.

The present methods and compounds reduce microcytosis as measured, e.g., by increased mean corpuscular hemoglobin levels and increased mean corpuscular volume in a rat model of impaired erythropoiesis.

The present methods comprise administering to a subject an effective amount of a compound that stabilizes HIFα. Such stabilization can be through, e.g., inhibition of HIF hydroxylase activity. A preferred compound of the invention is a compound that inhibits HIF prolyl hydroxylase activity. The inhibition can be direct or indirect, can be competitive or non-competitive, etc. In various embodiments, a compound of the invention is selected from the group consisting of 2-oxoglutarate mimetics, iron chelators, and proline analogs. In one aspect, a 2-oxoglutarate mimetic is a heterocyclic carbonyl glycine of Formula I, Ia, or Ib. In another aspect, an iron chelator is a hydroxamic acid of Formula III. In particular embodiments, as exemplified herein, the compound is Compound D.

Exemplary compounds of the invention include [(1-Chloro-4-hydroxy-isoquinoline-3-carbonyl)-amino]-acetic acid (compound A), [(4-Hydroxy-7-phenoxy-isoquinoline-3-carbonyl)-amino]-acetic acid (compound B), [(4-Hydroxy-7-phenylsulfanyl-isoquinoline-3-carbonyl)-amino]-acetic acid (compound C), and 3-{[4-(3,3-Dibenzyl-ureido)-benzene sulfonyl]-[2-(4-methoxy-phenyl)-ethyl]-amino}-N-hydroxy-propionamide (compound D). Additional compounds according to the present invention and methods for identifying additional compounds of the present invention are provided, infra.

DESCRIPTION OF THE INVENTION

Figure 1A:
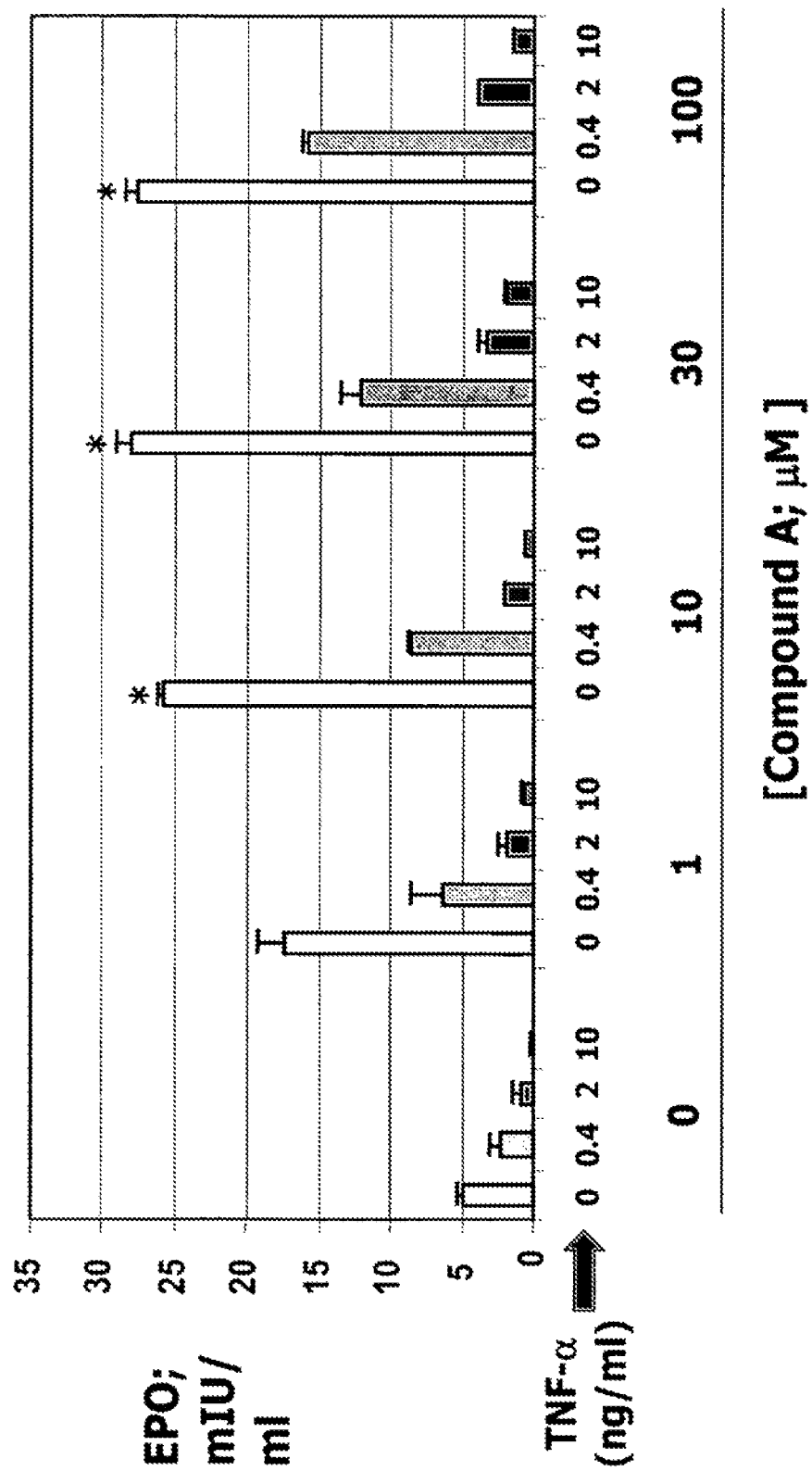
FIGS. 1A and 1B set forth data showing methods and compounds of the present invention overcome the suppressive effects of TNF-α on EPO production.
Figure 1B:
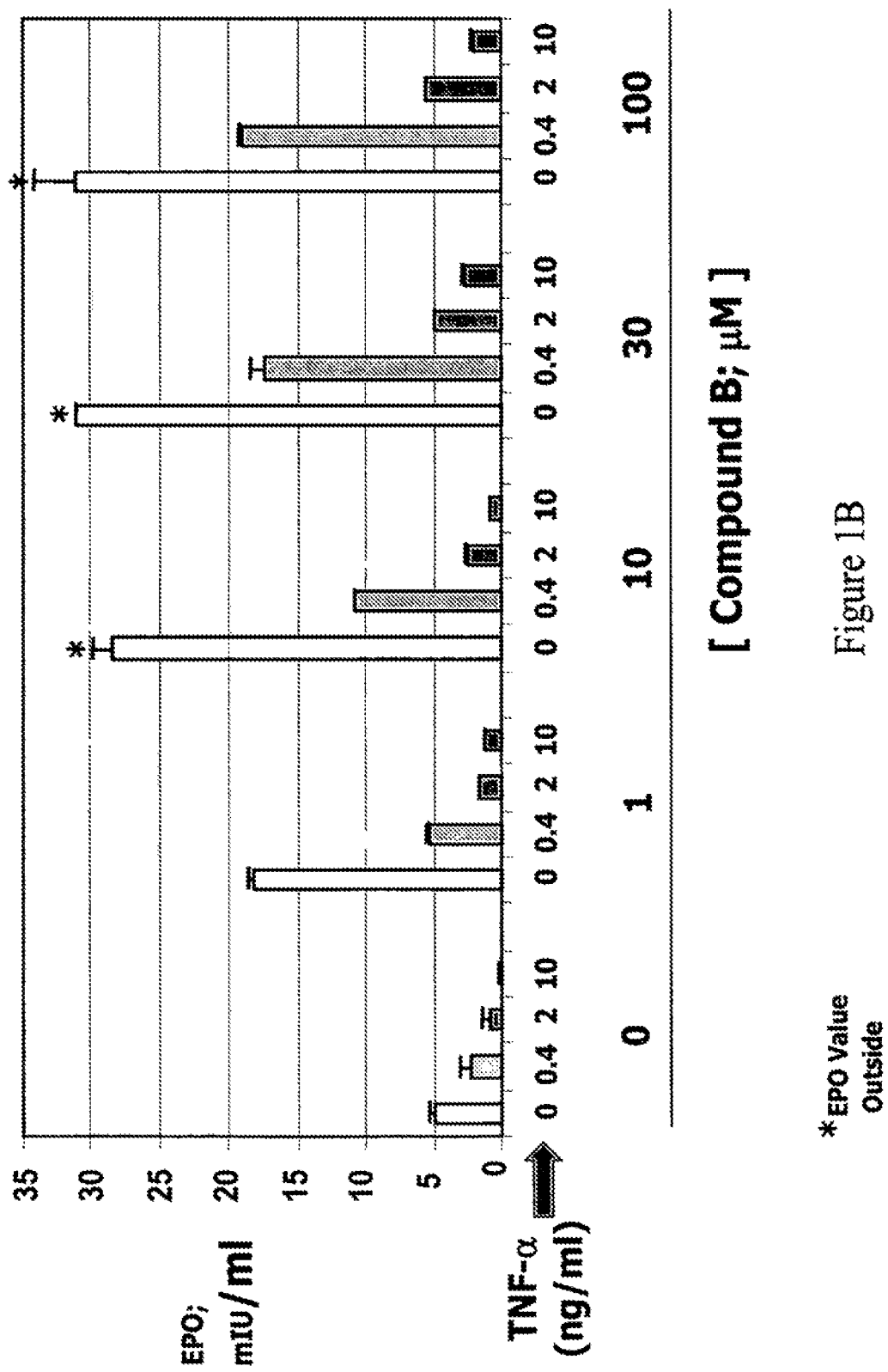

Before the present compositions and methods are described, it is to be understood that the invention is not limited to the particular methodologies, protocols, cell lines, assays, and reagents described, as these may vary. It is also to be understood that the terminology used herein is intended to describe particular embodiments of the present invention, and is in no way intended to limit the scope of the present invention as set forth in the appended claims.

It must be noted that as used herein and in the appended claims, the singular forms "a," "an," and "the" include plural references unless context clearly dictates otherwise. Thus, for example, a reference to "a fragment" includes a plurality of such fragments; a reference to a "compound" is a reference to one of more compounds and to equivalents thereof as described herein and ask known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

The practice of the present invention will employ, unless otherwise indicated, conventional methods of chemistry, biochemistry, molecular biology, cell biology, genetics, immunology and pharmacology, within the skill of the art. Such techniques are explained fully in the literature. See, e.g., Gennaro, A. R., ed. (1990) Remington's Pharmaceutical Sciences, 18th ed., Mack Publishing Co.; Hardman, J. G., Limbird, L. E., and Gilman, A. G., eds. (2001) The Pharmacological Basis of Therapeutics, 10th ed., McGraw-Hill Co.; Colowick, S. et al., eds., Methods In Enzymology, Academic Press, Inc.; Weir, D. M., and Blackwell, C. C., eds. (1986) Handbook of Experimental Immunology, Vols. I-IV, Blackwell Scientific Publications; Maniatis, T. et al., eds. (1989) Molecular Cloning: A Laboratory Manual, 2nd edition, Vols. I-III, Cold Spring Harbor Laboratory Press; Ausubel, F. M. et al., eds. (1999) Short Protocols in Molecular Biology, 4th edition, John Wiley & Sons; Ream et al., eds. (1998) Molecular Biology Techniques: An Intensive Laboratory Course, Academic Press; Newton, C. R., and Graham, A., eds. (1997) PCR (Introduction to Biotechniques Series), 2nd ed., Springer Verlag.

Definitions

The term "anemia of chronic disease" refers to any anemia that develops as a result of, e.g., extended infection, inflammation, neoplastic disorders, etc. The anemia which develops is often characterized by a shortened red blood cell life span and sequestration of iron in macrophages, which results in a decrease in the amount of iron available to make new red blood cells. Conditions associated with anemia of chronic disease include, but are not limited to, chronic bacterial endocarditis, osteomyelitis, rheumatic fever, ulcerative colitis, and neoplastic disorders. Further conditions include other diseases and disorders associated with infection, inflammation, and neoplasms, including, e.g., inflammatory infections (e.g., pulmonary abscess, tuberculosis, osteomyelitis, etc.), inflammatory noninfectious disorders (e.g., rheumatoid arthritis, systemic lupus erythrematosus, Crohn's disease, hepatitis, inflammatory bowel disease, etc.), and various cancers, tumors, and malignancies (e.g., carcinoma, sarcoma, lymphoma, etc.).

The terms "disorders" and "diseases" and "conditions" are used inclusively and refer to any condition deviating from normal.

The term "erythropoietin" refers to any recombinant or naturally occurring erythropoietin including, e.g., human erythropoietin (GenBank Accession No. AAA52400; Lin et al. (1985) Proc Natl Acad Sci USA 82:7580-7584), EPO-ETIN human recombinant erythropoietin (Amgen, Inc., Thousand Oaks Calif.), ARANESP human recombinant erythropoietin (Amgen), PROCRIT human recombinant erythropoietin (Ortho Biotech Products, L.P., Raritan N.J.), etc.

The term "HIFα" refers to the alpha subunit of hypoxia inducible factor protein. HIFα may be any human or other mammalian protein, or fragment thereof, including human HIF-1α (Genbank Accession No. Q16665), HIF-2α (Genbank Accession No. AAB41495), and HIF-3α (Genbank Accession No. AAD22668); murine HIF-1α (Genbank Accession No. Q61221), HIF-2α (Genbank Accession No. BAA20130 and AAB41496), and HIF-3a (Genbank Accession No. AAC72734); rat HIF-1α (Genbank Accession No. CAA70701), HIF-2α (Genbank Accession No. CAB96612), and HIF-3α (Genbank Accession No. CAB96611); and bovine HIF-1α (Genbank Accession No. BAA78675). HIFα may also be any non-mammalian protein or fragment thereof, including *Xenopus laevis* HIF-1α (Genbank Accession No. CAB96628), *Drosophila melanogaster* HIF-1α (Genbank Accession No. JC4851), and chicken HIF-1α (Genbank Accession No. BAA34234). HIFα gene sequences may also be obtained by routine cloning techniques, for example by using all or part of a HIFα gene sequence described above as a probe to recover and determine the sequence of a HIFα gene in another species.

Fragments of HIFα include the regions defined by human HIF-1α from amino acid 401 to 603 (Huang et al., supra), amino acid 531 to 575 (Jiang et al. (1997) J Biol Chem 272:19253-19260), amino acid 556 to 575 (Tanimoto et al., supra), amino acid 557 to 571 (Srinivas et al. (1999) Biochem Biophys Res Commun 260:557-561), and amino acid 556 to 575 (Ivan and Kaelin (2001) Science 292:464-468). Further, a fragment of HIFα includes any fragment containing at least one occurrence of the motif LXXLAP, e.g., as occurs in the HIFα native sequence at $L_{397}$TLLAP and L$_{559}$EMLAP. Additionally, a fragment of HIFα includes any fragment retaining at least one functional or structural characteristic of HIFα.

The terms "HIF prolyl hydroxylase" and "HIF PH" refer to any enzyme capable of hydroxylating a proline residue in the HIF protein. Preferably, the proline residue hydroxylated by HIF PH includes the proline found within the motif LXXLAP, e.g., as occurs in the human HIF-1α native sequence at L$_{397}$TLLAP and L$_{559}$EMLAP. HIF PH includes members of the Egl-Nine (EGLN) gene family described by Taylor (2001, Gene 275:125-132), and characterized by Aravind and Koonin (2001, Genome Biol 2:RESEARCH0007), Epstein et al. (2001, Cell 107:43-54), and Bruick and McKnight (2001, Science 294:1337-1340). Examples of HIF prolyl hydroxylase enzymes include human SM-20 (EGLN1) (GenBank Accession No. AAG33965; Dupuy et al. (2000) Genomics 69:348-54), EGLN2 isoform 1 (GenBank Accession No. CAC42510; Taylor, supra), EGLN2 isoform 2 (GenBank Accession No. NP_060025), and EGLN3 (GenBank Accession No. CAC42511; Taylor, supra); mouse EGLN1 (GenBank Accession No. CAC42515), EGLN2 (GenBank Accession No. CAC42511), and EGLN3 (SM-20) (GenBank Accession No. CAC42517); and rat SM-20 (GenBank Accession No. AAA19321). Additionally, HIF PH may include *Caenorhabditis elegans* EGL-9 (GenBank Accession No. AAD56365) and *Drosophila melanogaster* CG1114 gene product (GenBank Accession No. AAF52050). HIF prolyl hydroxylase also includes any fragment of the foregoing full-length proteins that retain at least one structural or functional characteristic.

The term "prolyl hydroxylase inhibitor" or "PHI," as used herein, refers to any compound that reduces or otherwise modulates the activity of an enzyme that hydroxylates amino acid residues. Although enzymatic activity wherein proline residues are hydroxylated is preferred, hydroxylation of other amino acids including, but not limited to, arginine, is also contemplated. Compounds that can be used in the methods of the invention include, for example, iron chelators, 2-oxoglutarate mimetics, and modified amino acid, e.g., proline, analogs.

In particular embodiments, the present invention provides for use of structural mimetics of 2-oxoglutarate. Such compounds may inhibit the target 2-oxoglutarate dioxygenase enzyme family member competitively with respect to 2-oxoglutarate and noncompetitively with respect to iron. (Majamaa et al. (1984) Eur J Biochem 138:239-245; and Majamaa et al. (1985) Biochem J 229:127-133.) PHIs specifically contemplated for use in the present methods are described, e.g., in Majamaa et al., supra; Kivirikko and Myllyharju (1998) Matrix Biol 16:357-368; Bickel et al. (1998) Hepatology 28:404-411; Friedman et al. (2000) Proc Natl Acad Sci USA 97:4736-4741; Franklin (1991) Biochem Soc Trans 19):812 815; Franklin et al. (2001) Biochem J 353:333-338; and International Publication Nos. WO 03/053977 and WO 03/049686, each incorporated by reference herein in its entirety. Exemplary PHIs, including [(1-Chloro-4-hydroxy-isoquinoline-3-carbonyl)-amino]-acetic acid (compound A), [(4-Hydroxy-7-phenoxy-isoquinoline-3-carbonyl)-amino]-acetic acid (compound B), [(4-Hydroxy-7-phenylsulfanyl-isoquinoline-3-carbonyl)-amino]-acetic acid (compound C), and 3-{[4-(3,3-Dibenzyl-ureido)-benzenesulfonyl]-[2-(4-methoxy-phenyl)-ethyl]-amino}-N-hydroxy-propionamide (compound D) are used in the present examples to demonstrate the methods of the invention described herein.

Invention

The present invention relates to methods and compounds for inducing enhanced or complete erythropoiesis in a subject. In particular, the methods comprise inducing enhanced or complete erythropoiesis by stabilizing HIFα in a subject. Methods of inducing enhanced erythropoiesis by inhibiting HIF prolyl hydroxylase are specifically contemplated. In specific embodiments, the methods comprise administering to a subject a compound of the invention. In various embodiments, the subject can be a cell, tissue, organ, organ system, or whole organism.

Anemia of chronic disease is the most common form of anemia in hospitalized patients. Anemia of chronic disease occurs in patients having inflammatory or malignant disorders, including inflammatory infections (e.g., pulmonary abscess, tuberculosis, osteomyelitis, etc.), inflammatory noninfectious disorders (e.g., rheumatoid arthritis, systemic lupus erythrematosus, Crohn's disease, hepatitis, inflammatory bowel disease, etc.), and various cancers, tumors, and malignancies (e.g., carcinoma, sarcoma, lymphoma, etc.), chronic bacterial endocarditis, osteomyelitis, rheumatic fever, ulcerative colitis, and neoplastic disorders.

In one aspect, the invention provides methods for inducing enhanced or complete erythropoiesis to treat anemia of chronic disease. Anemia of chronic disease is associated with numerous chronic disorders, including, for example, rheumatoid arthritis, rheumatic fever, inflammatory bowel disease, ulcerative colitis, systemic lupus erythematosus, vasculitis, neoplastic disorders, etc., as well as chronic infection and chronic inflammation. Reduced or ineffective erythropoiesis is a common pathology in patients with anemia of chronic disease. Reduced or ineffective erythropoiesis can result from various metabolic abnormalities in the erythropoietic pathway, including, for example, suppressed EPO production, decreased EPO responsiveness in the bone marrow, and abnormal iron processing, including, for example, abnormal or ineffective iron uptake, mobilization, storage, and absorption.

A physiological feature of disorders associated with anemia of chronic disease is increased production of inflammatory cytokines (Means (1995) Stem Cells 13:32-37 and Means (1999) Int J Hematol 70:7-12.), including, for example, tumor necrosis factor-α (TNF-α), interleukin-1β (IL-1β), and interferon-γ (IFN-γ), which negatively affect the ability to mediate EPO production, EPO responsiveness, and the coordinate regulation of iron metabolism. (See, e.g., Roodman et al. (1989) Adv Exp Med Biol 271:185-196; Fuchs et al. (1991) Eur J Hematol 46:65-70; Jelkmann et al. (1991) Ann NY Acad Sci 718:300-311; Vannucchi et al. (1994) Br J Hematol 87:18-23; and Oldenburg et al. (2001) Aliment Pharmacol Ther 15:429-438.) The present invention provides methods for improving metabolic and physiologic pathways related to EPO production, EPO signaling, and iron utilization, resulting in complete or enhanced erythropoiesis and reduction or amelioration of anemia of chronic disease.

The present invention provides advantages over existing therapies for anemia of chronic disease, such as, for example, recombinant EPO administration. Reduced EPO production is only one aspect of decreased erythropoiesis and it is recognized that administration of recombinant EPO does not address other deficiencies associated with reduced erythropoiesis that exist in patients with anemia of chronic disease. (See, e.g., Clibon et al. (1990) Exp Hematol 18:438-441 and Macdougall and Cooper (2002) Neprol Dial Transplant 17(11):39-43.) These deficiencies include, for example, reduced EPO responsiveness of the bone marrow, as well as numerous aspects of iron metabolism that contribute to complete or total erythropoiesis, including iron absorption from the gut, trans-enterocyte transport, oxidation of iron to the ferric state by hephaestin or ceruloplasmin, binding and uptake of iron by transferrin and transferrin receptor, and iron transport to the marrow where iron utilization occurs, including heme synthesis. Many patients are refractory to administration of recombinant EPO for the reasons described above, in which responses to recombinant EPO administration are reduced or absent, even at high doses of recombinant EPO.

The prevalence of inflammatory cytokines in anemia of chronic disease leads to, e.g., decreased serum iron levels and increased iron storage, primarily in macrophages, within a cell compartment not readily accessible to emerging erythroid progenitors, which require iron for appropriate heme synthesis. The invention provides methods for enhancing the metabolic pathways contributing to complete and total erythropoiesis. In one embodiment, the therapeutic is administered in combination with supplements that further enhance its efficacy, e.g. iron and B vitamins.

Anemia of chronic disease is associated with increased levels of ferritin. Despite high levels of ferritin, subjects with anemia of chronic disease are not able to utilize iron effectively. High levels of ferritin are indicative of reduced iron recycling to the marrow and enhanced iron storage, a functional iron deficiency often associated with anemia of chronic disease and a pseudo-inflammatory state often existing in uremic chronic kidney disease patients. By decreasing ferritin levels, methods and compounds of the present invention decrease stored iron and enhance iron recycling through transferrin and transferrin receptor. Reduced serum ferritin levels would be indicative of enhanced iron utilization and enhanced iron recycling to the marrow, thus increasing iron availability for heme production and erythropoiesis.

The genomic response to hypoxia includes changes in gene expression and cell physiology to ameliorate the acute and chronic effects of oxygen deprivation. Hypoxia inducible factor (HIF) is a transcription factor composed of an oxygen-regulated alpha subunit (HIFα) and a constitutively expressed beta subunit (HIFβ). HIFα is destabilized in normoxic environments due to hydroxylation of specific proline residues by HIF-specific proline hydroxylases (HIF-PHs). However, when oxygen becomes limiting, e.g., in hypoxic environments, HIF-PH cannot hydroxylate HIFα, the subunit is not degraded, and active HIF complexes form, translocate to the nucleus, and activate gene transcription.

In certain aspects, the present invention provides methods treating anemia of chronic disease by pharmaceutically mimicking hypoxia. In certain aspects, the methods enhance EPO production in a manner that is resistant to the suppressive effects of inflammatory cytokines. EPO production is normally induced by hypoxia or low oxygen but expression and secretion remain depressed in the presence of inflammatory cytokines, such as TNF-α, IL-1β, and IFN-γ, prevalent in chronic disease patients. (See, e.g., Means (1995) Stem Cells 13:32-37; Means (1999) Int J Hematol 70:7-12; Roodman et al. (1989) Adv Exp Med Biol 271:185-196; Fuchs et al. (1991) Eur J Hematol 46:65-70; Jelkmann et al. (1991) Ann NY Acad Sci 718:300-311; and Vannucchi et al. (1994) Br J Hematol 87:18-23.) Prolyl hydroxylase inhibitors overcome the suppressive effects of inflammatory cytokines on EPO production, at least in part, as evidenced by the capacity of Hep3B cells to secrete EPO to levels above that observed in the presence of inflammatory cytokines. (See, e.g., FIGS. 1A, 1B, 2A, 2B, 3A, 3B, 4A, and 4B.)

Agents such as the iron chelator, desferrioxamine, have also shown some efficacy in studies of erythropoietin-resistant anemia, e.g., anemia of chronic disease. (See, e.g., Salvarani et al. (1996) Rheumatol Int 16:45-48 and Goch et al. (1995) Eur J Hematol 55:73-77.)

In other aspects, the present invention provides methods for improved signaling by the EPO receptor in the presence of inflammatory cytokines. The prevalence of inflammatory cytokines in chronic disease patients results in reduced efficacy of EPO signaling, evidenced by the inability of many patients to respond to recombinant EPO with enhanced erythropoiesis. This is thought to occur by a decreased sensitivity to EPO bioactivity, as well as defects in bone marrow architecture and/or microenvironment. (See, e.g., Clibon et al. (1990) Exp Hematol 18:438-441 and Macdougall and Cooper (2002) Neprol Dial Transplant 17(11):39-43.) In certain embodiments, the present invention provides methods for inducing total and complete erythropoiesis by restoring the sensitivity of appropriate cells to signal transduction through the EPO receptor.

Iron deficiency is one of the most common nutritional deficiencies worldwide and is the leading cause of anemia on a global basis. Iron balance is fundamentally regulated by the rate of erythropoiesis and the size of iron stores. Iron deficiency can occur with or without anemia, and has been associated with impaired cognitive development.

Iron deficiency is defined as inadequate iron supply (levels or stores) or as inadequate availability or utilization of iron in the body. This can be due to nutritional deficiencies, e.g., lack of iron in the diet; to iron malabsorption, due, for example, to surgery (post-gastrectomy) or disease (Crohn's disease); or to a depletion in iron supply or increased iron loss due to chronic or acute blood loss resulting from injury or trauma, menses, blood donation, phlebotomy (such as due to various procedures, surgeries); from increased iron demand, e.g., due to rapid growth in infancy or adolescence, pregnancy, erythropoietin therapy, etc.

Iron deficiency can also be functional iron deficiency, e.g., iron deficiency characterized by the subject's impaired ability to access and utilize iron stores. Iron is not available at a rate sufficient to allow normal hemoglobinization of erythrocytes, leading to reduced reticulocyte and erythrocyte cellular hemoglobin content. Functional iron deficiency is often seen in healthy individuals with apparently normal or even increased iron stores but with impaired iron availability, as measured, e.g., by low levels of percent transferrin saturation. This type of iron deficiency is frequently associated with acute or with chronic inflammation.

Iron deficiency of any kind can lead to iron-deficient or iron-restricted erythropoiesis, in which red blood cell numbers decrease and circulating red blood cells are smaller than normal (microcytic) and lack adequate hemoglobin, and as such are pale in color (hypochromic).

Subjects with iron deficiency, including functional iron deficiency, can develop impaired hemoglobin synthesis, reduced % transferrin saturation, and decreased hemoglobin and hematocrit levels, leading to iron deficiency anemia. Iron deficiency anemia is the most common anemia in the world. Iron is an essential component of hemoglobin; without iron, the marrow is unable to produce hemoglobin effectively. Iron deficiency anemia may occur in subjects with depleted or impaired iron supply, or may occur in subjects having functional iron deficiency, when iron is present in storage but is unavailable, e.g., for hemoglobin production.

Iron metabolism encompasses in general the processes by which a cell, tissue, organ, organ system, or whole organism maintains iron homeostasis by altering, e.g., increasing or decreasing, specific processes of iron metabolism. Iron metabolism or iron metabolic processes encompass processes involving iron processing, transport, uptake, utilization, storage, mobilization, absorption, etc. Specific aspects of iron metabolism and processing include expression of iron transporters and enzymes which facilitate movement of iron across a cell membrane and retention or secretion of iron by a cell; alteration in expression of proteins involved in iron transport in blood; alteration in expression of transferrin and transferrin receptors; alteration in expression and/or activity of proteins involved in iron absorption; alteration in expression and activity of iron associated transcriptional and translational regulatory proteins; and alteration of iron distribution within body or culture fluids, including, e.g., interstitial (i.e. extracellular), intracellular, blood, bone marrow, and the like.

In certain aspects, the present invention provides methods for improving iron uptake, transport, processing, and utilization. Anemia of chronic disease is associated with defects in iron utilization that negatively affect heme synthesis and hemoglobin formation, resulting in reduced erythropoiesis. (See, e.g., Oldenburg et al. (2001) Aliment Pharmacol Ther 15:429-438.) Decreased serum iron levels, iron mobilization, and any associated increases in iron storage in chronic disease patients, may relate to a microbial defense mechanism of macrophage under conditions of long-lasting inflammation. (See, Fuchs et al. (1991) Eur J Hematol 46:65-70.) In some aspects, the present invention provides methods for increasing effective metabolism of iron by stabilizing HIFα.

Numerous proteins mediate iron metabolism, including proteins such as erythroid 5-aminolevulinate acid synthase (ALAS) (the first and rate-limiting step in heme synthesis) (Bottomley and Muller-Eberhard (1988) Semin Hematol 25:282-302 and Yin et al. (1998) Blood, Cells, Molecules, and Diseases 24(3):41-533), transferrin, transferrin receptor, iron transporters (involved in iron transport), ceruloplasmin, etc. Increases in transferrin and transferrin receptor expression stimulate iron uptake by erythroid progenitors and facilitate iron uptake and transport to marrow by macrophage (Goswami et al. (2002) Biochem Cell Biol 80:679-689.). Ceruloplasmin increases the oxidation of ferrous iron to ferric so that binding to transferrin occurs (Goswami et al. (2002) Biochem Cell Biol 80:679-689.). In certain aspects, methods of the present invention increase iron metabolism by increasing expression or activity of proteins involved in iron metabolism, including erythroid 5-aminolevulinate synthase, transferrin, transferrin receptor, NRAMP2, sproutin (duodenal cytochrome b reductase 1), and ceruloplasmin. In other aspects, methods of the present invention increase iron metabolism by decreasing expression or activity hepcidin and by modulating expression of ferritin.

In one embodiment, the invention provides methods and compounds for increasing expression of genes whose products are involved in iron metabolism and processing, including iron uptake, storage, transport, absorption, etc. Such genes include, but are not limited to, transferrin receptor, ceruloplasmin, NRAMP2, 5-aminolevulinate synthase, sproutin (CYBRD1), etc. Therapeutic upregulation of genes involved in iron metabolism and processing will effectively increase iron availability and, thereby, produce a beneficial effect in patients with anemia of chronic disease, anemia of iron deficiency, functional iron deficiency, etc. In another embodiment, the invention provides methods and compounds for decreasing expression of hepcidin, a protein associated with iron regulation.

Proper iron metabolism is regulated, in part, by iron response-element binding proteins (IRPs), which bind to iron-responsive elements (IREs) found in the 5'- and/or 3'-UTRs of mRNAs encoding, e.g., ferritin (iron storage), mitochondrial aconitase (energy metabolism), erythroid-aminolevulinate synthase, and transferrin receptor. IRP binding to a 5'-IRE, as occurs, e.g., in the ferritin transcript, inhibits translation of the mRNA; whereas binding to a 3'-IRE, as occurs in, e.g., the transferrin transcript, protects the mRNA from degradation. IRP-2 is made constitutively within cells, but is degraded and thus inactivated under iron-replete conditions. IRP-2 is stabilized, however, under iron deplete and/or hypoxic conditions (Hanson et al. (1999) J Biol Chem 274:5047-5052.). As IRP-2 decreases expression of ferritin, which is responsible for long-term storage of iron, and increases expression of transferrin and transferrin receptor, IRP-2 facilitates iron uptake, transport, and utilization, thus enhancing erythropoiesis (Klausner et al. (1993) Cell 72:19-28.). Recently, IREs have been described in other genes that are also necessary for erythropoiesis, including 5-aminolevulinate synthase, the NRAMP2 iron transporter (also known as Slc11a2, DCT1, DMT1, mk (microcytic anemia gene locus in mouse)), and the iron transporter that mediates iron absorption from dietary sources in the duodenum (Haile (1999) Am J Med Sci 318:230-240 and Gunshin et al. (2001) FEBS Lett 509:309-316.).

The methods of the present invention, by mimicking conditions of hypoxia, potentially stabilize IRP-2 in addition to HIFα, thus producing a synergistic effect involving both endogenous EPO production and enhanced iron uptake, transport, and utilization in the production of functional erythrocytes.

Among adults, iron absorption of dietary iron averages approximately 6% for men and 13% for non-pregnant women. NRAMP2 (also known as DMT1, DCT1, slc11a2) is a ubiquitously expressed divalent metal transporter involved in transmembrane transport of non-transferrin bound iron. NRAMP2 is an iron transport protein associated with iron transport from gastrointestinal lumen into duodenal enterocytes and from erythroblast endosomes to cytoplasm. In animals experiencing dietary iron starvation, NRAMP2 (slc11a2) expression was dramatically increased in the apical pole of enterocytes in the columnar absorptive epithelium of the proximal duodenum. (See, e.g., Canonne-Hergaux et al. (1999) Blood 93:4406-4417.) Genetic rodent models have linked this gene with anemias associated with iron deficiency, including hypochromic and microcytic anemic mice (mk mice) having a mutated NRAMP2 gene. MK mice exhibit severe defects in iron absorption and erythroid iron utilization.

In certain aspects, methods and compounds of the present invention are useful for increasing iron absorption of dietary iron. The present invention provides methods and compounds for increasing expression of genes associated with iron transport absorption. In particular, compounds of the present invention were effective at increasing expression of NRAMP2 in intestine. Increased NRAMP2 (slc11a2) expression would be desirable for increasing iron absorption of iron, e.g., dietary iron, from the gut.

In addition, the present invention provides data showing increased sproutin gene expression in the intestine of animals treated with a compound of the present invention. Sproutin intestinal iron reductase, also known as Dcytb and Cybrd1 (CYBRD1, duodenal cytochrome b reductase 1), is a ferric reductase, and catalyzes the reduction of extracellular ferric to ferrous iron associated with iron absorption. Sproutin is co-expressed with NRAMP2 in iron-starved animals in the apical region of duodenal villi (See, e.g., McKie et al. (2001) Science 291:1755-1759.)

Methods and compounds of the present invention are useful for increasing ceruloplasmin gene expression. Ceruloplasmin, also known as a ferroxidase-1, converts reduced iron released from storage sites (such as ferritin) to the oxidized form. Oxidized iron is able to bind to its plasma transport protein, transferrin. Ceruloplasmin deficiencies are associated with accumulation of iron in liver and other tissues. Evidence indicates that ceruloplasmin promotes efflux of iron from the liver and promotes influx of iron into iron-deficient cells. (See, e.g., Tran et al. (2002) J Nutr 132:351-356.)

Compounds of the present invention reduced expression of hepcidin mRNA in mouse liver. Inflammation leads to IL-6 production, which acts on hepatocytes to induce hepcidin production. Hepcidin inhibits macrophage iron release and intestinal iron absorption, reducing iron availability and leading to, for example, hypoferremia. Decreased hepcidin expression is associated with increased iron release from reticuloendothelial cells and increased intestinal iron absorption. Therefore, methods and compounds of the present invention are useful for decreasing hepcidin expression, increasing intestinal iron absorption, and reducing hypoferremia.

Methods for treating anemia associated with hepatitis C virus (HCV) infection are specifically contemplated. Current therapy for HCV infection include interferon-α and ribavirin in combination. This combination therapy is associated with decreases in hemoglobin concentrations and anemia. In one aspect, methods and compounds are provided for treating anemia associated with HCV infection. In another aspect, methods and compounds for treating anemia associated with interferon-α therapy for HCV infection are provided. In another aspect, the present invention provides compounds and methods useful for treating anemia associated with ribavirin therapy for HCV infection.

Methods for increasing the production of factors required for differentiation of erythrocytes from hematopoietic progenitor cells including, e.g., hematopoietic stem cells (HSCs), CFU-GEMM (colony-forming-unit-granulocyte/erythroid/monocyte/megakaryocyte) cells, etc., are also contemplated. Factors that stimulate erythropoiesis include, but are not limited to, erythropoietin. In another aspect, the methods increase the production of factors required for iron uptake, transport, and utilization. Such factors include, but are not limited to, erythroid aminolevulinate synthase, transferrin, transferrin receptor, ceruloplasmin, ferritin, etc. In yet another aspect, the method increases factors required for differentiation of erythrocytes and additionally factors required for iron uptake, transport, and utilization.

Methods for enhancing responsiveness of hematopoietic precursors to erythropoietin are also contemplated. As described above, such precursors include HSCs, CFU-GEMMs, etc. The responsiveness of the precursor cells can be augmented, e.g., by altering expression of erythropoietin receptors, intracellular factors involved in erythropoietin signaling, and secreted factors that facilitate interaction of erythropoietin with the receptors. The present invention provides methods for enhancing EPO responsiveness of the bone marrow, for example, by increasing EPO receptor expression.

Methods

Various methods are provided herein. In one aspect, the methods comprise administering to a subject an agent that stabilizes HIFα.

Stabilization of HIFα can be accomplished by any of the methods available to and known by those of skill in the art, and can involve use of any agent that interacts with, binds to, or modifies HIFα or factors that interact with HIFα, including, e.g., enzymes for which HIFα is a substrate. In certain aspects, the present invention contemplates providing a constitutively stable HIFα variant, e.g., stable HIF muteins, etc, or a polynucleotide encoding such a variant. (See, e.g., U.S. Pat. Nos. 6,562,799 and 6,124,131; and 6,432,927.) In other aspects, the present invention contemplates that stabilizing HIFα comprises administering an agent that stabilizes HIFα. The agent can be composed of polynucleotides, e.g. antisense sequences (see, e.g., International Publication No. WO 03/045440); polypeptides; antibodies; other proteins; carbohydrates; fats; lipids; and organic and inorganic substances, e.g., small molecules, etc. In a preferred embodiment, the present invention contemplates stabilizing HIFα, e.g., in a subject, by administering to the subject an agent that stabilizes HIFα wherein the agent is a compound, e.g., small molecule compound, etc., that stabilizes HIFα.

In other embodiments, the methods of the invention comprise stabilizing HIFα by inhibiting the activity of at least one enzyme selected from 2-oxoglutarate dioxygenase family. In a preferred embodiment, the enzyme is a HIF hydroxylase enzyme, e.g., EGLN-1, EGLN-2, EGLN-3, etc. (See, e.g., Taylor (2001) Gene 275:125-132; Epstein et al. (2001) Cell 107:43-54; and Bruick and McKnight (2001) Science 294:1337-1340.) It is specifically contemplated, however, that the enzyme be any enzyme selected from the 2-oxoglutarate dioxygenase enzyme family, including, for example, procollagen lysyl hydroxylase, procollagen prolyl 3-hydroxylase, procollagen prolyl 4-hydroxylase α(I) and α(II), thymine 7-hydroxylase, aspartyl (asparaginyl) β-hydroxylase, ε-N-trimethyllysine hydroxylase, and γ-butyrobetaine hydroxylase, etc. (See, e.g., Majamaa et al. (1985) Biochem J 229:127-133; Myllyharju and Kivirikko (1997) EMBO J 16:1173-1180; Thornburg et al. (1993) 32:14023-14033; and Jia et al. (1994) Proc Natl Acad Sci USA 91:7227-7231.)

In certain embodiments, the methods comprise treating anemia of chronic disease or regulating iron metabolism by administering to a subject an effective amount of an agent that stabilizes HIFα. In preferred embodiments, the agent is a compound of the present invention. In one aspect, the compound stabilizes HIFα by inhibiting the hydroxylation of certain residues of HIFα, e.g., proline residues, asparagine residues, etc. In a preferred embodiment, the residues are proline residues. In specific embodiments, the residues can be the $P_{564}$ residue in HIF-1α or a homologous proline in another HIFα isoform, or the $P_{402}$ residue in HIF-1α or a homologous proline in another HIFα isoform, etc. In other embodiments, the present methods may encompass inhibiting hydroxylation of HIFα asparagine residues, e.g., the $N_{803}$ residue of HIF-1α or a homologous asparagine residue in another HIFα isoform.

Compounds

In preferred methods, the present methods comprise administering to a subject an effective amount of a compound that stabilizes HIFα. Exemplary compounds are disclosed in, e.g., International Publication No. WO 03/049686 and International Publication No. WO 03/053997, incorporated herein by reference in their entireties. Specifically, compounds of the invention include the following.

In certain embodiments, a compound of the invention is a compound that inhibits HIF hydroxylase activity. In various embodiments, the activity is due to a HIF prolyl hydroxylase, such as, for example, EGLN1, EGLN2, or EGLN3, etc. In other embodiments, the activity is due to a HIF asparaginyl hydroxylase, such as, for example, including, but not limited to, FIH. A preferred compound of the invention is a compound that inhibits HIF prolyl hydroxylase activity. The inhibition can be direct or indirect, can be competitive or non-competitive, etc.

In one aspect, a compound of the invention is any compound that inhibits or otherwise modulates the activity of a 2-oxoglutarate dioxygenase enzyme. 2-oxoglutarate dioxygenase enzymes include, but are not limited to, hydroxylase enzymes. Hydroxylase enzymes hydroxylate target substrate residues and include, for example, prolyl, lysyl, asparaginyl (asparagyl, aspartyl) hydroxylases, etc. Hydroxylases are sometimes described by target substrate, e.g., HIF hydroxylases, procollagen hydroxylases, etc., and/or by targeted residues within the substrate, e.g., prolyl hydroxylases, lysyl hydroxylases, etc., or by both, e.g., HIF prolyl hydroxylases, procollagen prolyl hydroxylases, etc. Representative 2-oxoglutarate dioxygenase enzymes include, but are not limited to, HIF hydroxylases, including HIF prolyl hydroxylases, e.g., EGLN1, EGLN2, and EGLN3, HIF asparaginyl hydroxylases, e.g., factor inhibiting HIF (FIH), etc.; procollagen hydroxylases, e.g., procollagen lysyl hydroxylases, procollagen prolyl hydroxylases, e.g., procollagen prolyl 3-hydroxylase, procollagen prolyl 4-hydroxylase α(I) and α(II), etc.; thymine 7-hydroxylase; aspartyl (asparaginyl) β-hydroxylase; ε-N-trimethyllysine hydroxylase; γ-butyrobetaine hydroxylase, etc. Although enzymatic activity can include any activity associated with any 2-oxoglutarate dioxygenase, the hydroxylation of amino acid residues within a substrate is specifically contemplated. Although hydroxylation of proline and/or asparagine residues within a substrate is specifically included, hydroxylation of other amino acids is also contemplated.

In one aspect, a compound of the invention that shows inhibitory activity toward one or more 2-oxoglutarate dioxygenase enzyme may also show inhibitory activity toward one or more additional 2-oxoglutarate dioxygenase enzymes, e.g., a compound that inhibits the activity of a HIF hydroxylase may additionally inhibit the activity of a collagen prolyl hydroxylase, a compound that inhibits the activity of a HIF prolyl hydroxylase may additionally inhibit the activity of a HIF asparaginyl hydroxylase, etc.

As HIFα is modified by proline hydroxylation, a reaction requiring oxygen and Fe', the present invention contemplates in one aspect that the enzyme responsible for HIFα hydroxylation is a member of the 2-oxoglutarate dioxygenase family. Such enzymes include, but are not limited to, procollagen lysyl hydroxylase, procollagen prolyl 3-hydroxylase, procollagen prolyl 4-hydroxylase α(I) and α(II), thymine 7-hydroxylase, aspartyl (asparaginyl) β-hydroxylase, ε-N-trimethyllysine hydroxylase, and γ-butyrobetaine hydroxylase, etc. These enzymes require oxygen, $Fe^{2+}$, 2-oxoglutarate, and ascorbic acid for their hydroxylase activity. (See, e.g., Majamaa et al. (1985) Biochem J 229: 127-133; Myllyharju and Kivirikko (1997) EMBO J 16:1173-1180; Thornburg et al. (1993) 32:14023-14033; and Jia et al. (1994) Proc Natl Acad Sci USA 91:7227-7231.)

In one aspect, a compound of the invention is a compound that stabilizes HIFα. Preferably, the compound stabilizes HIFα through inhibition of HIF hydroxylase activity. It is thus specifically contemplated that a compound of the invention be selected from previously identified modulators of hydroxylase activity. For example, small molecule inhibitors of prolyl 4-hydroxylase have been identified. (See, e.g., Majamaa et al. (1984) Eur J Biochem 138:239-245; Majamaa et al. (1985) Biochem J 229:127-133; Kivirikko and Myllyharju (1998) Matrix Biol 16:357-368; Bickel et al. (1998) Hepatology 28:404-411; Friedman et al. (2000) Proc Natl Acad Sci USA 97:4736-4741; and Franklin et al. (2001) Biochem J 353:333-338; all incorporated by reference herein in their entirety.) The present invention contemplates the use of these compounds in the methods provided herein.

In some aspects, compounds of the present invention include, for example, structural mimetics of 2-oxoglutarate. Such compounds may inhibit the target 2-oxoglutarate dioxygenase enzyme family member competitively with respect to 2-oxoglutarate and noncompetitively with respect to iron. (Majamaa et al. (1984) Eur J Biochem 138:239-245; and Majamaa et al. Biochem J 229:127-133.)

In certain embodiments, compounds used in the methods of the invention are selected from a compound of the formula (I)

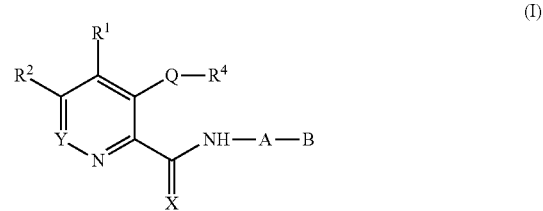

wherein
A is 1,2-arylidene, 1,3-arylidene, 1,4-arylidene; or $(C_1-C_4)$-alkylene, optionally substituted by one or two halogen, cyano, nitro, trifluoromethyl, $(C_1-C_6)$-alkyl, $(C_1-C_6)$-hydroxyalkyl, $(C_1-C_6)$-alkoxy, $-O-[CH_2]_x-C_fH_{(2f+1-g)}$ $Hal_g$, $(C_1-C_6)$-fluoroalkoxy, $(C_1-C_8)$-fluoroalkenyloxy, $(C_1-C_8)$-fluoroalkynyloxy, $-OCF_2Cl$, $-O-CF_2-CHFCl$; $(C_1-C_6)$-alkylmercapto, $(C_1-C_6)$-alkylsulfinyl, $(C_1-C_6)$-alkylsulfonyl, $(C_1-C_6)$-alkylcarbonyl, $(C_1-C_6)$-alkoxycarbonyl, carbamoyl, $N-(C_1-C_4)$-alkylcarbamoyl, $N,N$-di-$(C_1-C_4)$-alkylcarbamoyl, $(C_1-C_6)$-alkylcarbonyloxy, $(C_3-C_8)$-cycloalkyl, phenyl, benzyl, phenoxy, benzyloxy, anilino, N-methylanilino, phenylmercapto, phenylsulfonyl, phenylsulfinyl, sulfamoyl, $N-(C_1-C_4)$-alkylsulfamoyl, $N,N$-di-$(C_1-C_4)$-alkylsulfamoyl; or by a substituted $(C_6-C_{12})$-aryloxy, $(C_7-C_{11})$-aralkyloxy, $(C_6-C_{12})$-aryl, $(C_7-C_{11})$-aralkyl radical, which carries in the aryl moiety one to five identical or different substituents selected from halogen, cyano, nitro, trifluoromethyl, $(C_1-C_6)$-alkyl, $(C_1-C_6)$-alkoxy, $-O-[CH_2]_x-C_fH_{(2f+1-g)}Hal_g$, $-OCF_2Cl$, $-O-CF_2-CHFCl$, $(C_1-C_6)$-alkylmercapto, $(C_1-C_6)$-alkylsulfinyl, $(C_1-C_6)$-alkylsulfonyl, $(C_1-C_6)$-alkylcarbonyl, $(C_1-C_6)$-alkoxycarbonyl, carbamoyl, $N-(C_1-C_4)$-alkylcarbamoyl, $N,N$-di-$(C_1-C_4)$-alkylcarbamoyl, $(C_1-C_6)$-alkylcarbonyloxy, $(C_3-C_8)$-cycloalkyl, sulfamoyl, $N-(C_1-C_4)$-alkylsulfamoyl, $N,N$-di-$(C_1-C_4)$-alkylsulfamoyl; or wherein A is $-CR^5R^6$ and $R^5$ and $R^6$ are each independently selected from hydrogen, $(C_1-C_6)$-alkyl, $(C_3-C_7)$-cycloalkyl, aryl, or a substituent of the α-carbon atom of an α-amino acid, wherein the amino acid is a natural L-amino acid or its D-isomer.

B is $-CO_2H$, $-NH_2$, $-NHSO_2CF_3$, tetrazolyl, imidazolyl, 3-hydroxyisoxazolyl, $-CONHCOR'''$, $-CONH-$ SOR''', CONHSO$_2$R''', where R'''' is aryl, heteroaryl, (C$_3$-C$_7$)-cycloalkyl, or (C$_1$-C$_4$)-alkyl, optionally monosubstituted by (C$_6$-C$_{12}$)-aryl, heteroaryl, OH, SH, (C$_1$-C$_4$)-alkyl, (C$_1$-C$_4$)-alkoxy, (C$_1$-C$_4$)-thioalkyl, (C$_1$-C$_4$)-sulfinyl, (C$_1$-C$_4$)-sulfonyl, CF$_3$, Cl, Br, F, I, NO2, —COOH, (C$_2$-C$_5$)-alkoxycarbonyl, NH$_2$, mono-(C$_1$-C$_4$-alkyl)-amino, di-(C$_1$-C$_4$-alkyl)-amino, or (C$_1$-C$_4$)-perfluoroalkyl; or wherein B is a CO$_2$-G carboxyl radical, where G is a radical of an alcohol G-OH in which G is selected from (C$_1$-C$_{20}$)-alkyl radical, (C$_3$-C$_8$) cycloalkyl radical, (C$_2$-C$_{20}$)-alkenyl radical, (C$_3$-C$_8$)-cycloalkenyl radical, retinyl radical, (C$_2$-C$_{20}$)-alkynyl radical, (C$_4$-C$_{20}$)-alkenynyl radical, where the alkenyl, cycloalkenyl, alkynyl, and alkenynyl radicals contain one or more multiple bonds; (C$_6$-C$_{16}$)-carbocyclic aryl radical, (C$_7$-C$_{16}$)-carbocyclic aralkyl radical, heteroaryl radical, or heteroaralkyl radical, wherein a heteroaryl radical or heteroaryl moiety of a heteroaralkyl radical contains 5 or 6 ring atoms; and wherein radicals defined for G are substituted by one or more hydroxyl, halogen, cyano, trifluoromethyl, nitro, carboxyl, (C$_1$-C$_{12}$)-alkyl, (C$_3$-C$_8$)-cycloalkyl, (C$_5$-C$_8$)-cycloalkenyl, (C$_6$-C$_{12}$)-aryl, (C$_7$-C$_{16}$)-aralkyl, (C$_2$-C$_{12}$)-alkenyl, (C$_2$-C$_{12}$)-alkynyl, (C$_1$-C$_{12}$)-alkoxy, (C$_1$-C$_{12}$)-alkoxy-(C$_1$-C$_{12}$)-alkyl, (C$_1$-C$_{12}$)-alkoxy-(C$_1$-C$_{12}$)-alkoxy, (C$_6$-C$_{12}$)-aryloxy, (C$_7$-C$_{16}$)-aralkyloxy, (C$_1$-C$_8$)-hydroxyalkyl, —O—[CH$_2$]$_x$—C$_f$H$_{(2f+1-g)}$—F$_g$, OCF$_2$Cl, —OCF$_2$—CHFCl, (C$_1$-C$_{12}$)-alkylcarbonyl, (C$_3$-C$_8$)-cycloalkylcarbonyl, (C$_6$-C$_{12}$)-arylcarbonyl, (C$_7$-C$_{16}$)-aralkylcarbonyl, cinnamoyl, (C$_2$-C$_{12}$)-alkenylcarbonyl, (C$_2$-C$_{12}$)-alkynylcarbonyl, (C$_1$-C$_{12}$)-alkoxycarbonyl, (C$_1$-C$_{12}$)-alkoxy-(C$_1$-C$_{12}$)-alkoxycarbonyl, (C$_6$-C$_{12}$)-aryloxycarbonyl, (C$_7$-C$_{16}$)-aralkoxycarbonyl, (C$_3$-C$_8$)-cycloalkoxycarbonyl, (C$_2$-C$_{12}$)-alkenyloxycarbonyl, (C$_2$-C$_{12}$)-alkynyloxycarbonyl, acyloxy, (C$_1$-C$_{12}$)-alkoxycarbonyloxy, (C$_1$-C$_{12}$)-alkoxy-(C$_1$-C$_{12}$)-alkoxycarbonyloxy, (C$_6$-C$_{12}$)-aryloxycarbonyloxy, (C$_7$-C$_{16}$)-aralkyloxycarbonyloxy, (C$_3$-C$_8$)-cycloalkoxycarbonyloxy, (C$_2$-C$_{12}$)-alkenyloxycarbonyloxy, (C$_2$-C$_{12}$)-alkynyloxycarbonyloxy, carbamoyl, N—(C$_1$-C$_{12}$)-alkylcarbamoyl, N.N-di(C$_1$-C$_{12}$)-alkylcarbamoyl, N—(C$_3$-C$_8$)-cycloalkyl-carbamoyl, N—(C$_6$-C$_{16}$)-arylcarbamoyl, N—(C$_7$-C$_{16}$)-aralkylcarbamoyl, N—(C$_1$-C$_{10}$)-alkyl-N—(C$_6$-C$_{16}$)-arylcarbamoyl, N—(C$_1$-C$_{10}$)-alkyl-N—(C$_7$-C$_{16}$)-aralkylcarbamoyl, N—((C$_1$-C$_{10}$)-alkoxy-(C$_1$-C$_{10}$)-alkyl)-carbamoyl, N—((C$_6$-C$_{12}$)-aryloxy-(C$_1$-C$_{10}$)alkyl)-carbamoyl, N—((C$_7$-C$_{16}$)-aralkyloxy-(C$_1$-C$_{10}$)-alkyl)-carbamoyl, N—(C$_1$-C$_{10}$)-alkyl-N—((C$_1$-C$_{10}$)-alkoxy-(C$_1$-C$_{10}$)-alkyl)-carbamoyl, N—(C$_1$-C$_{10}$)-alkyl-N—((C$_6$-C$_{16}$)-aryloxy-(C$_1$-C$_{10}$)-alkyl)-carbamoyl, N—(C$_1$-C$_{10}$)-alkyl-N—((C$_7$-C$_{16}$)-aralkyloxy-(C$_1$-C$_{10}$)-alkyl)-carbamoyl, carbamoyloxy, N—(C$_1$-C$_{12}$)-alkylcarbamoyloxy, N.N-di-(C$_1$-C$_{12}$)-alkylcarbamoyloxy, N—(C$_3$-C$_8$)-cycloalkylcarbamoyloxy, N—(C$_6$-C$_{12}$)-arylcarbamoyloxy, N—(C$_7$-C$_{16}$)-aralkylcarbamoyloxy, N—(C$_1$-C$_{10}$)-alkyl-N—(C$_6$-C$_{12}$)-arylcarbamoyloxy, N(C$_1$-C$_{10}$)-alkyl-N—(C$_7$-C$_{16}$)-aralkylcarbamoyloxy, N—((C$_1$-C$_{10}$)-alkyl)-carbamoyloxy, N—((C$_6$-C$_{12}$)-aryloxy-(C$_1$-C$_{10}$)-alkyl)-carbamoyloxy, N—((C$_7$-C$_{16}$)-aralkyloxy-(C$_1$-C$_{10}$)-alkyl)-carbamoyloxy, N—(C$_1$-C$_{10}$)-alkyl-N—((C$_1$-C$_{10}$)-alkoxy-(C$_1$-C$_{10}$)-alkyl)-carbamoyloxy, N—(C$_1$-C$_{10}$)-alkyl-N—((C$_6$-C$_{12}$)-aryloxy-(C$_1$-C$_{10}$)-alkyl)-carbamoyloxy, N—(C$_1$-C$_{10}$)-alkyl-N—((C$_7$-C$_{16}$)-aralkyloxy-(C$_1$-C$_{10}$)-alkyl)-carbamoyloxy, amino, (C$_1$-C$_{12}$)-alkylamino, di-(C$_1$-C$_{12}$)-alkylamino, (C$_3$-C$_8$)-cycloalkylamino, (C$_2$-C$_{12}$)-alkenylamino, (C$_2$-C$_{12}$)-alkynylamino, N—(C$_6$-C$_{12}$)-arylamino, N—(C$_7$-C$_{11}$)-aralkylamino, N-alkyl-aralkylamino, N-alkyl-arylamino, (C$_1$-C$_{12}$)-alkoxyamino, (C$_1$-C$_{12}$)-alkoxy-N—(C$_1$-C$_{10}$)-alkylamino, (C$_1$-C$_{12}$)-alkylcarbonylamino, (C$_3$-C$_8$)-cycloalkylcarbonylamino, (C$_6$-C$_{12}$) arylcarbonylamino, (C$_7$-C$_{16}$)-aralkylcarbonylamino, (C$_1$-C$_{12}$)-alkylcarbonyl-N—(C$_1$-C$_{10}$)-alkylamino, (C$_3$-C$_8$)-cycloalkylcarbonyl-N—(C$_1$-C$_{10}$)-alkylamino, (C$_6$-C$_{12}$)-arylcarbonyl-N—(C$_1$-C$_{10}$) alkylamino, (C$_7$-C$_{11}$)-aralkylcarbonyl-N—(C$_1$-C$_{10}$)-alkylamino, (C$_1$-C$_{12}$)-alkylcarbonylamino-(C$_1$-C$_8$)-alkyl, (C$_3$-C$_8$)-cycloalkylcarbonylamino-(C$_1$-C$_8$)alkyl, (C$_6$-C$_{12}$)-arylcarbonylamino-(C$_1$-C$_8$)-alkyl, (C$_7$-C$_{12}$)-aralkylcarbonylamino(C$_1$-C$_8$)-alkyl, amino-(C$_1$-C$_{10}$)-alkyl, N—(C$_1$-C$_{10}$) alkylamino-(C$_1$-C$_{10}$)-alkyl, N.N-di-(C$_1$-C$_{10}$)-alkylamino-(C$_1$-C$_{10}$)-alkyl, (C$_3$-C$_8$)cycloalkylamino-(C$_1$-C$_{10}$-alkyl, (C$_1$-C$_{12}$)-alkylmercapto, (C$_1$-C$_{12}$)-alkylsulfinyl, (C$_1$-C$_{12}$)-alkylsulfonyl, (C$_6$-C$_{16}$)-arylmercapto, (C$_6$-C$_{16}$)-arylsulfinyl, (C$_6$-C$_{12}$)-arylsulfonyl, (C$_7$-C$_{16}$)-aralkylmercapto, (C$_7$-C$_{16}$)-aralkylsulfinyl, (C$_7$-C$_{16}$)-aralkylsulfonyl, sulfamoyl, N—(C$_1$-C$_{10}$)-alkylsulfamoyl, N.N-di(C$_1$-C$_{10}$)-alkylsulfamoyl, (C$_3$-C$_8$)-cycloalkylsulfamoyl, N—(C$_6$-C$_{12}$)-alkylsulfamoyl, N—(C$_7$-C$_{16}$)-aralkylsulfamoyl, N—(C$_1$-C$_{10}$)-alkyl-N—(C$_6$-C$_{12}$)-arylsulfamoyl, N—(C$_1$-C$_{10}$)-alkyl-N—(C$_7$-C$_{16}$)-aralkylsulfamoyl, (C$_1$-C$_{10}$)-alkylsulfonamido, N—((C$_1$-C$_{10}$)-alkyl)-(C$_1$-C$_{10}$)-alkylsulfonamido, (C$_7$-C$_{16}$)-aralkylsulfonamido, or N—((C$_1$-C$_{10}$)-alkyl-(C$_7$-C$_{16}$)-aralkylsulfonamido; wherein radicals which are aryl or contain an aryl moiety, may be substituted on the aryl by one to five identical or different hydroxyl, halogen, cyano, trifluoromethyl, nitro, carboxyl, (C$_1$-C$_{12}$)-alkyl, (C$_3$-C$_8$)-cycloalkyl, (C$_6$-C$_{12}$)-aryl, (C$_7$-C$_{16}$)-aralkyl, (C$_1$-C$_{12}$)-alkoxy, (C$_1$-C$_{12}$)-alkoxy-(C$_1$-C$_{12}$)alkyl, (C$_1$-C$_{12}$)-alkoxy-(C$_1$ C$_{12}$)alkoxy, (C$_6$-C$_{12}$)-aryloxy, (C$_7$-C$_{16}$)-aralkyloxy, (C$_1$-C$_8$)-hydroxyalkyl, (C$_1$-C$_{12}$)-alkylcarbonyl, (C$_3$-C$_8$)-cycloalkyl-carbonyl, (C$_6$-C$_{12}$)-arylcarbonyl, (C$_7$-C$_{16}$) aralkylcarbonyl, (C$_1$-C$_{12}$)-alkoxycarbonyl, (C$_1$-C$_{12}$)-alkoxy-(C$_1$-C$_{12}$)-alkoxycarbonyl, (C$_6$-C$_{12}$)-aryloxycarbonyl, (C$_7$-C$_{16}$)-aralkoxycarbonyl, (C$_3$-C$_8$)-cycloalkoxycarbonyl, (C$_2$-C$_{12}$)-alkenyloxycarbonyl, (C$_2$-C$_{12}$)-alkynyloxycarbonyl, (C$_1$-C$_{12}$)-alkylcarbonyloxy, (C$_3$-C$_8$)-cycloalkylcarbonyloxy, (C$_6$-C$_{12}$)-arylcarbonyloxy, (C$_7$-C$_{16}$)-aralkylcarbonyloxy, cinnamoyloxy, (C$_2$-C$_{16}$)-alkenylcarbonyloxy, (C$_2$-C$_{12}$)-alkynylcarbonyloxy, alkoxycarbonyloxy, (C$_1$-C$_{12}$)-alkoxy-(C$_1$-C$_{12}$)-alkoxycarbonyloxy, (C$_6$-C$_{12}$)-aryloxycarbonyloxy, (C$_7$-C$_{16}$)-aralkyloxycarbonyloxy, (C$_3$-C$_8$)-cycloalkoxycarbonyloxy, (C$_2$-C$_{12}$)-alkenyloxycarbonyloxy, (C$_2$-C$_{12}$)-alkynyloxycarbonyloxy, carbamoyl, N—(C$_1$-C$_{12}$)-alkylcarbamoyl, N.N-di-(C$_1$-C$_{12}$)-alkylcarbamoyl, N—(C$_3$-C$_8$)-cycloalkylcarbamoyl, N—(C$_6$-C$_{12}$)-arylcarbamoyl, N—(C$_7$-C$_{16}$)-aralkylcarbamoyl, N—(C$_1$-C$_{10}$)-alkyl-N—(C$_6$-C$_{12}$)-arylcarbamoyl, N—(C$_1$-C$_{10}$)-alkyl-N—(C$_7$-C$_{16}$)-aralkylcarbamoyl, N—((C$_1$-C$_{10}$)-alkoxy-(C$_1$-C$_{10}$)-alkyl)-carbamoyl, N—((C$_6$-C$_{12}$)-aryloxy-(C$_1$-C$_{10}$)-alkyl)-carbamoyl, N—((C$_7$-C$_{16}$)-aralkyloxy-(C$_1$-C$_{10}$)-alkyl)-carbamoyl, N—(C$_1$-C$_{10}$)-alkyl-N—((C$_1$-C$_{10}$)-alkoxy-(C$_1$-C$_{10}$)-alkyl)-carbamoyl, N—(C$_1$-C$_{10}$)-alkyl-N—((C$_6$-C$_{12}$)-aryloxy-(C$_1$-C$_{10}$)-alkyl)-carbamoyl, N—(C$_1$-C$_{10}$)-alkyl-N—((C$_7$-C$_{16}$)-aralkyloxy-(C$_1$-C$_{10}$)-alkyl)-carbamoyl, carbamoyloxy, N—(C$_1$-C$_{12}$)-alkylcarbamoyloxy, N.N-di-(C$_1$-C$_{12}$)-alkylcarbamoyloxy, N—(C$_3$-C$_8$)-cycloalkylcarbamoyloxy, N—(C$_6$-C$_{12}$)-arylcarbamoyloxy, N—(C$_7$-C$_{16}$)-aralkylcarbamoyloxy, N—(C$_1$-C$_{10}$)-alkyl-N—(C$_6$-C$_{12}$)-arylcarbamoyloxy, N(C$_1$-C$_{10}$)-alkyl-N—(C$_7$-C$_{16}$)-aralkylcarbamoyloxy, N—((C$_1$-C$_{10}$)-alkyl)-carbamoyloxy, N—((C$_6$-C$_{12}$)-aryloxy-(C$_1$-C$_{10}$)-alkyl)-carbamoyloxy, N—((C$_7$-C$_{16}$)-aralkyloxy-(C$_1$-C$_{10}$)-alkyl)-carbamoyloxy, N—(C$_1$-C$_{10}$)-alkyl-N—((C$_1$-C$_{10}$)-alkoxy-(C$_1$-C$_{10}$)-alkyl)-carbamoyloxy, N—(C$_1$-C$_{10}$)-alkyl-N—((C$_6$-C$_{12}$)-aryloxy-(C$_1$-C$_{10}$)-alkyl)-carbamoyloxy, N—(C$_1$-C$_{10}$)-alkyl-N—((C$_7$-C$_{16}$)-aralkyloxy-(C$_1$-C$_{10}$)-alkyl)-carbamoyloxy, amino, $(C_1-C_{12})$-alkylamino, di-$(C_1-C_{12})$-alkylamino, $(C_3-C_8)$-cycloalkylamino, $(C_3-C_{12})$-alkenylamino, $(C_3-C_{12})$-alkynylamino, N—$(C_6-C_{12})$-arylamino, N—$(C_7-C_{11})$-aralkylamino, N-alkylaralkylamino, N-alkyl-arylamino, $(C_1-C_{12})$-alkoxyamino, $(C_1-C_{12})$-alkoxy-N—$(C_1-C_{10})$-alkylamino, $(C_1-C_{12})$-alkylcarbonylamino, $(C_3-C_8)$-cycloalkylcarbonylamino, $(C_6-C_{12})$-arylcarbonylamino, $(C_7-C_{16})$-alkylcarbonylamino, $(C_1-C_{12})$-alkylcarbonyl-N—$(C_1-C_{10})$-alkylamino, $(C_3-C_8)$-cycloalkylcarbonyl-N—$(C_1-C_{10})$-alkylamino, $(C_6-C_{12})$-arylcarbonyl-N—$(C_1-C_{10})$-alkylamino, $(C_7-C_{11})$-aralkylcarbonyl-N—$(C_1-C_{10})$-alkylamino, $(C_1-C_{12})$-alkylcarbonylamino-$(C_1-C_8)$-alkyl, $(C_3-C_8)$-cycloalkylcarbonylamino-$(C_1-C_8)$-alkyl, $(C_6-C_{12})$-arylcarbonylamino-$(C_1-C_8)$-alkyl, $(C_7-C_{16})$-aralkylcarbonylamino-$(C_1-C_8)$-alkyl, amino-$(C_1-C_{10})$-alkyl, N—$(C_1-C_{10})$-alkylamino-$(C_1-C_{10})$alkyl, N.N-di-$(C_1-C_{10})$-alkylamino-$(C_1-C_{10})$-alkyl, $(C_3-C_8)$-cycloalkylamino-$(C_1-C_{10})$-alkyl, $(C_1-C_{12})$-alkylmercapto, $(C_1-C_{12})$-alkylsulfinyl, $(C_1-C_{12})$-alkylsulfonyl, $(C_6-C_{12})$-arylmercapto, $(C_6-C_{12})$-arylsulfinyl, $(C_6-C_{12})$-arylsulfonyl, $(C_7-C_{16})$-aralkylmercapto, $(C_7-C_{16})$-aralkylsulfinyl, or $(C_7-C_{16})$-aralkylsulfonyl;

X is O or S;

Q is O, S, NR', or a bond;

where, if Q is a bond, $R^4$ is halogen, nitrile, or trifluoromethyl;

or where, if Q is O, S, or NR', $R^4$ is hydrogen, $(C_1-C_{10})$-alkyl radical, $(C_2-C_{10})$-alkenyl radical, $(C_2-C_{10})$-alkynyl radical, wherein alkenyl or alkynyl radical contains one or two C—C multiple bonds; unsubstituted fluoroalkyl radical of the formula —$[CH_2]_x$—$C_fH_{(2f+1-g)}$—$F_g$, $(C_1-C_8)$-alkoxy-$(C_1-C_6)$-alkyl radical, $(C_1-C_6)$-alkoxy-$(C_1-C_4)$-alkoxy-$(C_1-C_4)$-alkyl radical, aryl radical, heteroaryl radical, $(C_7-C_{11})$-aralkyl radical, or a radical of the formula Z

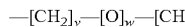

$$—[CH_2]_v—[O]_w—[CH_2]_t-E \quad (Z)$$

where

E is a heteroaryl radical, a $(C_3-C_8)$-cycloalkyl radical, or a phenyl radical of the formula F

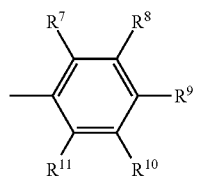

(F)

v is 0-6, w is 0 or 1, t is 0-3, and $R^7$, $R^8$, $R^9$, $R^{10}$, and $R^{11}$ are identical or different and are hydrogen, halogen, cyano, nitro, trifluoromethyl, $(C_1-C_6)$-alkyl, $(C_3-C_8)$-cycloalkyl, $(C_1-C_6)$-alkoxy, —O—$[CH_2]_x$—$C_fH_{(2f+1-g)}$—$F_g$, —$OCF_2$—Cl, —O—$CF_2$—CHFCl, $(C_1-C_6)$-alkylmercapto, $(C_1-C_6)$-hydroxyalkyl, $(C_1-C_6)$-alkoxy-$(C_1-C_6)$-alkoxy, $(C_1-C_6)$-alkoxy-$(C_1-C_6)$-alkyl, $(C_1-C_6)$-alkylsulfinyl, $(C_1-C_6)$-alkylsulfonyl, $(C_1-C_6)$-alkylcarbonyl, $(C_1-C_8)$-alkoxycarbonyl, carbamoyl, N—$(C_1-C_8)$-alkylcarbamoyl, N,N-di-$(C_1-C_8)$-alkylcarbamoyl, or $(C_7-C_{11})$-aralkylcarbamoyl, optionally substituted by fluorine, chlorine, bromine, trifluoromethyl, $(C_1-C_6)$-alkoxy, N—$(C_3-C_8)$-cycloalkylcarbamoyl, N—$(C_3-C_8)$-cycloalkyl-$(C_1-C_4)$-alkylcarbamoyl, $(C_1-C_6)$-alkylcarbonyloxy, phenyl, benzyl, phenoxy, benzyloxy, $NR^yR^z$ wherein $R^y$ and $R^z$ are independently selected from hydrogen, $(C_1-C_{12})$-alkyl, $(C_1-C_8)$-alkoxy-$(C_1-C_8)$-alkyl, $(C_7-C_{12})$-aralkoxy-$(C_1-C_8)$-alkyl, $(C_6-C_{12})$-aryloxy-$(C_1-C_8)$-alkyl, $(C_3-C_{10})$-cycloalkyl, $(C_3-C_{12})$-alkenyl, $(C_3-C_{12})$-alkynyl, $(C_6-C_{12})$-aryl, $(C_7-C_{11})$-aralkyl, $(C_1-C_{12})$-alkoxy, $(C_7-C_{12})$aralkoxy, $(C_1-C_{12})$-alkylcarbonyl, $(C_3-C_8)$-cycloalkylcarbonyl, $(C_6-C_{12})$ arylcarbonyl, $(C_7-C_{16})$-aralkylcarbonyl; or further wherein $R^y$ and $R^z$ together are —$[CH_2]_h$, in which a $CH_2$ group can be replaced by O, S, N—$(C_1-C_4)$-alkylcarbonylimino, or N—$(C_1-C_4)$-alkoxycarbonylimino; phenylmercapto, phenylsulfonyl, phenylsulfinyl, sulfamoyl, N—$(C_1-C_8)$-alkylsulfamoyl, or N, N-di-$(C_1-C_8)$-alkylsulfamoyl; or alternatively $R^7$ and $R^8$, $R^8$ and $R^9$, $R^9$ and $R^{10}$, or $R^{10}$ and $R^{11}$, together are a chain selected from —$[CH_2]_n$— or —CH=CH—CH=CH—, where a $CH_2$ group of the chain is optionally replaced by O, S, SO, $SO_2$, or $NR^Y$; and n is 3, 4, or 5; and if E is a heteroaryl radical, said radical can carry 1-3 substituents selected from those defined for $R^7$-$R^{11}$, or if E is a cycloalkyl radical, the radical can carry one substituent selected from those defined for $R^7$-$R^{11}$;

or where, if Q is NR', $R^4$ is alternatively R'', where R' and R'' are identical or different and are hydrogen, $(C_6-C_{12})$-aryl, $(C_7-C_{11})$-aralkyl, $(C_1-C_8)$-alkyl, $(C_1-C_8)$-alkoxy-$(C_1-C_8)$-alkyl, $(C_7-C_{12})$-aralkoxy-$(C_1-C_8)$-alkyl, $(C_6-C_{12})$-aryloxy-$(C_1-C_8)$-alkyl, $(C_1-C_{10})$-alkylcarbonyl, optionally substituted $(C_7-C_{16})$-aralkylcarbonyl, or optionally substituted $C_6-C_{12}$)-arylcarbonyl; or R' and R'' together are —$[CH_2]_h$, in which a $CH_2$ group can be replaced by O, S, N-acylimino, or N—$(C_1-C_{10})$-alkoxycarbonylimino, and h is 3 to 7.

Y is N or $CR^3$;

$R^1$, $R^2$ and $R^3$ are identical or different and are hydrogen, hydroxyl, halogen, cyano, trifluoromethyl, nitro, carboxyl, $(C_1-C_{20})$-alkyl, $(C_3-C_8)$-cycloalkyl, $(C_3-C_8)$cycloalkyl-$(C_1-C_{12})$-alkyl, $(C_3-C_8)$-cycloalkoxy, $(C_3-C_8)$-cycloalkyl-$(C_1-C_{12})$-alkoxy, $(C_3-C_8)$-cycloalkyloxy-$(C_1-C_{12})$-alkyl, $(C_3-C_8)$-cycloalkyloxy-$(C_1-C_{12})$-alkoxy, $(C_3-C_8)$-cycloalkyl-$(C_1-C_8)$-alkyl-$(C_1-C_6)$-alkoxy, $(C_3-C_8)$-cycloalkyl-$(C_1-C_8)$-alkoxy-$(C_1-C_6)$-alkyl, $(C_3-C_8)$-cycloalkyloxy-$(C_1-C_8)$-alkoxy-$(C_1-C_6)$-alkyl, $(C_3-C_8)$-cycloalkoxy-$(C_1-C_8)$-alkoxy-$(C_1-C_8)$-alkoxy, $(C_6-C_{12})$-aryl, $(C_7-C_{16})$-aralkyl, $(C_7-C_{16})$-aralkenyl, $(C_7-C_{16})$-aralkynyl, $(C_2-C_{20})$-alkenyl, $(C_2-C_{20})$-alkynyl, $(C_1-C_{20})$-alkoxy, $(C_2-C_{20})$-alkenyloxy, $(C_2-C_{20})$-alkynyloxy, retinyloxy, $(C_1-C_{20})$-alkoxy-$(C_1-C_{12})$-alkyl, $(C_1-C_{12})$-alkoxy-$(C_1-C_{12})$-alkoxy, $(C_1-C_{12})$-alkoxy-$(C_1-C_8)$-alkoxy-$(C_1-C_8)$-alkyl, $(C_6-C_{12})$-aryloxy, $(C_7-C_{16})$-aralkyloxy, $(C_6-C_{12})$-aryloxy-$(C_1-C_6)$-alkoxy, $(C_7-C_{16})$-aralkoxy-$(C_1-C_6)$-alkoxy, $(C_1-C_{16})$-hydroxyalkyl, $(C_6-C_{16})$-aryloxy-$(C_1-C_8)$-alkyl, $(C_7-C_{16})$-aralkoxy-$(C_1-C_8)$-alkyl, $(C_6-C_{12})$-aryloxy-$(C_1-C_8)$-alkoxy-$(C_1-C_6)$-alkyl, $(C_7-C_{12})$-aralkyloxy-$(C_1-C_8)$-alkoxy-$(C_1-C_6)$-alkyl, $(C_2-C_{20})$-alkenyloxy-$(C_1-C_6)$-alkyl, $(C_2-C_{20})$-alkynyloxy-$(C_1-C_6)$-alkyl, retinyloxy-$(C_1-C_6)$-alkyl, —O—$[CH_2]_xC_fH_{(2f+1-g)}F_g$, $OCF_2Cl$, —$OCF_2$—CHFCl, $(C_1-C_{20})$-alkylcarbonyl, $(C_3-C_8)$-cycloalkylcarbonyl, $(C_6-C_{12})$-arylcarbonyl, $(C_7-C_{16})$-aralkylcarbonyl, cinnamoyl, $(C_2-C_{20})$-alkenylcarbonyl, $(C_2-C_{20})$-alkynylcarbonyl, $(C_1-C_{20})$-alkoxycarbonyl, $(C_1-C_{12})$-alkoxy-$(C_1-C_{12})$-alkoxycarbonyl, $(C_6-C_{12})$-aryloxycarbonyl, $(C_7-C_{16})$-aralkoxycarbonyl, $(C_3-C_8)$-cycloalkoxycarbonyl, $(C_2-C_{20})$-alkenyloxycarbonyl, retinyloxycarbonyl, $(C_2-C_{20})$-alkynyloxycarbonyl, $(C_6-C_{12})$-aryloxy-$(C_1-C_6)$-alkoxycarbonyl, $(C_7-C_{16})$-aralkoxy-$(C_1-C_6)$-alkoxycarbonyl, $(C_3-C_8)$-cycloalkyl-$(C_1-C_6)$-alkoxycarbonyl, $(C_3-C_8)$-cycloalkoxy-$(C_1-C_6)$-alkoxycarbonyl, $(C_1-C_{12})$-alkylcarbonyloxy, $(C_3-C_8)$-cycloalkylcarbonyloxy, $(C_6-C_{12})$-arylcarbonyloxy, $(C_7-C_{16})$-aralkylcarbonyloxy, cinnamoyloxy, $(C_2-C_{12})$-alkenylcarbonyloxy, $(C_2-C_{12})$-alkynylcarbonyloxy, $(C_1-C_{12})$-alkoxycarbonyloxy, $(C_1-C_{12})$-alkoxy-$(C_1-C_{12})$- alkoxycarbonyloxy, $(C_6-C_{12})$-aryloxycarbonyloxy, $(C_7-C_{16})$-aralkyloxycarbonyloxy, $(C_3-C_8)$-cycloalkoxycarbonyloxy, $(C_2-C_{12})$-alkenyloxycarbonyloxy, $(C_2-C_{12})$-alkynyloxycarbonyloxy, carbamoyl, N—$(C_1-C_{12})$-alkylcarbamoyl, N,N-di-$(C_1-C_{12})$-alkylcarbamoyl, N—$(C_3-C_8)$-cycloalkylcarbamoyl, N,N-dicyclo-$(C_3-C_8)$-alkylcarbamoyl, N—$(C_1-C_{10})$-alkyl-N—$(C_3-C_8)$-cycloalkylcarbamoyl, N—$((C_3-C_8)$-cycloalkyl-$(C_1-C_6)$-alkyl)-carbamoyl, N—$(C_1-C_6)$-alkyl-N—$((C_3-C_8)$-cycloalkyl-$(C_1-C_6)$-alkyl)-carbamoyl, N-(+)-dehydroabietylcarbamoyl, N—$(C_1-C_6)$-alkyl-N-(+)-dehydroabietylcarbamoyl, N—$(C_6-C_{12})$-arylcarbamoyl, N—$(C_7-C_{16})$-aralkylcarbamoyl, N—$(C_1-C_{10})$-alkyl-N—$(C_6-C_{16})$-arylcarbamoyl, N—$(C_1-C_{10})$-alkyl-N—$(C_7-C_{16})$-aralkylcarbamoyl, N—$((C_1-C_{18})$-alkoxy-$(C_1-C_{10})$-alkyl)-carbamoyl, N—$((C_6-C_{16})$-aryloxy-$(C_1-C_{10})$-alkyl)-carbamoyl, N—$((C_7-C_{16})$-aralkyloxy-$(C_1-C_{10})$-alkyl)-carbamoyl, N—$(C_1-C_{10})$-alkyl-N—$((C_1-C_{10})$-alkoxy-$(C_1-C_{10})$-alkyl)-carbamoyl, N—$(C_1-C_{10})$-alkyl-N—$((C_6-C_{12})$-aryloxy-$(C_1-C_{10})$-alkyl)-carbamoyl, N—$(C_1-C_{10})$-alkyl-N—$((C_7-C_{16})$-aralkyloxy-$(C_1-C_{10})$-alkyl)-carbamoyl; CON$(CH_2)_h$, in which a $CH_2$ group can be replaced by O, S, N—$(C_1-C_8)$-alkylimino, N—$(C_3-C_8)$-cycloalkylimino, N—$(C_3-C_8)$-cycloalkyl-$(C_1-C_4)$-alkylimino, N—$(C_6-C_{12})$-arylimino, N—$(C_7-C_{16})$-aralkylimino, N—$(C_1-C_4)$-alkoxy-$(C_1-C_6)$-alkylimino, and h is from 3 to 7; a carbamoyl radical of the formula R

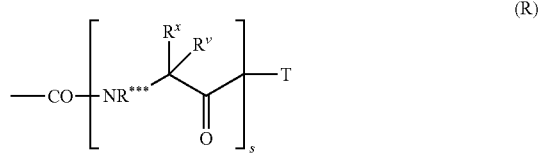

(R)

in which
$R^x$ and $R^v$ are each independently selected from hydrogen, $(C_1-C_6)$-alkyl, $(C_3-C_7)$-cycloalkyl, aryl, or the substituent of an α-carbon of an α-amino acid, to which the L- and D-amino acids belong,
s is 1-5,
T is OH, or NR*R**, and R*, R and R* are identical or different and are selected from hydrogen, $(C_6-C_{12})$-aryl, $(C_7-C_{11})$-aralkyl, $(C_3-C_8)$-cycloalkyl, (±)-dehydroabietyl, $(C_1-C_8)$-alkoxy-$(C_1-C_8)$-alkyl, $(C_7-C_{12})$-aralkoxy-$(C_1-C_8)$-alkyl, $(C_6-C_{12})$-aryloxy-$(C_1-C_8)$-alkyl, $(C_1-C_{10})$-alkanoyl, optionally substituted $(C_7-C_{16})$-aralkanoyl, optionally substituted $(C_6-C_{12})$-aroyl; or R* and R** together are —$[CH_2]_h$, in which a $CH_2$ group can be replaced by O, S, SO, $SO_2$, N-acylamino, N—$(C_1-C_{10})$-alkoxycarbonylimino, N—$(C_1-C_8)$-alkylimino, N—$(C_3-C_8)$-cycloalkylimino, N—$(C_3-C_8)$-cycloalkyl-$(C_1-C_4)$-alkylimino, N—$(C_6-C_{12})$-arylimino, N—$(C_7-C_{16})$-aralkylimino, N—$(C_1-C_4)$-alkoxy-$(C_1-C_6)$-alkylimino, and h is from 3 to 7;
carbamoyloxy, N—$(C_1-C_{12})$-alkylcarbamoyloxy, N,N-di-$(C_1-C_{12})$-alkylcarbamoyloxy, N—$(C_3-C_8)$-cycloalkylcarbamoyloxy, N—$(C_6-C_{12})$-arylcarbamoyloxy, N—$(C_7-c_{16})$-aralkylcarbamoyloxy, N—$(C_1-C_{10})$-alkyl-N—$(C_6-C_{12})$-arylcarbamoyloxy, N—$(C_1-C_{10})$-alkyl-N—$(C_7-C_{16})$-aralkylcarbamoyloxy, N—$((C_1-C_{10})$-alkyl)-carbamoyloxy, N—$((C_6-C_{12})$-aryloxy-$(C_1-C_{10})$-alkyl)-carbamoyloxy, N—$((C_7-C_{16})$-aralkyloxy-$(C_1-C_{10})$-alkyl)-carbamoyloxy, N—$(C_1-C_{10})$-alkyl-N—$((C_1-C_{10})$-alkoxy-$(C_1-C_{10})$-alkyl)-carbamoyloxy, N—$(C_1-C_{10})$-alkyl-N—$((C_6-C_{12})$-aryloxy-$(C_1-C_{10})$-alkyl)-carbamoyloxy, N—$(C_1-C_{10})$-alkyl-N—$((C_7-C_{16})$-aralkyloxy-$(C_1-C_{10})$-alkyl)-carbamoyloxyamino, $(C_1-C_{12})$-alkylamino, di-$(C_1-C_{12})$-alkylamino, $(C_3-C_8)$-cycloalkylamino, $(C_3-C_{12})$-alkenylamino, $(C_3-C_{12})$-alkynylamino, N—$(C_6-C_{12})$-arylamino, N—$(C_7-C_{11})$-aralkylamino, N-alkyl-aralkylamino, N-alkyl-arylamino, $(C_1-C_{12})$-alkoxyamino, $(C_1-C_{12})$-alkoxy-N—$(C_1-C_{10})$-alkylamino, $(C_1-C_{12})$-alkanoylamino, $(C_3-C_8)$-cycloalkanoylamino, $(C_6-C_{12})$-aroylamino, $(C_7-C_{16})$-aralkanoylamino, $(C_1-C_{12})$-alkanoyl-N—$(C_1-C_{10})$-alkylamino, $(C_3-C_8)$-cycloalkanoyl-N—$(C_1-C_{10})$-alkylamino, $(C_6-C_{12})$-aroyl-N—$(C_1-C_{10})$-alkylamino, $(C_7-C_{11})$-aralkanoyl-N—$(C_1-C_{10})$-alkylamino, $(C_1-C_{12})$-alkanoylamino-$(C_1-C_8)$-alkyl, $(C_3-C_8)$-cycloalkanoylamino-$(C_1-C_8)$-alkyl, $(C_6-C_{12})$-aroylamino-$(C_1-C_8)$-alkyl, $(C_7-C_{16})$-aralkanoylamino-$(C_1-C_8)$-alkyl, amino-$(C_1-C_{10})$-alkyl, N—$(C_1-C_{10})$-alkylamino-$(C_1-C_{10})$-alkyl, N,N-di$(C_1-C_{10})$-alkylamino-$(C_1-C_{10})$-alkyl, $(C_3-C_8)$-cycloalkylamino$(C_1-C_{10})$-alkyl, $(C_1-C_{20})$-alkylmercapto, $(C_1-C_{20})$-alkylsulfinyl, $(C_1-C_{20})$-alkylsulfonyl, $(C_6-C_{12})$-arylmercapto, $(C_6-C_{12})$-arylsulfinyl, $(C_6-C_{12})$-arylsulfonyl, $(C_7-C_{16})$-aralkylmercapto, $(C_7-C_{16})$-aralkylsulfinyl, $(C_7-C_{16})$-aralkylsulfonyl, $(C_1-C_{12})$-alkylmercapto-$(C_1-C_6)$-alkyl, $(C_1-C_{12})$-alkylsulfonyl-$(C_1-C_6)$-alkyl, $(C_6-C_{12})$-arylmercapto-$(C_1-C_6)$-alkyl, $(C_6-C_{12})$-arylsulfinyl-$(C_1-C_6)$-alkyl, $(C_6-C_{12})$-arylsulfonyl-$(C_1-C_6)$-alkyl, $(C_7-C_{16})$-aralkylmercapto-$(C_1-C_6)$-alkyl, $(C_7-C_{16})$-aralkylsulfinyl-$(C_1-C_6)$-alkyl, $(C_7-C_{16})$-aralkylsulfonyl-$(C_1-C_6)$-alkyl, sulfamoyl, N—$(C_1-C_{10})$-alkylsulfamoyl, N,N-di-$(C_1-C_{10})$-alkylsulfamoyl, $(C_3-C_8)$-cycloalkylsulfamoyl, N—$(C_6-C_{12})$-arylsulfamoyl, N—$(C_7-C_{16})$-aralkylsulfamoyl, N—$(C_1-C_{10})$-alkyl-N—$(C_6-C_{12})$-arylsulfamoyl, N—$(C_1-C_{10})$-alkyl-N—$(C_7-C_{16})$-aralkylsulfamoyl, $(C_1-C_{10})$-alkylsulfonamido, N—$((C_1-C_{10})$-alkyl)-$(C_1-C_{10})$-alkylsulfonamido, $(C_7-C_{16})$-aralkylsulfonamido, and N—$((C_1-C_{10})$-alkyl-$(C_7-C_{16})$-aralkylsulfonamido; where an aryl radical may be substituted by 1 to 5 substituents selected from hydroxyl, halogen, cyano, trifluoromethyl, nitro, carboxyl, $(C_2-C_{16})$-alkyl, $(C_3-C_8)$-cycloalkyl, $(C_3-C_8)$-cycloalkyl-$(C_1-C_{12})$-alkyl, $(C_3-C_8)$-cycloalkoxy, $(C_3-C_8)$-cycloalkyl-$(C_1-C_{12})$-alkoxy, $(C_3-C_8)$-cycloalkyloxy-$(C_1-C_{12})$-alkyl, $(C_3-C_8)$-cycloalkyloxy-$(C_1-C_{12})$-alkoxy, $(C_3-C_8)$-cycloalkyl-$(C_1-C_8)$-alkyl-$(C_1-C_6)$-alkoxy, $(C_3-C_8)$-cycloalkyl$(C_1-C_8)$-alkoxy-$(C_1-C_6)$-alkyl, $(C_3-C_8)$-cycloalkyloxy-$(C_1-C_8)$-alkoxy-$(C_1-C_6)$-alkyl, $(C_3-C_8)$-cycloalkyloxy-$(C_1-C_8)$-alkoxy, $(C_1-C_{12})$-alkoxy, $(C_6-C_{12})$-aryl, $(C_7-C_{16})$-aralkyl, $(C_2-C_{12})$-alkenyl, $(C_2-C_{12})$-alkynyl, $(C_1-C_{16})$-alkoxy, $(C_1-C_{16})$-alkenyloxy, $(C_1-C_{12})$-alkoxy-$(C_1-C_{12})$-alkyl, $(C_1-C_{12})$-alkoxy-$(C_1-C_{12})$-alkoxy, $(C_1-C_{12})$-alkoxy$(C_1-C_8)$-alkoxy-$(C_1-C_8)$-alkyl, $(C_6-C_{12})$-aryloxy, $(C_7-C_{16})$-aralkyloxy, $(C_6-C_{12})$-aryloxy-$(C_1-C_6)$-alkoxy, $(C_7-C_{16})$-aralkoxy-$(C_1-C_6)$-alkoxy, $(C_1-C_8)$-hydroxyalkyl, $(C_6-C_{16})$-aryloxy-$(C_1-C_8)$-alkyl, $(C_7-C_{16})$-aralkoxy-$(C_1-C_8)$-alkyl, $(C_6-C_{12})$-aryloxy-$(C_1-C_8)$-alkoxy-$(C_1-C_6)$-alkyl, $(C_7-C_{12})$-aralkyloxy-$(C_1-C_8)$-alkoxy-$(C_1-C_6)$-alkyl, —O—$[CH_2]_xC_yH_{(2f+1-g)}F_g$, —$OCF_2Cl$, —$OCF_2$—CHFCl, $(C_1-C_{12})$-alkylcarbonyl, $(C_3-C_8)$-cycloalkylcarbonyl, $(C_6-C_{12})$-arylcarbonyl, $(C_7-C_{16})$-aralkylcarbonyl, $(C_1-C_{12})$-alkoxycarbonyl, $(C_1-C_{12})$-alkoxy-$(C_1-C_{12})$-alkoxycarbonyl, $(C_6-C_{12})$-aryloxycarbonyl, $(C_7-C_{16})$-aralkoxycarbonyl, $(C_3-C_8)$-cycloalkoxycarbonyl, $(C_2-C_{12})$-alkenyloxycarbonyl, $(C_2-C_{12})$-alkynyloxycarbonyl, $(C_6-C_{12})$-aryloxy-$(C_1-C_6)$-alkoxycarbonyl, $(C_7-C_{16})$-aralkoxy-$(C_1-C_6)$-alkoxycarbonyl, $(C_3-C_8)$-cycloalkyl-$(C_1-C_6)$-alkoxycarbonyl, $(C_3-C_8)$-cycloalkoxy-$(C_1-C_6)$-alkoxycarbonyl, $(C_1-C_{12})$-alkylcarbonyloxy, $(C_3-C_8)$-cycloalkylcarbonyloxy, $(C_6-C_{12})$-arylcarbonyloxy, $(C_7-C_{16})$-aralkylcarbonyloxy, cinnamoyloxy, $(C_2-C_{12})$- alkenylcarbonyloxy, ($C_2$-$C_{12}$)-alkynylcarbonyloxy, ($C_1$-$C_{12}$)-alkoxycarbonyloxy, ($C_1$-$C_{12}$)-alkoxy-($C_1$-$C_{12}$)-alkoxycarbonyloxy, ($C_6$-$C_{12}$)-aryloxycarbonyloxy, ($C_7$-$C_{16}$)-aralkyloxycarbonyloxy, ($C_3$-$C_8$)-cycloalkoxycarbonyloxy, ($C_2$-$C_{12}$)-alkenyloxycarbonyloxy, ($C_2$-$C_{12}$)-alkynyloxycarbonyloxy, carbamoyl, N—($C_1$-$C_{12}$)-alkylcarbamoyl, N,N-di($C_1$-$C_{12}$)-alkylcarbamoyl, N—($C_3$-$C_8$)-cycloalkylcarbamoyl, N,N-dicyclo-($C_3$-$C_8$)-alkylcarbamoyl, N—($C_1$-$C_{10}$)-alkyl-N—($C_3$-$C_8$)-cycloalkylcarbamoyl, N—(($C_3$-$C_8$)-cycloalkyl-($C_1$-$C_6$)-alkyl)carbamoyl, N—($C_1$-$C_6$)-alkyl-N—(($C_3$-$C_8$)-cycloalkyl-($C_1$-$C_6$)-alkyl)carbamoyl, N-(+)-dehydroabietylcarbamoyl, N—($C_1$-$C_6$)-alkyl-N-(+)-dehydroabietylcarbamoyl, N—($C_6$-$C_{12}$)-arylcarbamoyl, N—($C_7$-$C_{16}$)-aralkylcarbamoyl, N—($C_1$-$C_{10}$)-alkyl-N—($C_6$-$C_{16}$)-arylcarbamoyl, N—($C_1$-$C_{10}$)-alkyl-N—($C_7$-$C_{16}$)-aralkylcarbamoyl, N—(($C_1$-$C_{16}$)-alkoxy-($C_1$-$C_{10}$)-alkyl)carbamoyl, N—(($C_6$-$C_{16}$)-aryloxy-($C_1$-$C_{10}$)-alkyl)carbamoyl, N—(($C_7$-$C_{16}$)-aralkyloxy-($C_1$-$C_{10}$)-alkyl)carbamoyl, N—($C_1$-$C_{10}$)-alkyl-N—(($C_1$-$C_{10}$)-alkoxy-($C_1$-$C_{10}$)-alkyl)carbamoyl, N—($C_1$-$C_{10}$)-alkyl-N—(($C_6$-$C_{12}$)-aryloxy-($C_1$-$C_{10}$)-alkyl)carbamoyl, N—($C_1$-$C_{10}$)-alkyl-N—(($C_7$-$C_{16}$)-aralkyloxy-($C_1$-$C_{10}$)-alkyl)-carbamoyl, CON($CH_2$)$_h$, in which a $CH_2$ group can be replaced by, O, S, N—($C_1$-$C_4$)-alkylimino, N—($C_3$-$C_8$)-cycloalkylimino, N—($C_3$-$C_8$)-cycloalkyl-($C_1$-$C_4$)-alkylimino, N—($C_6$-$C_{12}$)-arylimino, N—($C_7$-$C_{16}$)-aralkylimino, N—($C_1$-$C_4$)-alkoxy-($C_1$-$C_6$)-alkylimino, and h is from 3 to 7; carbamoyloxy, N—($C_1$-$C_{12}$)-alkylcarbamoyloxy, N,N-di-($C_1$-$C_{12}$)-alkylcarbamoyloxy, N—($C_3$-$C_8$)-cycloalkylcarbamoyloxy, N—($C_6$-$C_{16}$)-arylcarbamoyloxy, N—($C_7$-$C_{16}$)-aralkylcarbamoyloxy, N—($C_1$-$C_{10}$)-alkyl-N—($C_6$-$C_{12}$)-arylcarbamoyloxy, N—($C_1$-$C_{10}$)-alkyl-N—($C_7$-$C_{16}$)-aralkylcarbamoyloxy, N—(($C_1$-$C_{10}$)-alkyl)carbamoyloxy, N—(($C_6$-$C_{12}$)-aryloxy-($C_1$-$C_{10}$)-alkyl)carbamoyloxy, N—(($C_7$-$C_{16}$)-aralkyloxy-($C_1$-$C_{10}$)-alkyl)carbamoyloxy, N—($C_1$-$C_{10}$)-alkyl-N—(($C_1$-$C_{10}$)-alkoxy-($C_1$-$C_{10}$)-alkyl)carbamoyloxy, N—($C_1$-$C_{10}$-alkyl-N—(($C_6$-$C_{12}$)-aryloxy-($C_1$-$C_{10}$)-alkyl)carbamoyloxy, N—($C_1$-$C_{10}$)-alkyl-N—(($C_7$-$C_{16}$)-aralkyloxy-($C_1$-$C_{10}$)-alkyl)carbamoyloxy, amino, ($C_1$-$C_{12}$)-alkylamino, di-($C_1$-$C_{12}$)-alkylamino, ($C_3$-$C_8$)-cycloalkylamino, ($C_3$-$C_{12}$)-alkenylamino, ($C_3$-$C_{12}$)-alkynylamino, N—($C_6$-$C_{12}$)-arylamino, N—($C_7$-$C_{11}$)-aralkylamino, N-alkyl-aralkylamino, N-alkyl-arylamino, ($C_1$-$C_{12}$)-alkoxyamino, ($C_1$-$C_{12}$)-alkoxy-N—($C_1$-$C_{10}$)-alkylamino, ($C_1$-$C_{12}$)-alkanoylamino, ($C_3$-$C_8$)-cycloalkanoylamino, ($C_6$-$C_{12}$)-aroylamino, ($C_7$-$C_{16}$)-aralkanoylamino, ($C_1$-$C_{12}$)-alkanoyl-N—($C_1$-$C_{10}$)-alkylamino, ($C_3$-$C_8$)-cycloalkanoyl-N—($C_1$-$C_{10}$)-alkylamino, ($C_6$-$C_{12}$)-aroyl-N—($C_1$-$C_{10}$)-alkylamino, ($C_7$-$C_{11}$)-aralkanoyl-N—($C_1$-$C_{10}$)-alkylamino, ($C_1$-$C_{12}$)-alkanoylamino-($C_1$-$C_8$)-alkyl, ($C_3$-$C_8$)-cycloalkanoylamino-($C_1$-$C_8$)-alkyl, ($C_6$-$C_{12}$)-aroylamino-($C_1$-$C_8$)-alkyl, ($C_7$-$C_{16}$)-aralkanoylamino-($C_1$-$C_8$)-alkyl, amino-($C_1$-$C_{10}$)-alkyl, N—($C_1$-$C_{10}$)-alkylamino-($C_1$-$C_{10}$)-alkyl, N,N-di-($C_1$-$C_{10}$)-alkylamino-($C_1$-$C_{10}$)-alkyl, ($C_3$-$C_8$)-cycloalkylamino-($C_1$-$C_{10}$)-alkyl, ($C_1$-$C_{12}$)-alkylmercapto, ($C_1$-$C_{12}$)-alkylsulfinyl, ($C_1$-$C_{12}$)-alkylsulfonyl, ($C_6$-$C_{16}$)-arylmercapto, ($C_6$-$C_{16}$)-arylsulfinyl, ($C_6$-$C_{16}$)-arylsulfonyl, ($C_7$-$C_{16}$)-aralkylmercapto, ($C_7$-$C_{16}$)-aralkylsulfinyl, or ($C_7$-$C_{16}$)-aralkylsulfonyl;

or wherein $R^1$ and $R^2$, or $R^2$ and $R^3$ form a chain $[CH_2]_o$, which is saturated or unsaturated by a C=C double bond, in which 1 or 2 $CH_2$ groups are optionally replaced by O, S, SO, $SO_2$, or NR', and R' is hydrogen, ($C_6$-$C_{12}$)-aryl, ($C_1$-$C_8$)-alkyl, ($C_1$-$C_8$)-alkoxy-($C_1$-$C_8$)-alkyl, ($C_7$-$C_{12}$)-aralkoxy-($C_1$-$C_8$)-alkyl, ($C_6$-$C_{12}$)-aryloxy-($C_1$-$C_8$)-alkyl, ($C_1$-$C_{10}$)-alkanoyl, optionally substituted ($C_7$-$C_{16}$)-aralkanoyl, or optionally substituted ($C_6$-$C_{12}$)-aroyl; and o is 3, 4 or 5;

or wherein the radicals $R^1$ and $R^2$, or $R^2$ and $R^3$, together with the pyridine or pyridazine carrying them, form a 5,6,7,8-tetrahydroisoquinoline ring, a 5,6,7,8-tetrahydroquinoline ring, or a 5,6,7,8-tetrahydrocinnoline ring;

or wherein $R^1$ and $R^2$, or $R^2$ and $R^3$ form a carbocyclic or heterocyclic 5- or 6-membered aromatic ring;

or where $R^1$ and $R^2$, or $R^2$ and $R^3$, together with the pyridine or pyridazine carrying them, form an optionally substituted heterocyclic ring systems selected from thienopyridines, furanopyridines, pyridopyridines, pyrimidinopyridines, imidazopyridines, thiazolopyridines, oxazolopyridines, quinoline, isoquinoline, and cinnoline; where quinoline, isoquinoline or cinnoline preferably satisfy the formulae Ia, Ib and Ic:

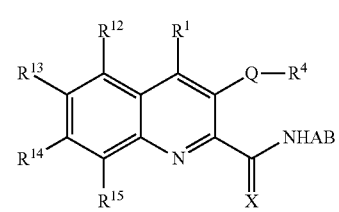

(Ia)

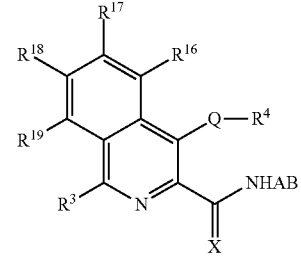

(Ib)

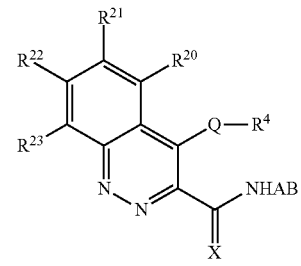

(Ic)

and the substituents $R^{12}$ to $R^{23}$ in each case independently of each other have the meaning of $R^1$, $R^2$ and $R^3$;

or wherein the radicals $R^1$ and $R^2$, together with the pyridine carrying them, form a compound of Formula Id:

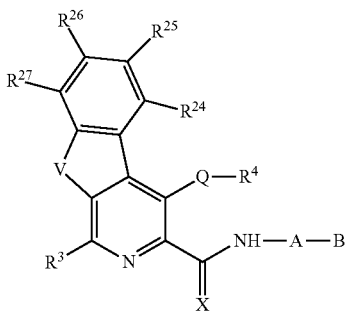

(Id)

where V is S, O, or NR$^k$, and R$^k$ is selected from hydrogen, (C$_1$-C$_6$)-alkyl, aryl, or benzyl; where an aryl radical may be optionally substituted by 1 to 5 substituents as defined above; and
R$^{24}$, R$^{25}$, R$^{26}$, and R$^{27}$ in each case independently of each other have the meaning of R$^1$, R$^2$ and R$^3$;
f is 1 to 8;
g is 0 or 1 to (2f+1);
x is 0 to 3; and
h is 3 to 7;
including the physiologically active salts and prodrugs derived therefrom.

Exemplary compounds according to Formula (I) are described in European Patent Nos. EP0650960 and EP0650961. All compounds listed in EP0650960 and EP0650961, in particular, those listed in the compound claims and the final products of the working examples, are hereby incorporated into the present application by reference herein. Exemplary compounds of Formula (I) include, but are not limited to, [(3-Hydroxy-pyridine-2-carbonyl)-amino]-acetic acid and [(3-methoxy-pyridine-2-carbonyl)-amino]-acetic acid.

Additionally, exemplary compounds according to Formula (I) are described in U.S. Pat. No. 5,658,933. All compounds listed in U.S. Pat. No. 5,658,933, in particular, those listed in the compound claims and the final products of the working examples, are hereby incorporated into the present application by reference herein. Exemplary compounds of Formula (I) include, but are not limited to, 3-methoxypyridine-2-carboxylic acid N-(((hexadecyloxy)-carbonyl)-methyl)-amide hydrochloride, 3-methoxypyridine-2-carboxylic acid N-(((1-octyloxy)-carbonyl)-methyl)-amide, 3-methoxypyridine-2-carboxylic acid N-(((hexyloxy)-carbonyl)-methyl)-amide, 3-methoxypyridine-2-carboxylic acid N-(((butyloxy)-carbonyl)-methyl)-amide, 3-methoxypyridine-2-carboxylic acid N-(((2-nonyloxy)-carbonyl)-methyl)-amide racemate, 3-methoxypyridine-2-carboxylic acid N-(((heptyloxy)-carbonyl)-methyl)-amide, 3-benzyloxypyridine-2-carboxylic acid N-(((octyloxy)-carbonyl)-methyl)-amide, 3-benzyloxy-pyridine-2-carboxylic acid N-(((butyloxy)-carbonyl)-methyl)-amide, 5-(((3-(1-butyloxy)-propyl)-amino)-carbonyl)-3-methoxypyridine-2-carboxylic acid N-((benzyloxycarbonyl)-methyl)-amide, 5-(((3-(1-butyloxy)-propyl)-amino)-carbonyl)-3-methoxypyridine-2-carboxylic acid N-(((1-butyloxy)-carbonyl)-methyl)-amide, and 5-(((3-lauryloxy)-propyl)amino)-carbonyl)-3-methoxypyridine-2-carboxylic acid N-(((benzyloxy)-carbonyl)-methyl)-amide.

Additional compounds according to Formula (I) are substituted heterocyclic carboxyamides described in U.S. Pat. No. 5,620,995; 3-hydroxypyridine-2-carboxamidoesters described in U.S. Pat. No. 6,020,350; sulfonamidocarbonylpyridine-2-carboxamides described in U.S. Pat. No. 5,607,954; and sulfonamidocarbonyl-pyridine-2-carboxamides and sulfonamidocarbonyl-pyridine-2-carboxamide esters described in U.S. Pat. Nos. 5,610,172 and 5,620,996. All compounds listed in these patents, in particular, those compounds listed in the compound claims and the final products of the working examples, are hereby incorporated into the present application by reference herein.

Exemplary compounds according to Formula (Ia) are described in U.S. Pat. Nos. 5,719,164 and 5,726,305. All compounds listed in the foregoing patents, in particular, those listed in the compound claims and the final products of the working examples, are hereby incorporated into the present application by reference herein. Exemplary compounds of Formula (Ia) include, but are not limited to, N-((3-hydroxy-6-isopropoxy-quinoline-2-carbonyl)-amino)-acetic acid, N-((6-(1-butyloxy)-3-hydroxyquinolin-2-yl)-carbonyl)-glycine, [(3-hydro-6-trifluoromethoxy-quinoline-2-carbonyl)-amino]-acetic acid, N-((6-chloro-3-hydroxyquinolin-2-yl)-carbonyl)-glycine, N-((7-chloro-3-hydroxyquinolin-2-yl)-carbonyl)-glycine, and [(6-chloro-3-hydroxy-quinoline-2-carbonyl)-amino]-acetic acid.

Exemplary compounds according to Formula (Ib) are described in U.S. Pat. No. 6,093,730. All compounds listed in U.S. Pat. No. 6,093,730, in particular, those listed in the compound claims and the final products of the working examples, are hereby incorporated into the present application by reference herein. Exemplary compounds of Formula (Ib) include, but are not limited to, N-((1-chloro-4-hydroxy-7-(2-propyloxy) isoquinolin-3-yl)-carbonyl)-glycine, N-((1-chloro-4-hydroxy-6-(2-propyloxy) isoquinolin-3-yl)-carbonyl)-glycine, N-((1-chloro-4-hydroxy-isoquinoline-3-carbonyl)-amino)-acetic acid (compound A), N-((1-chloro-4-hydroxy-7-methoxyisoquinolin-3-yl)-carbonyl)-glycine, N-((1-chloro-4-hydroxy-6-methoxyisoquinolin-3-yl)-carbonyl)-glycine, N-((7-butyloxy)-1-chloro-4-hydroxyisoquinolin-3-yl)-carbonyl)-glycine, N-((6-benzyloxy-1-chloro-4-hydroxy-isoquinoline-3-carbonyl)-amino)-acetic acid, ((7-benzyloxy-1-chloro-4-hydroxy-isoquinoline-3-carbonyl)-amino)-acetic acid methyl ester, N-((7-benzyloxy-1-chloro-4-hydroxy-isoquinoline-3-carbonyl)-amino)-acetic acid, N-((8-chloro-4-hydroxyisoquinolin-3-yl)-carbonyl)-glycine, N-((7-butoxy-4-hydroxy-isoquinoline-3-carbonyl)-amino)-acetic acid.

Additionally, compounds related to Formula (I) that can also be used in the methods of the invention include, but are not limited to, 6-cyclohexyl-1-hydroxy-4-methyl-1H-pyridin-2-one, 7-(4-methyl-piperazin-1-ylmethyl)-5-phenylsulfanylmethyl-quinolin-8-ol, 4-nitro-quinolin-8-ol, 5-butoxymethyl-quinolin-8-ol, [(4-Hydroxy-7-phenoxy-isoquinoline-3-carbonyl)-amino]-acetic acid (compound B), and [(4-Hydroxy-7-phenylsulfanyl-isoquinoline-3-carbonyl)-amino]-acetic acid (compound C). Further, the invention provides additional exemplary compounds wherein, e.g., position A and B together may be, e.g., hexanoic acid, cyanomethyl, 2-aminoethyl, benzoic acid, 1H-benzoimidazol-2-ylmethyl, etc.

In other embodiments, compounds used in the methods of the invention are selected from a compound of the formula (III)

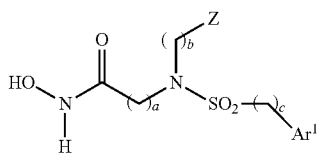

(III)

or pharmaceutically acceptable salts thereof, wherein:
a is an integer from 1 to 4;
b is an integer from 0 to 4;
c is an integer from 0 to 4;
Z is selected from the group consisting of $(C_3-C_{10})$ cycloalkyl, $(C_3-C_{10})$ cycloalkyl independently substituted with one or more $Y^1$, 3-10 membered heterocycloalkyl and 3-10 membered heterocycloalkyl independently substituted with one or more $Y^1$; $(C_5-C_{20})$ aryl, $(C_5-C_{20})$ aryl independently substituted with one or more $Y^1$, 5-20 membered heteroaryl and 5-20 membered heteroaryl independently substituted with one or more $Y^1$;
$Ar^1$ is selected from the group consisting of $(C_5-C_{20})$ aryl, $(C_5-C_{20})$ aryl independently substituted with one or more $Y^2$, 5-20 membered heteroaryl and 5-20 membered heteroaryl independently substituted with one or more $Y^2$;
each $Y^1$ is independently selected from the group consisting of a lipophilic functional group, $(C_5-C_{20})$ aryl, $(C_6-C_{26})$ alkaryl, 5-20 membered heteroaryl and 6-26 membered alk-heteroaryl;
each $Y^2$ is independently selected from the group consisting of —R', —OR', —OR", —SW, —SR", —NR'R', —NO$_2$, —CN, -halogen, -trihalomethyl, trihalomethoxy, —C(O)R', —C(O)OR', —C(O)NR'R', —C(O)NR'OR', —C(NR'R')=NOR', —NR'—C(O)R', —SO$_2$R', —SO$_2$R", —NR'—SO$_2$—R', —NR'—C(O)—NR'R', tetrazol-5-yl, —NR'—C(O)—OR', —C(NR'R')=NR', —S(O)—R', —S(O)—R", and —NR'—C(S)—NR'R'; and
each R' is independently selected from the group consisting of —H, $(C_1-C_8)$ alkyl, $(C_2-C_8)$ alkenyl, and $(C_2-C_8)$ alkynyl; and
each R" is independently selected from the group consisting of $(C_5-C_{20})$ aryl and $(C_5-C_{20})$ aryl independently substituted with one or more —OR', —SR', —NR'R', —NO$_2$, —CN, halogen or trihalomethyl groups,
or wherein c is 0 and $Ar^1$ is an N' substituted urea-aryl, the compound has the structural formula (IIIa):

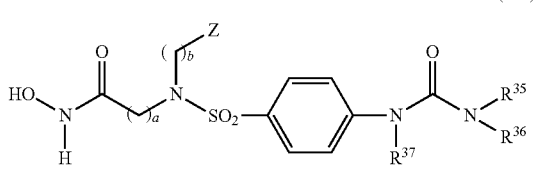

(IIIa)

or pharmaceutically acceptable salts thereof, wherein:
a, b, and Z are as defined above; and
$R^{35}$ and $R^{36}$ are each independently selected from the group consisting of hydrogen, $(C_1-C_8)$ alkyl, $(C_2-C_8)$ alkenyl, $(C_2-C_8)$ alkynyl, $(C_3-C_{10})$ cycloalkyl, $(C_5-C_{20})$ aryl, $(C_5-C_{20})$ substituted aryl, $(C_6-C_{26})$ alkaryl, $(C_6-C_{26})$ substituted alkaryl, 5-20 membered heteroaryl, 5-20 membered substituted heteroaryl, 6-26 membered alk-heteroaryl, and 6-26 membered substituted alk-heteroaryl; and $R^{37}$ is independently selected from the group consisting of hydrogen, $(C_1-C_8)$ alkyl, $(C_2-C_8)$ alkenyl, and $(C_2-C_8)$ alkynyl.

Exemplary compounds of Formula (III) are described in International Publication No. WO 00/50390. All compounds listed in WO 00/50390, in particular, those listed in the compound claims and the final products of the working examples, are hereby incorporated into the present application by reference herein. Exemplary compounds of Formula (III) include 3-{[4-(3,3-dibenzyl-ureido)-benzenesulfonyl]-[2-(4-methoxy-phenyl)-ethyl]-amino}-N-hydroxy-propionamide (compound D), 3-{{4-[3-(4-chloro-phenyl)-ureido]-benzenesulfonyl}-[2-(4-methoxy-phenyl)-ethyl]-amino}-N-hydroxy-propionamide, and 3-{{4-[3-(1,2-diphenyl-ethyl)-ureido]-benzenesulfonyl}-[2-(4-methoxy-phenyl)-ethyl]-amino}-N-hydroxy-propionamide.

Methods for identifying compounds of the invention are also provided. In certain aspects, a compound of the invention is one that stabilizes HIFα. The ability of a compound to stabilize or activate HIFα can be measured, for example, by direct measurement of HIFα in a sample, indirect measurement of HIFα, e.g., by measuring a decrease in HIFα associated with the von Hippel Lindau protein (see, e.g., International Publication No. WO 00/69908), or activation of HIF responsive target genes or reporter constructs (see, e.g., U.S. Pat. No. 5,942,434). Measuring and comparing levels of HIF and/or HIF-responsive target proteins in the absence and presence of the compound will identify compounds that stabilize HIFα and/or activate HIF.

In other aspects, a compound of the invention is one that inhibits HIF hydroxylase activity. Assays for hydroxylase activity are standard in the art. Such assays can directly or indirectly measure hydroxylase activity. For example, an assay can measure hydroxylated residues, e.g., proline, asparagine, etc., present in the enzyme substrate, e.g., a target protein, a synthetic peptide mimetic, or a fragment thereof. (See, e.g., Palmerini et al. (1985) J Chromatogr 339:285-292.) A reduction in hydroxylated residue, e.g., proline or asparagine, in the presence of a compound is indicative of a compound that inhibits hydroxylase activity. Alternatively, assays can measure other products of the hydroxylation reaction, e.g., formation of succinate from 2-oxoglutarate. (See, e.g., Cunliffe et al. (1986) Biochem J 240:617-619.) Kaule and Gunzler (1990; Anal Biochem 184:291-297) describe an exemplary procedure that measures production of succinate from 2-oxoglutarate.

Procedures such as those described above can be used to identify compounds that modulate HIF hydroxylase activity. Target protein may include HIFα or a fragment thereof, e.g., HIF(556-575). Enzyme may include, e.g., HIF prolyl hydroxylase (see, e.g., GenBank Accession No. AAG33965, etc.) or HIF asparaginyl hydroxylase (see, e.g., GenBank Accession No. AAL27308, etc.), obtained from any source. Enzyme may also be present in a crude cell lysate or in a partially purified form. For example, procedures that measure HIF hydroxylase activity are described in Ivan et al. (2001, Science 292:464-468; and 2002, Proc Natl Acad Sci USA 99:13459-13464) and Hirsila et al. (2003, J Biol Chem 278:30772-30780); additional methods are described in International Publication No. WO 03/049686. Measuring and comparing enzyme activity in the absence and presence of the compound will identify compounds that inhibit hydroxylation of HIFα.

A compound of the invention is one that further produces a measurable effect, as measured in vitro or in vivo, as demonstrated by enhanced erythropoiesis, enhanced iron metabolism, or therapeutic improvement of conditions including, e.g., iron deficiency, including functional iron deficiency; anemia of chronic disease, iron deficiency, and microcytosis or microcytic anemia; or a condition associated with inflammation, infection, immunodeficiency, or neoplastic disorder.

The measurable effect can be any one of the following parameters: increased hemoglobin, hematocrit, reticulocyte, red blood cell count, plasma EPO, etc.; improved iron metabolism, as measured by lessening of observed symptoms, including, e.g., mitigation of chronic fatigue, pallor, dizziness, etc., or by increased serum iron levels, altered serum ferritin levels, % transferrin saturation, total iron binding capacity, improved reticulocyte counts, hemoglobin, hematocrit, e.g., all as measured by standard blood count analysis.

Pharmaceutical Formulations and Routes of Administration

The compositions of the present invention can be delivered directly or in pharmaceutical compositions containing excipients, as is well known in the art. Present methods of treatment can comprise administration of an effective amount of a compound of the present invention to a subject having or at risk for a metabolic disorder; particularly a disorder associated with glucose regulation, e.g., diabetes, hyperglycemia, etc. In a preferred embodiment, the subject is a mammalian subject, and in a most preferred embodiment, the subject is a human subject.

An effective amount, e.g., dose, of compound or drug can readily be determined by routine experimentation, as can an effective and convenient route of administration and an appropriate formulation. Various formulations and drug delivery systems are available in the art. (See, e.g., Gennaro, ed. (2000) Remington's Pharmaceutical Sciences, supra; and Hardman, Limbird, and Gilman, eds. (2001) The Pharmacological Basis of Therapeutics, supra.)

Suitable routes of administration may, for example, include oral, rectal, topical, nasal, pulmonary, ocular, intestinal, and parenteral administration. Primary routes for parenteral administration include intravenous, intramuscular, and subcutaneous administration. Secondary routes of administration include intraperitoneal, intra-arterial, intra-articular, intracardiac, intracisternal, intradermal, intralesional, intraocular, intrapleural, intrathecal, intrauterine, and intraventricular administration. The indication to be treated, along with the physical, chemical, and biological properties of the drug, dictate the type of formulation and the route of administration to be used, as well as whether local or systemic delivery would be preferred.

Pharmaceutical dosage forms of a compound of the invention may be provided in an instant release, controlled release, sustained release, or target drug-delivery system. Commonly used dosage forms include, for example, solutions and suspensions, (micro-) emulsions, ointments, gels and patches, liposomes, tablets, dragees, soft or hard shell capsules, suppositories, ovules, implants, amorphous or crystalline powders, aerosols, and lyophilized formulations. Depending on route of administration used, special devices may be required for application or administration of the drug, such as, for example, syringes and needles, inhalers, pumps, injection pens, applicators, or special flasks. Pharmaceutical dosage forms are often composed of the drug, an excipient(s), and a container/closure system. One or multiple excipients, also referred to as inactive ingredients, can be added to a compound of the invention to improve or facilitate manufacturing, stability, administration, and safety of the drug, and can provide a means to achieve a desired drug release profile. Therefore, the type of excipient(s) to be added to the drug can depend on various factors, such as, for example, the physical and chemical properties of the drug, the route of administration, and the manufacturing procedure. Pharmaceutically acceptable excipients are available in the art, and include those listed in various pharmacopoeias. (See, e.g., USP, JP, EP, and BP, FDA web page (www.fda.gov), Inactive Ingredient Guide 1996, and Handbook of Pharmaceutical Additives, ed. Ash; Synapse Information Resources, Inc. 2002.)

Pharmaceutical dosage forms of a compound of the present invention may be manufactured by any of the methods well-known in the art, such as, for example, by conventional mixing, sieving, dissolving, melting, granulating, dragee-making, tabletting, suspending, extruding, spray-drying, levigating, emulsifying, (nano/micro-) encapsulating, entrapping, or lyophilization processes. As noted above, the compositions of the present invention can include one or more physiologically acceptable inactive ingredients that facilitate processing of active molecules into preparations for pharmaceutical use.

Proper formulation is dependent upon the desired route of administration. For intravenous injection, for example, the composition may be formulated in aqueous solution, if necessary using physiologically compatible buffers, including, for example, phosphate, histidine, or citrate for adjustment of the formulation pH, and a tonicity agent, such as, for example, sodium chloride or dextrose. For transmucosal or nasal administration, semisolid, liquid formulations, or patches may be preferred, possibly containing penetration enhancers. Such penetrants are generally known in the art. For oral administration, the compounds can be formulated in liquid or solid dosage forms and as instant or controlled/sustained release formulations. Suitable dosage forms for oral ingestion by a subject include tablets, pills, dragees, hard and soft shell capsules, liquids, gels, syrups, slurries, suspensions, and emulsions. The compounds may also be formulated in rectal compositions, such as suppositories or retention enemas, e.g., containing conventional suppository bases such as cocoa butter or other glycerides.

Solid oral dosage forms can be obtained using excipients, which may include, fillers, disintegrants, binders (dry and wet), dissolution retardants, lubricants, glidants, antiadherants, cationic exchange resins, wetting agents, antioxidants, preservatives, coloring, and flavoring agents. These excipients can be of synthetic or natural source. Examples of such excipients include cellulose derivatives, citric acid, dicalcium phosphate, gelatine, magnesium carbonate, magnesium/sodium lauryl sulfate, mannitol, polyethylene glycol, polyvinyl pyrrolidone, silicates, silicium dioxide, sodium benzoate, sorbitol, starches, stearic acid or a salt thereof, sugars (i.e. dextrose, sucrose, lactose, etc.), talc, tragacanth mucilage, vegetable oils (hydrogenated), and waxes. Ethanol and water may serve as granulation aides. In certain instances, coating of tablets with, for example, a taste-masking film, a stomach acid resistant film, or a release-retarding film is desirable. Natural and synthetic polymers, in combination with colorants, sugars, and organic solvents or water, are often used to coat tablets, resulting in dragees. When a capsule is preferred over a tablet, the drug powder, suspension, or solution thereof can be delivered in a compatible hard or soft shell capsule.

In one embodiment, the compounds of the present invention can be administered topically, such as through a skin patch, a semi-solid or a liquid formulation, for example a gel, a (micro-) emulsion, an ointment, a solution, a (nano/micro)-suspension, or a foam. The penetration of the drug into the skin and underlying tissues can be regulated, for example, using penetration enhancers; the appropriate choice and combination of lipophilic, hydrophilic, and amphiphilic excipients, including water, organic solvents, waxes, oils, synthetic and natural polymers, surfactants, emulsifiers; by pH adjustment; and use of complexing agents. Other techniques, such as iontophoresis, may be used to regulate skin penetration of a compound of the invention. Transdermal or topical administration would be preferred, for example, in situations in which local delivery with minimal systemic exposure is desired.

For administration by inhalation, or administration to the nose, the compounds for use according to the present invention are conveniently delivered in the form of a solution, suspension, emulsion, or semisolid aerosol from pressurized packs, or a nebuliser, usually with the use of a propellant, e.g., halogenated carbons derived from methan and ethan, carbon dioxide, or any other suitable gas. For topical aerosols, hydrocarbons like butane, isobutene, and pentane are useful. In the case of a pressurized aerosol, the appropriate dosage unit may be determined by providing a valve to deliver a metered amount. Capsules and cartridges of, for example, gelatin, for use in an inhaler or insufflator, may be formulated. These typically contain a powder mix of the compound and a suitable powder base such as lactose or starch.

Compositions formulated for parenteral administration by injection are usually sterile and, can be presented in unit dosage forms, e.g., in ampoules, syringes, injection pens, or in multi-dose containers, the latter usually containing a preservative. The compositions may take such forms as suspensions, solutions, or emulsions in oily or aqueous vehicles, and may contain formulatory agents, such as buffers, tonicity agents, viscosity enhancing agents, surfactants, suspending and dispersing agents, antioxidants, biocompatible polymers, chelating agents, and preservatives. Depending on the injection site, the vehicle may contain water, a synthetic or vegetable oil, and/or organic co-solvents. In certain instances, such as with a lyophilized product or a concentrate, the parenteral formulation would be reconstituted or diluted prior to administration. Depot formulations, providing controlled or sustained release of a compound of the invention, may include injectable suspensions of nano/micro particles or nano/micro or non-micronized crystals. Polymers such as poly(lactic acid), poly(glycolic acid), or copolymers thereof, can serve as controlled/sustained release matrices, in addition to others well known in the art. Other depot delivery systems may be presented in form of implants and pumps requiring incision.

Suitable carriers for intravenous injection for the molecules of the invention are well-known in the art and include water-based solutions containing a base, such as, for example, sodium hydroxide, to form an ionized compound, sucrose or sodium chloride as a tonicity agent, for example, the buffer contains phosphate or histidine. Co-solvents, such as, for example, polyethylene glycols, may be added. These water-based systems are effective at dissolving compounds of the invention and produce low toxicity upon systemic administration. The proportions of the components of a solution system may be varied considerably, without destroying solubility and toxicity characteristics. Furthermore, the identity of the components may be varied. For example, low-toxicity surfactants, such as polysorbates or poloxamers, may be used, as can polyethylene glycol or other co-solvents, biocompatible polymers such as polyvinyl pyrrolidone may be added, and other sugars and polyols may substitute for dextrose.

For composition useful for the present methods of treatment, a therapeutically effective dose can be estimated initially using a variety of techniques well-known in the art. Initial doses used in animal studies may be based on effective concentrations established in cell culture assays. Dosage ranges appropriate for human subjects can be determined, for example, using data obtained from animal studies and cell culture assays.

A therapeutically effective dose or amount of a compound, agent, or drug of the present invention refers to an amount or dose of the compound, agent, or drug that results in amelioration of symptoms or a prolongation of survival in a subject. Toxicity and therapeutic efficacy of such molecules can be determined by standard pharmaceutical procedures in cell cultures or experimental animals, e.g., by determining the LD50 (the dose lethal to 50% of the population) and the ED50 (the dose therapeutically effective in 50% of the population). The dose ratio of toxic to therapeutic effects is the therapeutic index, which can be expressed as the ratio LD50/ED50. Agents that exhibit high therapeutic indices are preferred.

The effective amount or therapeutically effective amount is the amount of the compound or pharmaceutical composition that will elicit the biological or medical response of a tissue, system, animal, or human that is being sought by the researcher, veterinarian, medical doctor, or other clinician, e.g., regulation of glucose metabolism, decrease in elevated or increased blood glucose levels, treatment or prevention of a disorder associated with altered glucose metabolism, e.g., diabetes, etc Dosages preferably fall within a range of circulating concentrations that includes the ED50 with little or no toxicity. Dosages may vary within this range depending upon the dosage form employed and/or the route of administration utilized. The exact formulation, route of administration, dosage, and dosage interval should be chosen according to methods known in the art, in view of the specifics of a subject's condition.

Dosage amount and interval may be adjusted individually to provide plasma levels of the active moiety that are sufficient to achieve the desired effects, e.g., regulation of glucose metabolism, decrease in blood glucose levels, etc., i.e., minimal effective concentration (MEC). The MEC will vary for each compound but can be estimated from, for example, in vitro data and animal experiments. Dosages necessary to achieve the MEC will depend on individual characteristics and route of administration. In cases of local administration or selective uptake, the effective local concentration of the drug may not be related to plasma concentration.

The amount of agent or composition administered may be dependent on a variety of factors, including the sex, age, and weight of the subject being treated, the severity of the affliction, the manner of administration, and the judgment of the prescribing physician.

The present compositions may, if desired, be presented in a pack or dispenser device containing one or more unit dosage forms containing the active ingredient. Such a pack or device may, for example, comprise metal or plastic foil, such as a blister pack, or glass and rubber stoppers such as in vials. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

These and other embodiments of the present invention will readily occur to those of ordinary skill in the art in view of the disclosure herein.

EXAMPLES

The invention will be further understood by reference to the following examples, which are intended to be purely exemplary of the invention. These examples are provided solely to illustrate the claimed invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description and accompanying figures. Such modifications are intended to fall within the scope of the appended claims.

Example 1: Overcoming Suppressive Effects of TNF-α on EPO Production

Hep3B cells were treated with various concentrations (0, 0.4, 2, 10 ng/ml) of TNF-α in the absence or presence of compound A or compound B for 3 days. Secreted EPO levels were determined using a commercially available ELISA kit (R&D Systems, catalog no. DEP00). In the absence of compound, treatment of Hep3B cells with TNF-α reduced EPO production in a dose-dependent manner Hep3B cells treated with various concentrations of either compound A (FIG. 1A) or compound B (FIG. 1B) in the absence of TNF-α showed a dose-dependent increase in EPO production. Addition of either compound in the presence of TNF-α greatly reduced the inhibitory effects of TNF-α on EPO production. Overcoming the suppressive effect of TNF-α on EPO production by prolyl hydroxylase inhibition was observed in the presence of low (e.g., 0.4 ng/ml) and high (e.g., 10 ng/ml) concentrations of TNF-α. Therefore, inhibitory effects of the inflammatory cytokine TNF-α on EPO production were overcome by inhibition of prolyl hydroxylase activity using compounds and methods of the present invention. These results suggested that compounds and methods of the present invention are useful for increasing EPO production in the presence of the inflammatory cytokine TNF-α. Further, the methods and compounds of the present invention are useful to increase EPO production and, therefore, to treat anemia in a subject, for example, wherein the subject has a disorder associated with TNF-α☐ such as acute or chronic inflammation or other anemia of chronic disease.

A series of experiments were performed to examine the effects of compounds of the present invention on EPO production following exposure of cells to the inflammatory cytokine TNF-α (i.e., in cells already exposed to TNF-α). In these experiments, TNF-α signaling would therefore be initiated prior to the addition of a prolyl hydroxylase inhibitor. Hep3B cells were treated with various concentrations (0, 0.4, 2, 10 ng/ml) of TNF-α for 2 hours, after which various concentrations of compound A or compound B were added to the cultured cells. Secreted EPO levels were determined as described above 3 days following compound addition.

Figure 2A:
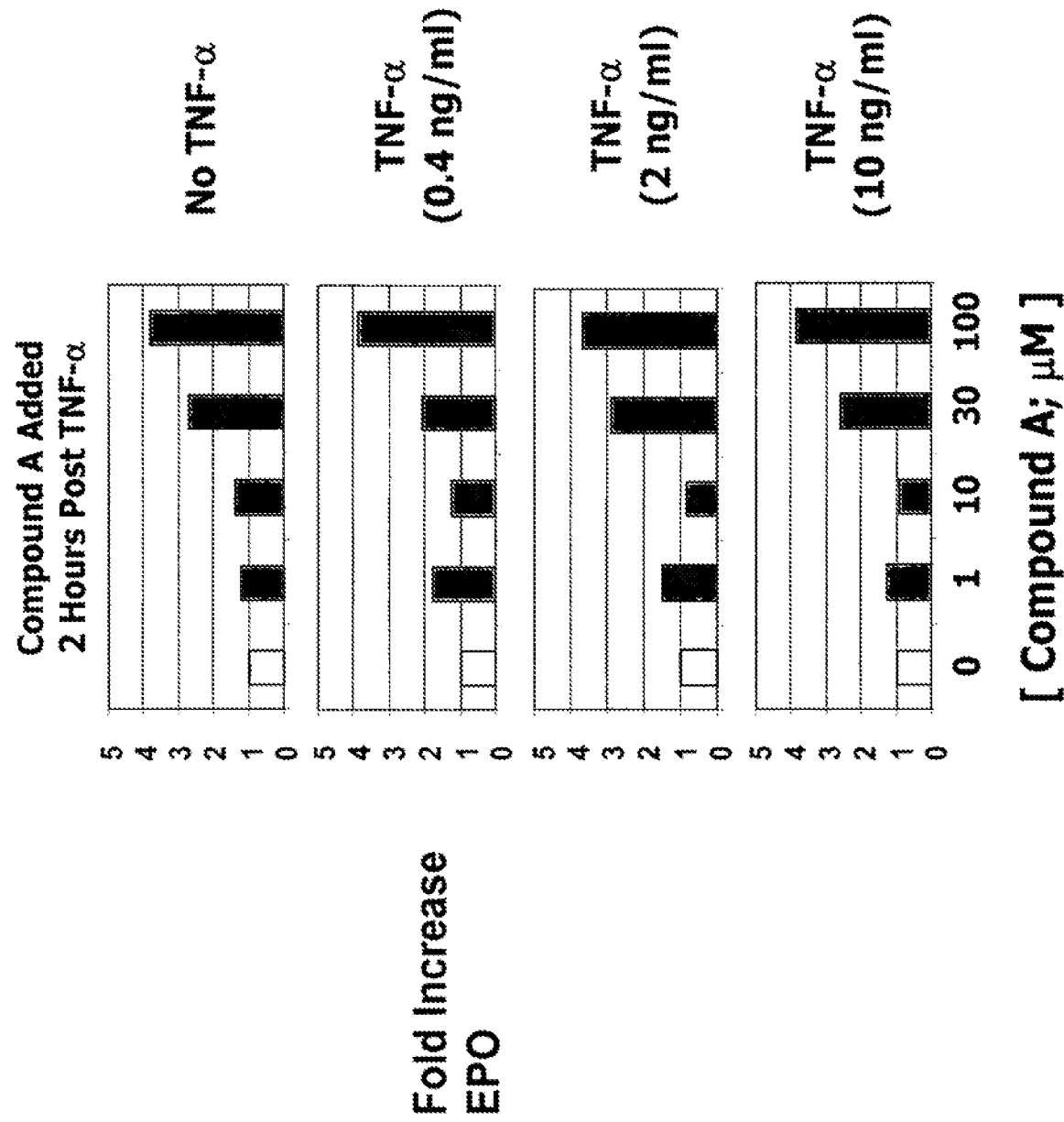
FIGS. 2A and 2B set forth data showing methods and compounds of the present invention overcome the suppressive effects of TNF-α on EPO production in cells pre-treated with TNF-α.
Figure 2B:
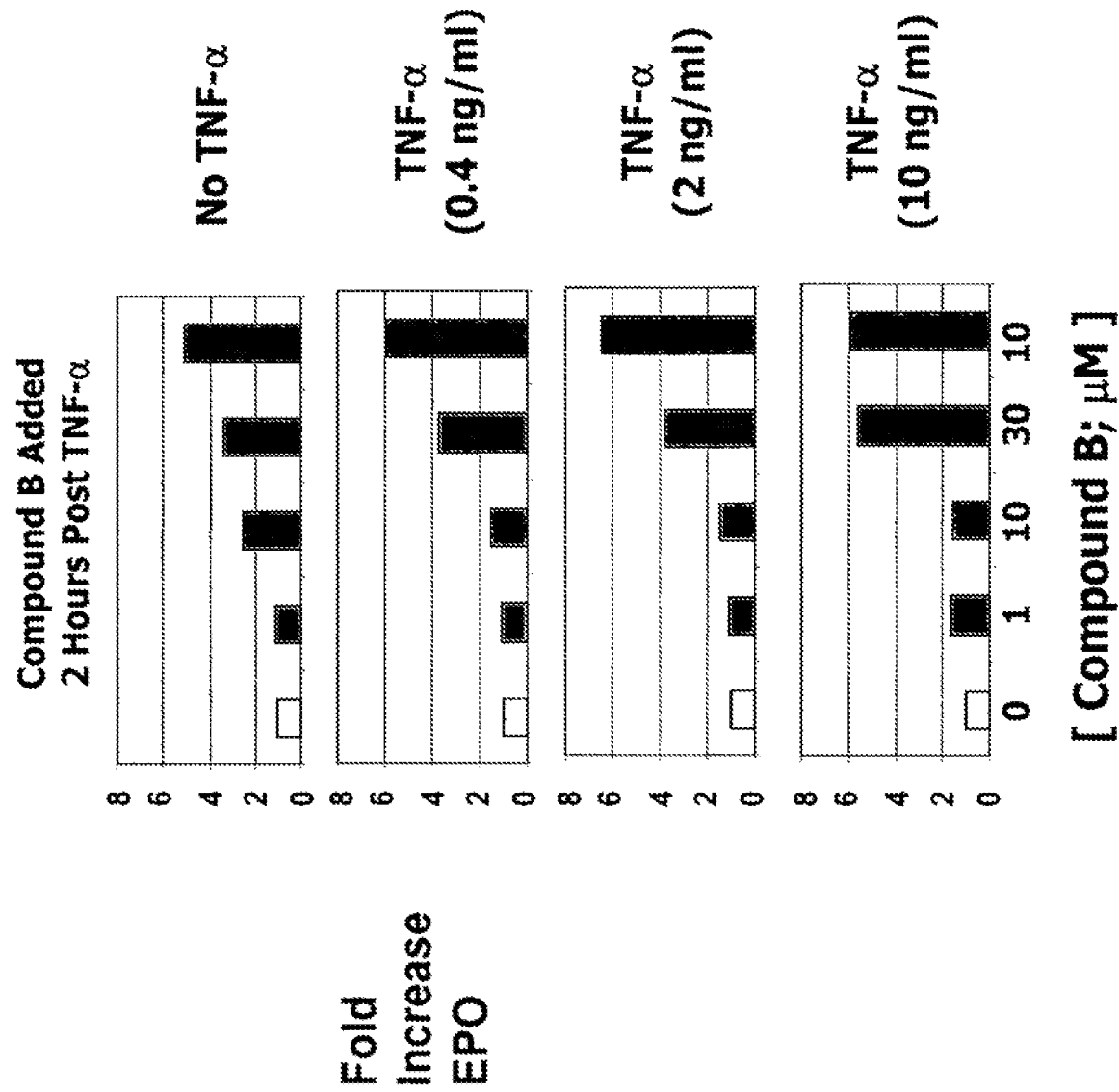
Figure 3A:
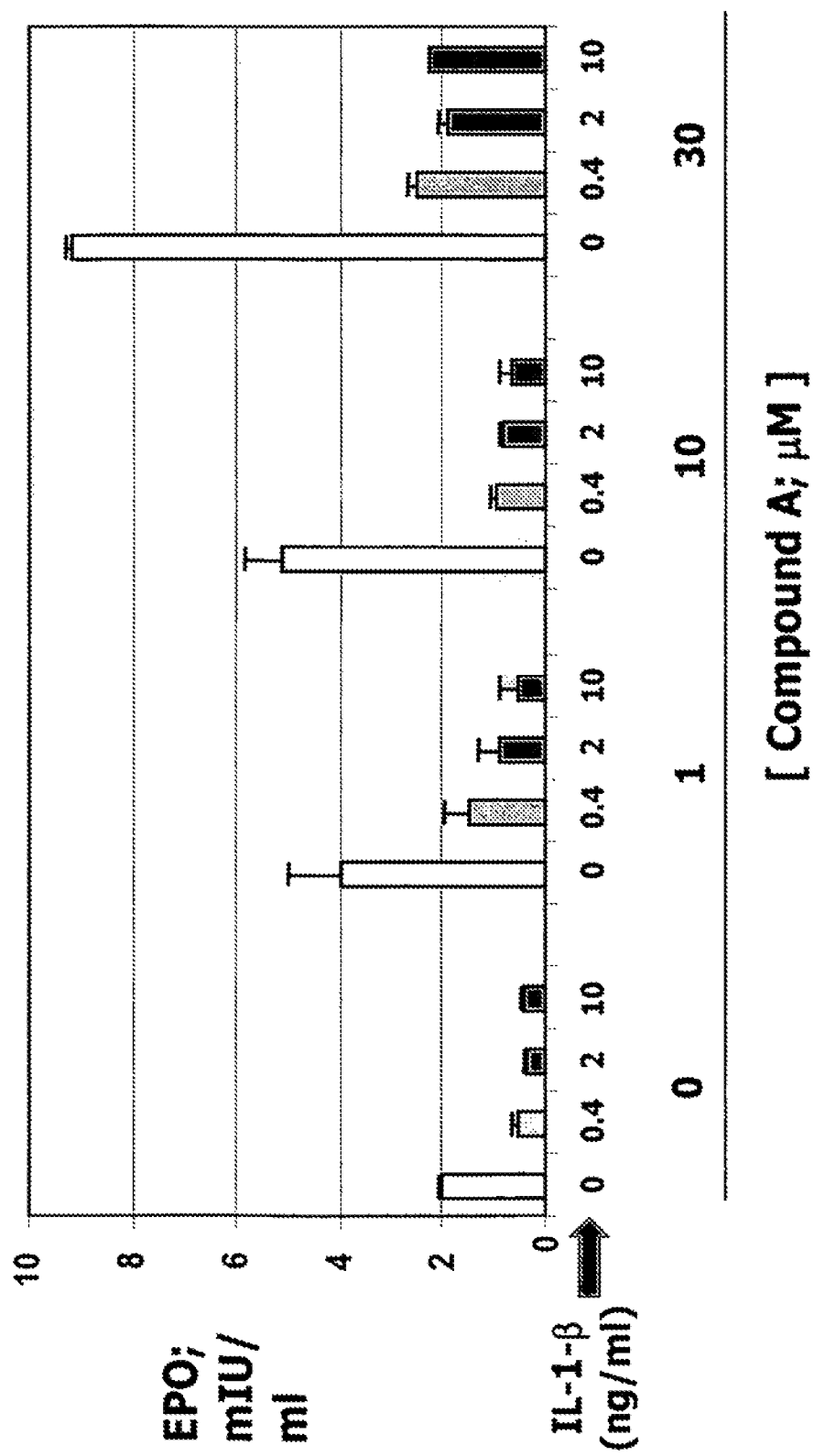
FIGS. 3A and 3B set forth data showing methods and compounds of the present invention overcome the suppressive effects of IL-β on EPO production.
Figure 3B:
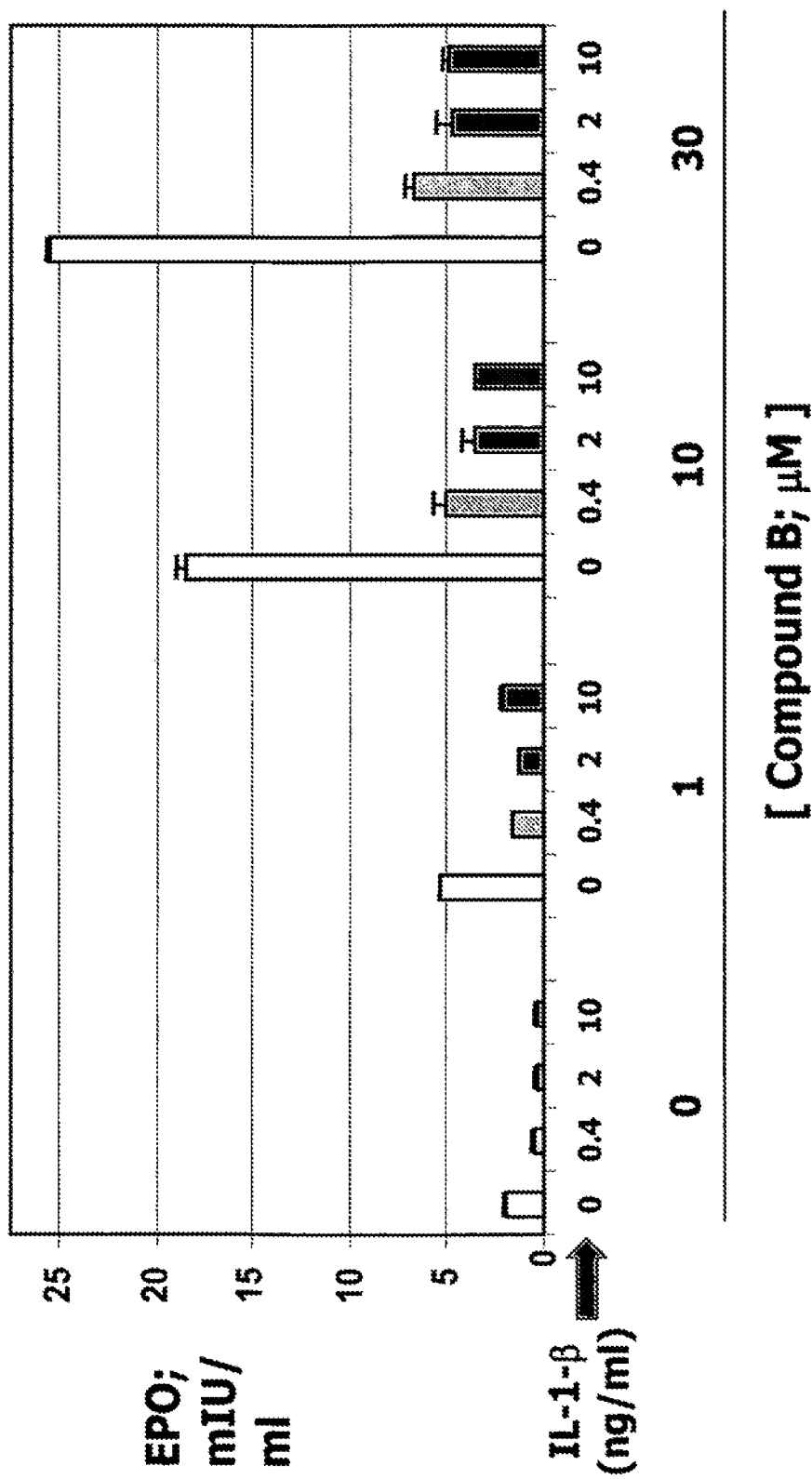

As shown in FIGS. 2A and 2B, compound A and compound B overcame the suppressive effects of TNF-α on EPO production following a 2-hour pre-treatment of Hep3B cells with TNF-α. This data indicated that compounds and methods of the present invention are useful for increasing EPO production in cells exposed to TNF-α. These results also suggested that treatment with compound of the present invention provides useful means to increase EPO production and treat anemia in a subject in which EPO production has been suppressed by TNF-α.

Addition of compounds of the present invention greatly reduced the inhibitory effects of TNF-α on EPO production. Therefore, compounds and methods of the present invention are useful for treating or preventing anemia of associated with increased TNF-α, e.g., inflammatory disorders.

Example 2: Overcoming Suppressive Effects of IL-1β on EPO Production

Hep3B cells were treated with various concentrations (0, 0.4, 2, 10 ng/ml) of IL-1β in the absence or presence of compound A or compound B for 3 days. Secreted EPO levels were determined using a commercially available ELISA kit (R&D Systems, catalog no. DEP00). In the absence of compound, treatment of Hep3B cells with IL-1β reduced EPO production in a dose-dependent manner Hep3B cells treated with various concentrations of either compound A (FIG. 3A) or compound B (FIG. 3B) in the absence of IL-1β showed a dose-dependent increase in EPO production. Addition of either compound in the presence of IL-1β greatly reduced the inhibitory effects of IL-1β on EPO production. Overcoming the suppressive effects of IL-1β on EPO production by prolyl hydroxylase inhibition was observed in the presence of low (e.g., 0.4 ng/ml) and high (e.g., 10 ng/ml) concentrations of IL-1β. Therefore, inhibitory effects of the inflammatory cytokine IL-1β on EPO production were overcome by inhibition of prolyl hydroxylase activity using compounds and methods of the present invention. These results suggested that compounds and methods of the present invention are useful for increasing EPO production in the presence of the inflammatory cytokine IL-1β. Further, the methods and compounds of the present invention are useful to increase EPO production and, therefore, to treat anemia in a subject, for example, wherein the subject has a disorder associated with IL-1β such as acute or chronic inflammation or other anemia of chronic disease.

A series of experiments were performed to examine the effects of compounds of the present invention on EPO production following exposure of cells to the inflammatory cytokine IL-1β (i.e., in cells already exposed to IL-1β). In these experiments, IL-1β signaling would therefore be initiated prior to the addition of a prolyl hydroxylase inhibitor. Hep3B cells were treated with various concentrations (0, 0.4, 2, 10 ng/ml) of IL-1β for 2 hours, after which various concentrations of compound A or compound B were added to the cultured cells. Secreted EPO levels were determined as described above 3 days following compound addition.

Figure 4A:
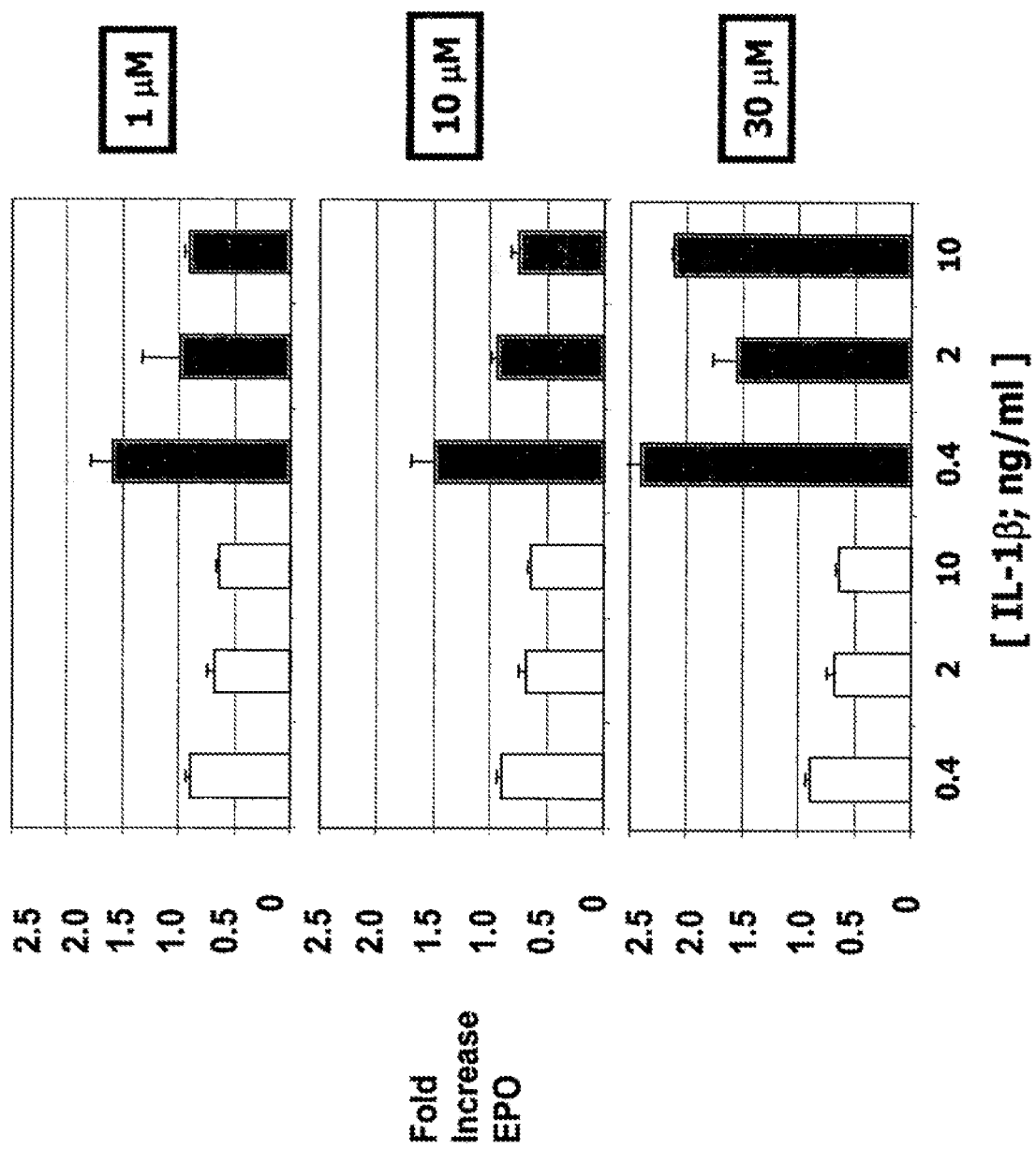
FIGS. 4A and 4B set forth data showing methods and compounds of the present invention overcome the suppressive effects of IL-1β on EPO production in cells pre-treated with IL-1β.
Figure 4B:
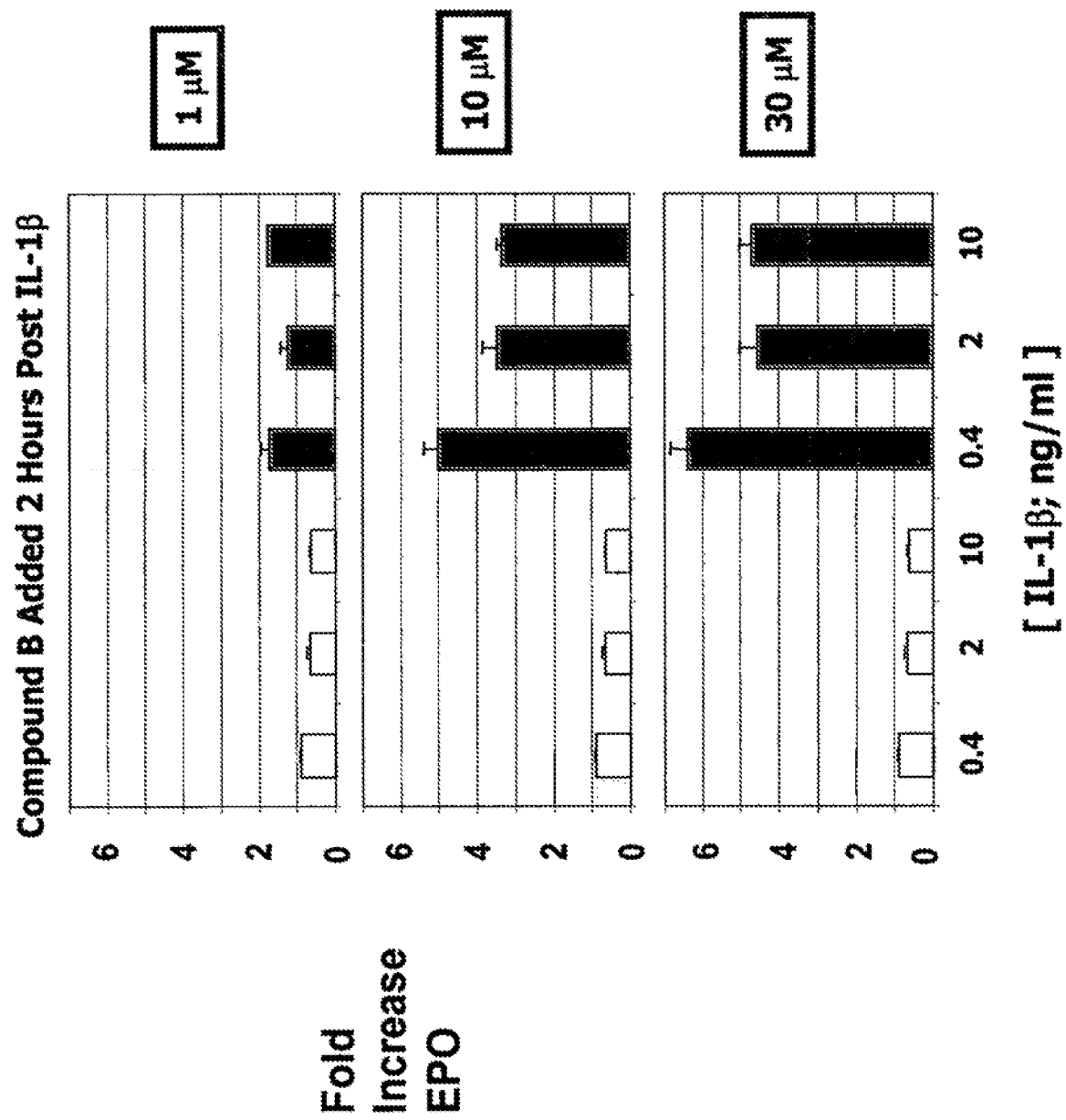

As shown in FIGS. 4A and 4B, compound A and compound B overcame the suppressive effects of IL-1β on EPO production following a 2-hour pre-treatment of Hep3B cells with IL-1β. This data indicated that compounds and methods of the present invention are useful for increasing EPO production in cells exposed to IL-1β. These results also suggested that treatment with compound of the present invention provides useful means to increase EPO production and treat anemia in a subject in which EPO production has been suppressed by IL-1β.

Addition of compounds of the present invention greatly reduced the inhibitory effects of IL1-β on EPO production. Therefore, compounds and methods of the present invention are useful for treating or preventing anemia associated with IL-1β, e.g., inflammatory disorders.

Example 3: Inhibition of TNF-α Induced VCAM-1 Expression

Endothelial cell adhesiveness for lymphocytes occurs, in part, by endothelial cell expression of vascular cell adhesion molecule (VCAM)-1. VCAM-1 expression in endothelial cells is induced by various inflammatory cytokines, such as TNF-α. To investigate the effect of HIF prolyl hydroxylase inhibition on TNF-α induced VCAM-1 expression, HUVEC (human umbilical vein endothelial cells) were stimulated with TNF-α in the absence or presence of various concentrations of compound B or compound C for 1 day. VCAM expression was then measured.

Figure 5:
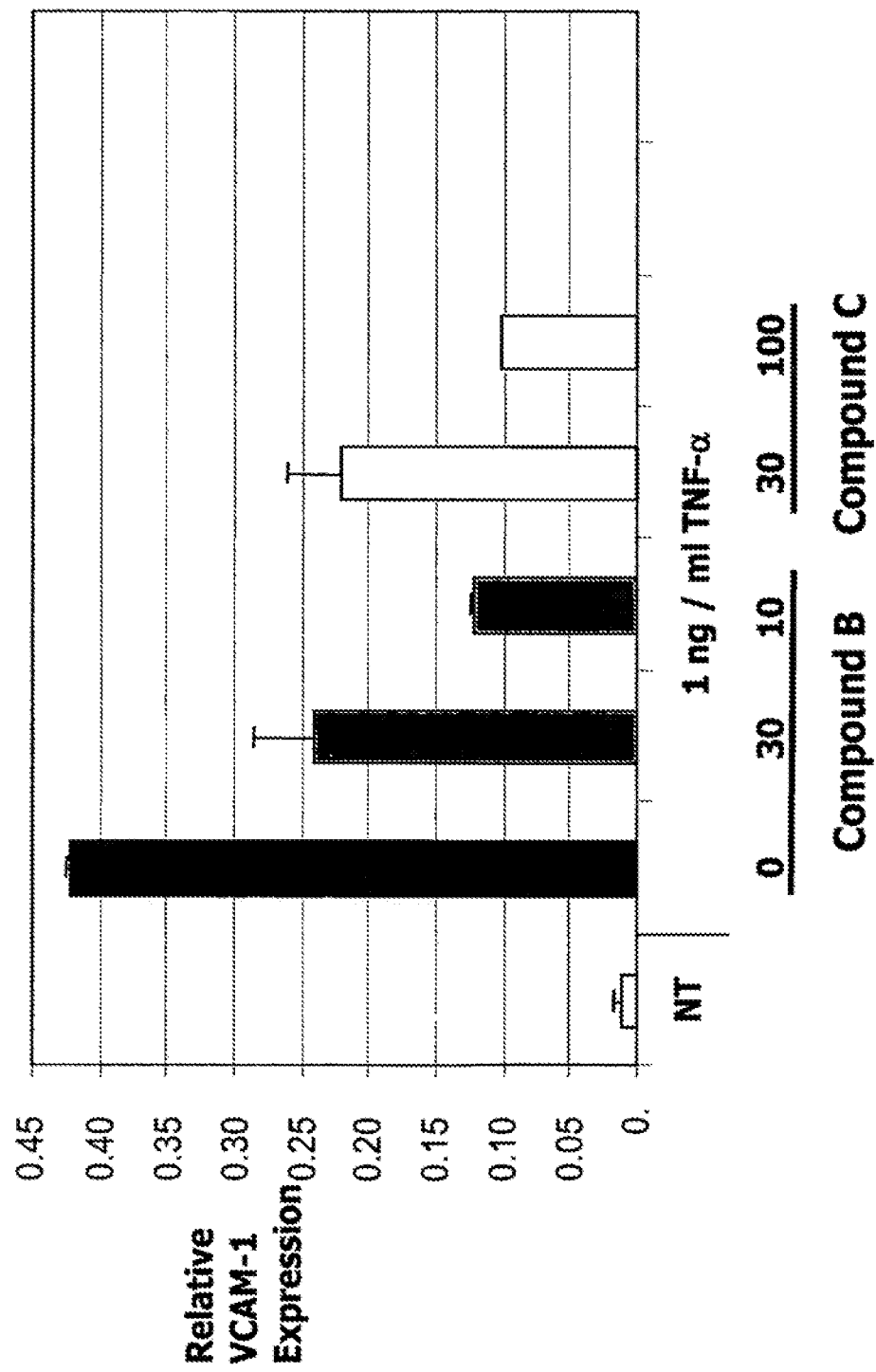
FIG. 5 sets forth data showing methods and compounds of the present invention reduce VCAM-1 expression associated with TNF-α.

As shown in FIG. 5, TNF-α (1 ng/ml) induced VCAM-1 expression in HUVEC cells. Addition of compound B or compound C to TNF-α stimulated cells, however, resulted in a does-dependent inhibition of TNF-α induced VCAM-1 expression. This data indicated that methods and compounds of the present invention are effective at reducing VCAM-1 expression associated with the inflammatory cytokine TNF-α. The results further suggested that compounds and methods of the present invention are useful for inhibiting VCAM-1 expression associated with various inflammatory and autoimmune diseases, such as, for example, anemia of chronic disease.

Example 4: Inhibition of IL-1β Induced VCAM-1 Expression

VCAM-1 expression in endothelial cells is also induced by the inflammatory cytokine IL-1β. To investigate the effect of HIF prolyl hydroxylase inhibition on IL-1β induced VCAM-1 expression, HUVEC (human umbilical vein endothelial cells) were stimulated with IL-1β in the absence or presence of various concentrations of compound B or compound C for 1 day. VCAM expression was then measured.

IL-1β (1 ng/ml) induced VCAM-1 expression in HUVEC cells. Addition of compound B or compound C to IL-1β stimulated cells, however, resulted in a does-dependent inhibition of IL-1β induced VCAM-1 expression. (Data not shown.) These results indicated that methods and compounds of the present invention are effective at reducing VCAM-1 expression associated with the inflammatory cytokine IL-1β. The results further suggested that compounds and methods of the present invention are useful for inhibiting VCAM-1 expression associated with various inflammatory and autoimmune diseases, such as, for example, anemia of chronic disease.

Example 5: Inhibition of TNF-α and IL-1β Induced VCAM-1 Expression on Endothelial Cells HUVEC were treated with vehicle control or various concentrations (0, 20, 40, 80 µM) of compound B or compound C for 24 hours. Cells were washed and then stimulated with either 1 ng/ml TNF-α or 1 ng/ml IL-1β for 4 hours. Cell surface VCAM-1 expression was then measured by cell-based ELISA.

Figure 25:
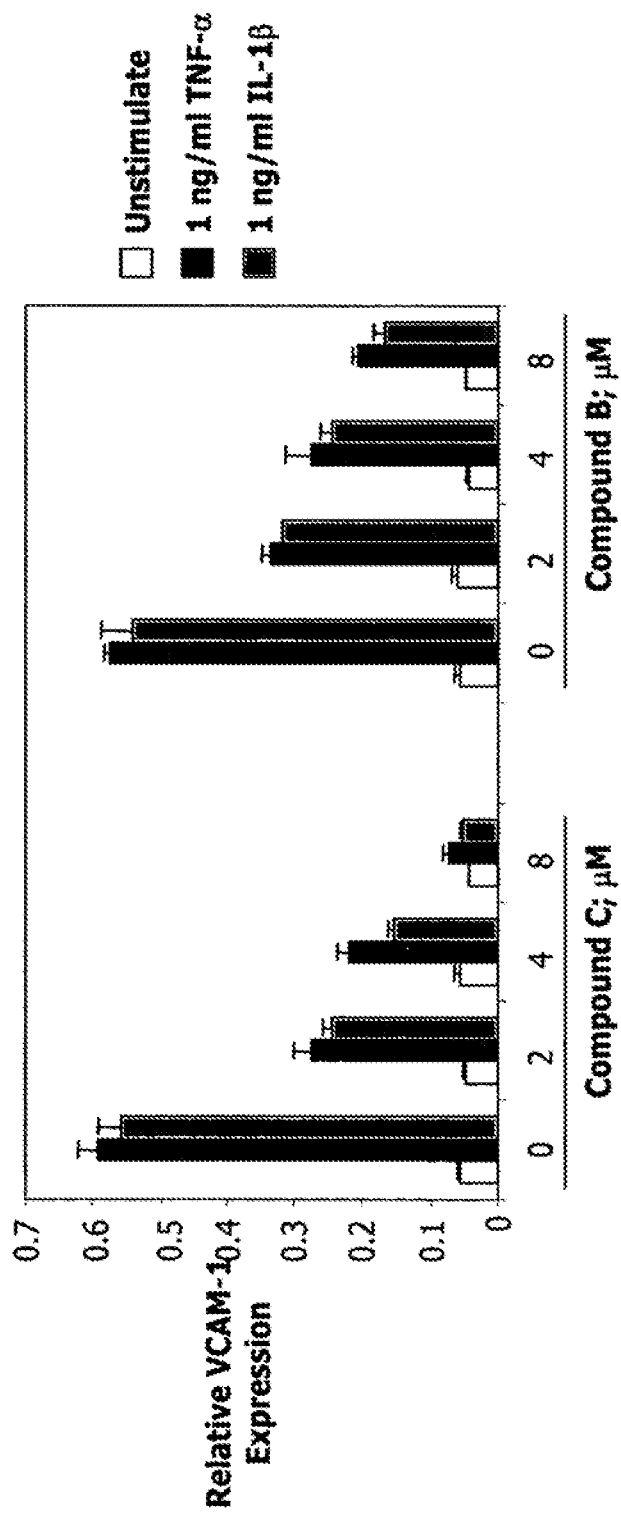
FIG. 25 sets forth data showing methods and compounds of the present invention reduced VCAM-1 expression associated with TNF-α and IL-1β.

As shown in FIG. 25, pretreatment with prolyl hydroxylase inhibitors decreased the induction of cell surface VCAM-1 expression induced by the inflammatory cytokines TNF-α and IL-1β. These results indicated that compounds and methods of the invention inhibited the inflammatory function of TNF-α and IL-1β and inhibited the expression of cell surface adhesion molecules important for mediating heterocellular leukocyte adhesion. Inhibition of leukocyte adhesion by treatment with the present compounds provides an effective means for decreasing inflammatory cascades, thereby reducing inflammation and reducing the inflammatory effect of limiting EPO production and suppressing erythropoiesis.

Example 6: Inhibition of TNF-α Induced E-Selectin Expression

Endothelial E-selectin belongs to the selectin family of cellular adhesion molecules mediating the initial attachment of leukocytes to vascular endothelial cells in inflammatory events. IL-1, TNF-α, and lipopolysaccharides each induce the expression of E-selectin. (See, e.g., Bevilacqua et al. (1987) Proc Natl Acad Sci USA 84:9238-9242 and Bevilacqua and van Furth (1993) J Leukoc Biol 54:363-378.) To investigate the effect of HIF prolyl hydroxylase inhibition on TNF-α induced E-selectin expression, HUVECs were stimulated with 1 ng/ml TNF-α in the absence or presence of various concentrations of compound B or compound C for 1 day. E-selectin and VCAM expression were then measured.

Figure 24A:
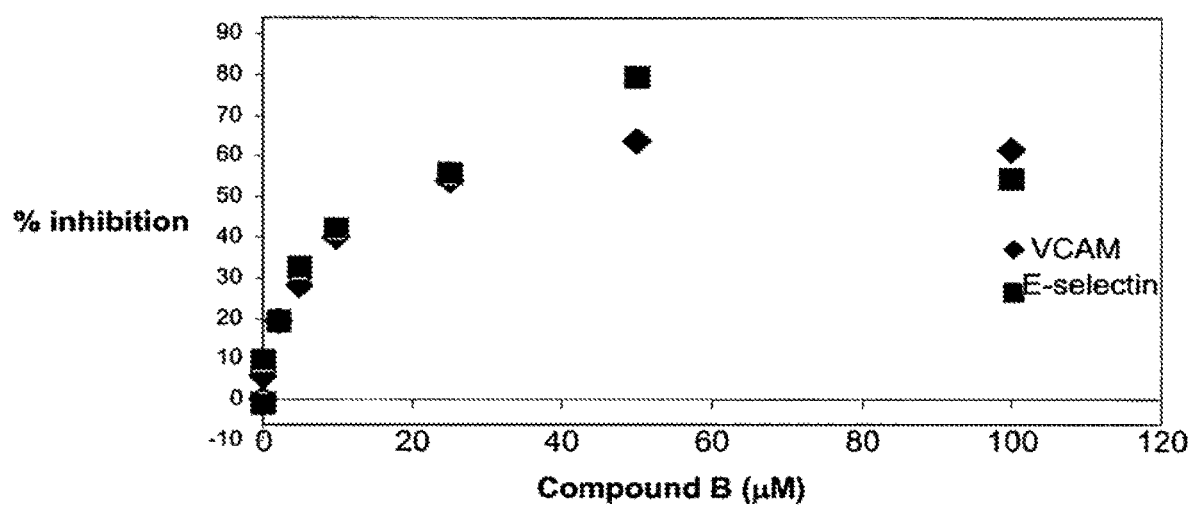
FIGS. 24A and 24B set forth data showing methods and compounds of the present invention reduced VCAM-1 and E-selectin expression associated with TNF-α.
Figure 24B:
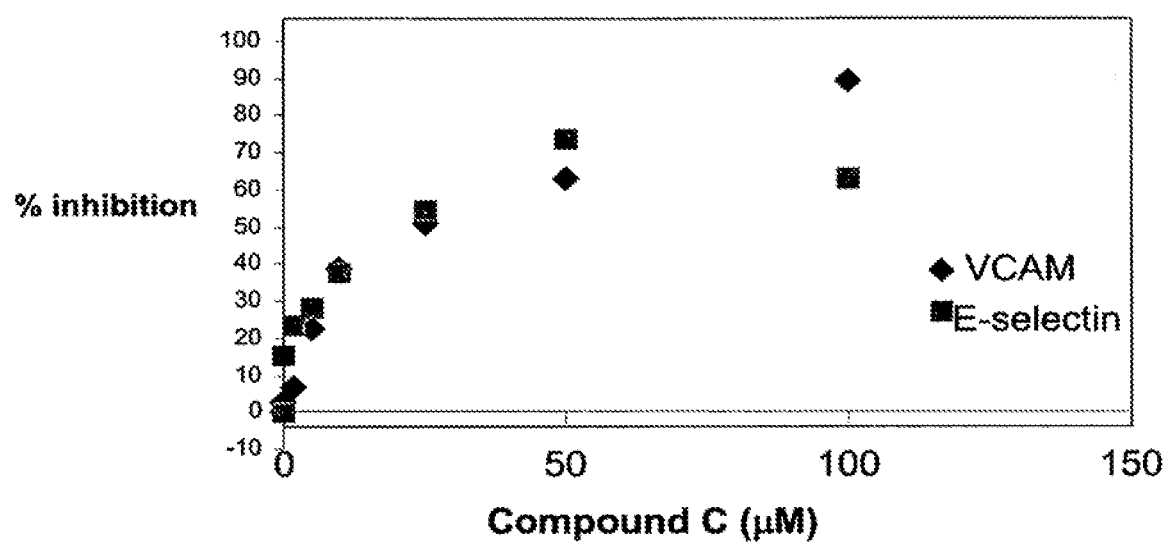

As shown in FIGS. 24A and 24B, compound B and compound C showed a dose-dependent inhibition of TNF-α induced VCAM and E-selectin expression in HUVECs. Data in FIGS. 24A and 24B is presented as percent inhibition of VCAM and E-selectin expression observed in response to various concentrations of compound B (FIG. 24A) or compound C (FIG. 24B). Greater than 60% inhibition of VCAM and E-selectin expression was observed in HUVEC treated with 50 µM compound B or compound C. This data indicated that methods and compounds of the present invention are effective at reducing VCAM and E-selectin expression in endothelial cells associated with the inflammatory cytokine TNF-α. The results further suggested that compounds and methods of the present invention are useful for inhibiting VCAM and E-selectin expression associated with various inflammatory and autoimmune disorders, such as, for example, anemia of chronic disease. Additionally, inhibition of endothelial cell expression of adhesion molecules, including VCAM and E-selectin, by methods and compounds of the present invention provides means for reducing early events in vascular inflammation.

Example 7: Inhibition of IL-1β Induced E-Selectin Expression

To investigate the effect of HIF prolyl hydroxylase inhibition on IL-1β induced E-selectin expression, HUVECs were stimulated with 1 ng/ml IL-1β in the absence or presence of various concentrations of compound B or compound C for 1 day. E-selectin expression was then measured.

Compound B and compound C showed a dose-dependent inhibition of IL-1β induced E-selectin expression in HUVECs. (Data not shown.) These results indicated that methods and compounds of the present invention are effective at reducing E-selectin expression in endothelial cells associated with the inflammatory cytokine IL-1β. The results further suggested that compounds and methods of the present invention are useful for inhibiting E selectin expression associated with various inflammatory and autoimmune disorders, such as, for example, anemia of chronic disease. Additionally, inhibition of endothelial cell expression of adhesion molecules, including VCAM and E-selectin, by methods and compounds of the present invention provides means for reducing early events in vascular inflammation.

Example 8: Inhibition of TNF-α, IL-1β, and IFN-γ Induced E-Selectin Expression

HUVEC were treated with vehicle control or various concentrations of compound B or compound C for 24 hours. Cells were washed and then stimulated with either 1 ng/ml TNF-α, 1 ng/ml IL-1β, or a combination of 1 ng/ml each of TNF-α, IL-1β, and IFN-γ for 4 hours. Cell surface expression of E-selectin was measured by cell-based ELISA.

Figure 26:
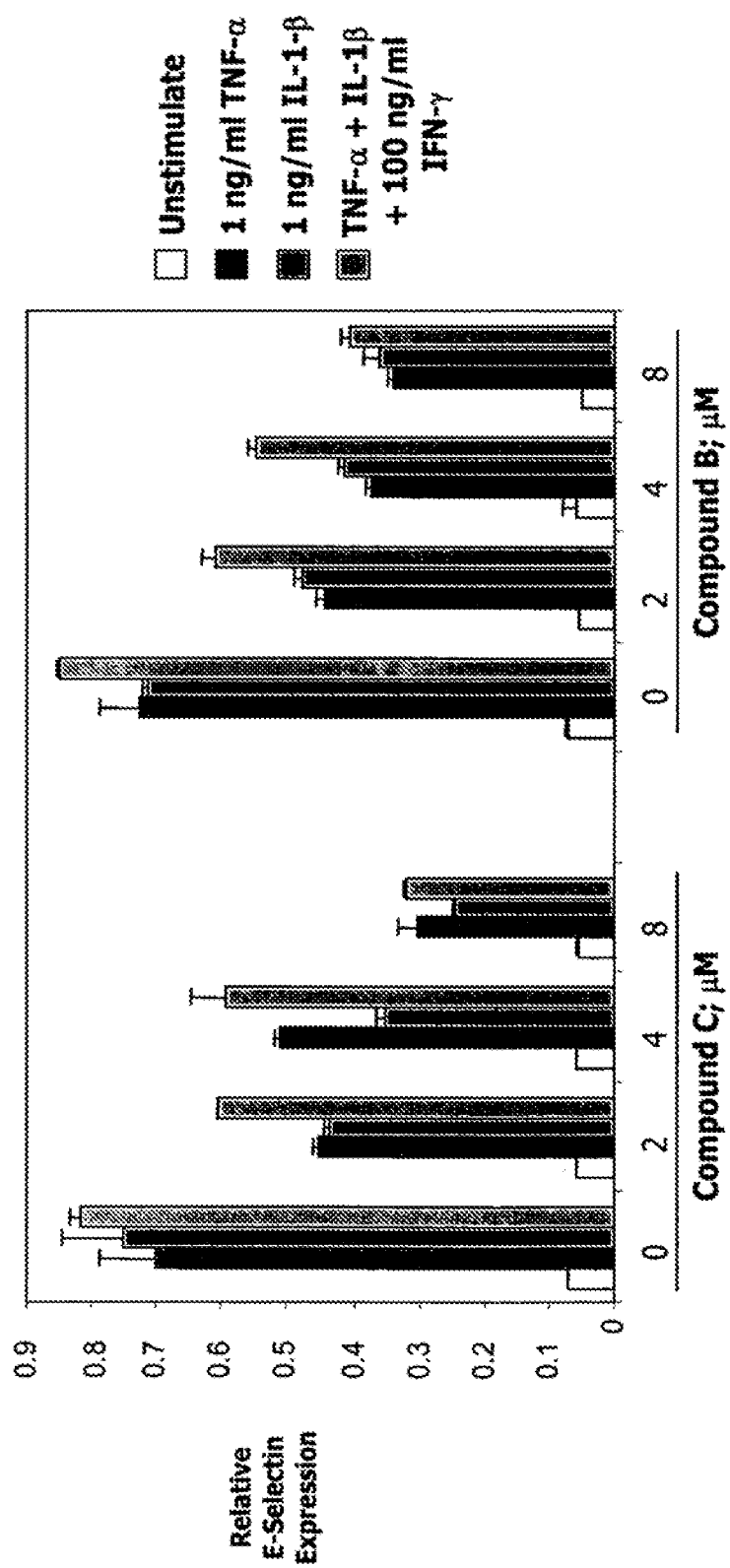
FIG. 26 sets forth data showing methods and compounds of the present invention reduced E-selectin expression associated with TNF-α, IL-1β, and IFN-γ.

As shown in FIG. 26, pretreatment of HUVEC with compound B or compound C inhibited the induction of cell surface E-selectin expression induced by the inflammatory cytokines TNF-α or IL-1β. In addition, pretreatment with either compound decreased E-selectin expression in the presence of three inflammatory cytokines known to increase E-selectin expression (TNF-α, IL-1β, and IFN-γ). These results indicated that the present compounds blocked the inflammatory function of TNF-α, IL-1β, and IFN-γ on endothelial cells, as exemplified by inhibition of the expression of cell surface adhesion molecules that mediate rolling of leukocytes on activated endothelium. Since leukocyte adhesion to activated endothelium via E-selectin is an early step in perpetuating inflammatory cascades, inhibition of leukocyte rolling by inhibiting E-selectin expression provides a means for decreasing inflammatory cascades that further limit EPO production and suppress erythropoiesis.

Example 9: Synergistic Increase in EPO Production

Figure 27A:
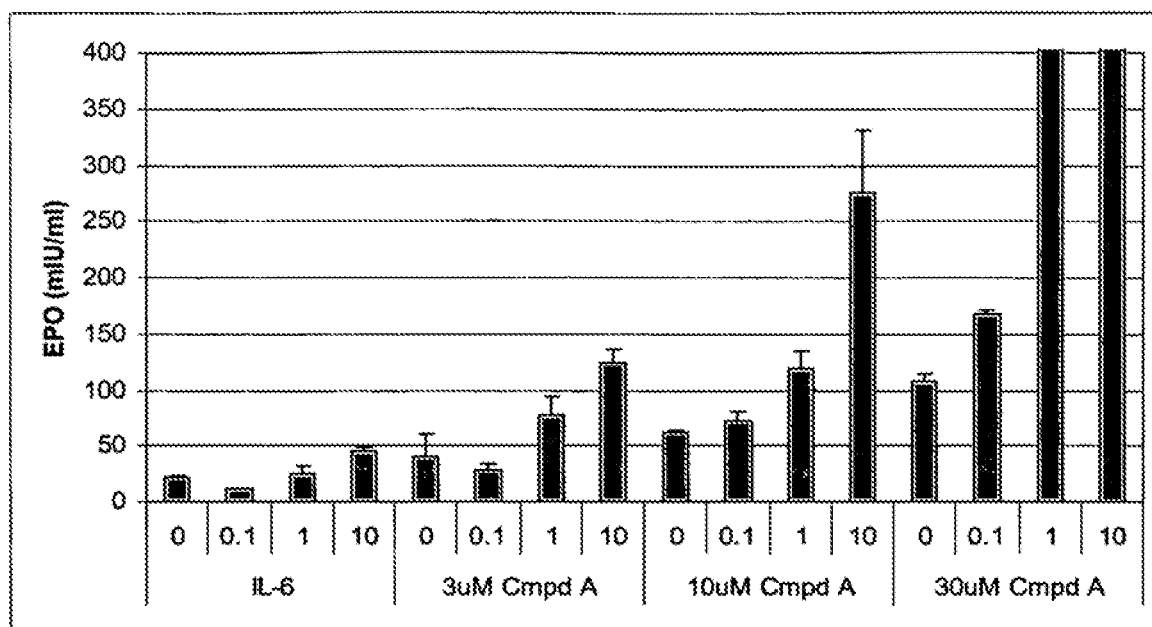
FIGS. 27A and 27B set forth data showing methods and compounds of the present invention and IL-6 synergistically increased EPO levels in hepatocytes.
Figure 27B:
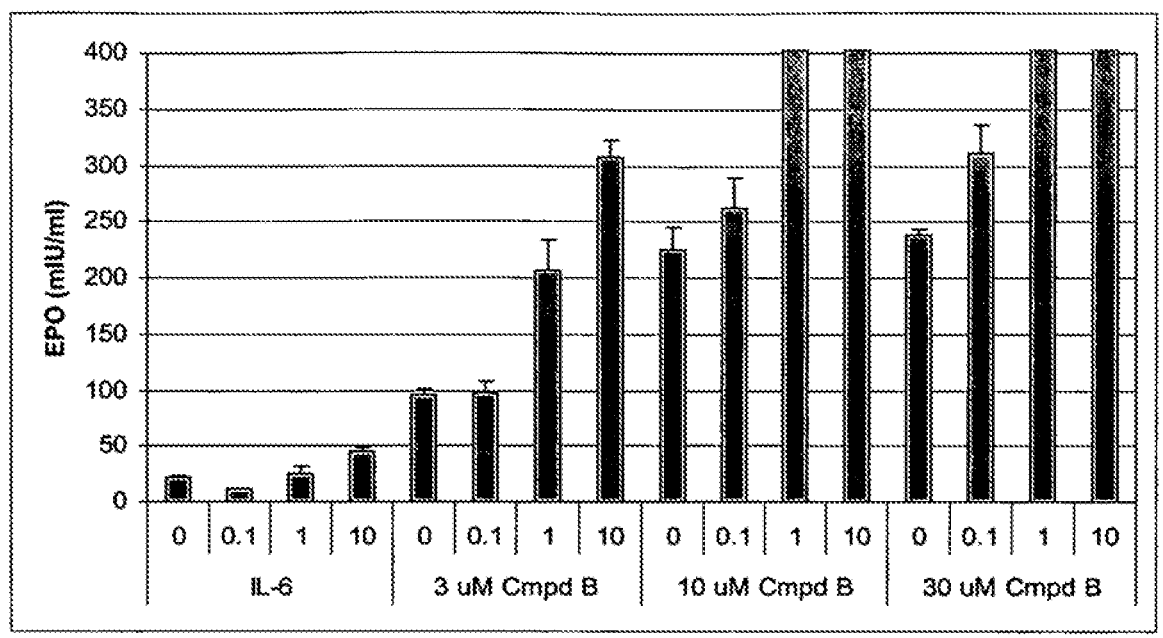

Hep3B cells were treated with various concentrations (0, 0.1, 1, 10 ng/ml) of IL-6 in the absence of presence of various concentrations (3 µM, 10 µM, 30 µM) of compound A or compound B for 1 or 3 days. Secreted EPO levels were determined using a commercially available ELISA kit (R&D Systems, catalog no. DEP00). In the absence of compound, treatment of Hep3B cells with IL-6 had a minimal effect on EPO production. As shown in FIGS. 27A and 27B, Hep3B cells treated with IL-6 increased EPO expression slightly above that in non-treated cells. Specifically, EPO levels in control cells was approximately 20 mIU/ml, while that in cells treated with 10 ng/ml IL-6 was approximately 50 mIU/ml.

Hep3B cells treated with compound A or compound B without IL-6 showed increased EPO levels in a dose-dependent manner Hep3B cells treated with compound A or compound B in the presence of IL-6, however, showed a significant increase in EPO levels. (See FIGS. 27A and 27B.) The effect of compound treatment on EPO production in the presence of IL-6 was synergistic. For example, Hep3B cells treated with 10 ng/ml IL-6 showed approximately 50 mIU/ml EPO levels. Treatment of Hep3B cells with 10 mM compound A or compound B in the absence of IL-6 resulted in approximately 60 mIU/ml EPO and 220 mIU/ml, respectively. In the presence of 10 ng/ml IL-6, compound A and compound B addition increased EPO levels to approximately 270 mIU/ml and to greater than 400 mIU/ml, respectively. Therefore, compounds of the present invention acted synergistically with IL-6 at inducing EPO expression in hepatocytes.

Example 10: Overcoming Cytokine-Induced Suppression of EPO Receptor Signaling

The cell line TF-1 (human erythroleukemia; ATCC cat #CRL-2003) is stimulated to proliferate in response to EPO addition. In the presence of various pro-inflammatory cytokines, the EPO-mediated increase in TF-1 cell proliferation is attenuated. To determine the effects of prolyl hydroxylase inhibition on TF-1 cell proliferation, TF-1 cells are treated with the various concentrations of the pro-inflammatory cytokines TNF-α, or IFN-γ in the absence or presence of prolyl hydroxylase inhibitors, and EPO-mediated cell proliferation is measured as follows. Triplicate wells of cells cultured in 96-well microtiter plates are incubated with serum-free medium in the absence or presence of EPO for 24 hours. During the final 4 hours of culture, 1 µCi of tritiated thymidine ($^3$H-TdR; Amersham) is added to each well. Cell responsiveness to EPO receptor signaling is determined by measuring cell proliferation. Cell proliferation is measured by quantitating the amount of $^3$H-TdR incorporated into cells, first by lysing the cells with water and then capturing the DNA on nylon filters in a cell harvester.

Alternatively, single cell suspensions of splenic cells obtained from phenylhydrazine-treated animals, which lead to prevalence of EPO responsive progenitors in spleen, are used as the source of EPO responsive cells. EPO-mediated proliferation is then assessed ex vivo as described above.

TF-1 cells treated with EPO results in an increase in cell proliferation, as determined by an increase in tritiated thymidine incorporation. Addition of the pro-inflammatory cytokines TNF-α, or IFN-γ to EPO-treated TF-1 cells results in decreased responsiveness to EPO, leading to decreased cell proliferation. The effect of addition of the present compounds on the inhibitory effects of pro-inflammatory cytokines on EPO-mediated cell proliferation in TF-1 cells is determined. Increased cell proliferation, as measured by increased tritiated thymidine incorporation, in TF-1 cells treated with EPO and pro-inflammatory cytokines indicates that compounds and methods of the present invention overcome the suppressive effects of pro-inflammatory cytokines on EPO-mediated increase in cell proliferation.

Example 11: Increasing Transferrin Receptor Expression

The effect of compounds of the invention on transferrin receptor expression was examined as follows. Various cells (Hep3B, HepG2, HK-2) were incubated with compound A or compound B for 1 day. The cells were then analyzed for transferrin receptor expression by FACS analysis using CD71-PE antibody (Ancell, catalog no. 223-050). The results are shown below in Table 1.

TABLE 1

| Cell Type | Treatment  | Mean FL |
|-----------|------------|---------|
| Hep3B     | DMSO       | 40.21   |
|           | Compound A | 40.89   |
|           | Compound B | 42.43   |
| HepG2     | DMSO       | 49.59   |
|           | Compound A | 56.52   |
|           | Compound B | 53.53   |
| HK-2      | DMSO       | 10.80   |
|           | Compound A | 12.20   |
|           | Compound B | 18.92   |

As shown above in Table 1, addition of various compounds of the present invention to cells increased expression of transferrin receptor. Inhibition of HIF prolyl hydroxylation using prolyl hydroxylase inhibitors of the present invention increased transferrin receptor expression in cells. Increased transferrin receptor expression using prolyl hydroxylase inhibitors of the present invention was observed in liver cells (e.g., Hep3B, HepG2), kidney cells (e.g., HK-2), and lymphocytes (e.g., THP-1). Therefore, methods and compounds of the present invention are useful for increasing transferrin receptor expression in various cell types. In addition, increased transferrin receptor expression would result in increased transferrin receptor-mediated endocytosis of ferric transferrin, thereby increasing iron transport, utilization, storage, and metabolism. Therefore, methods and compounds of the present invention are useful for enhancing erythropoiesis by increasing iron transport, utilization, storage, and metabolism.

Example 12: Increasing Transferrin Receptor Expression and Iron Uptake In Vitro

The effect of compounds on iron uptake in cells is determined as follows. Primary monocytes and macrophage, and monocyte and macrophage cell lines (e.g., THP-1), are treated for one, two, or three days with various concentrations of prolyl hydroxylase inhibitors. Cells are then examined for the presence of cell surface transferrin receptor using fluorescent immunostaining and flow cytometry. Results showing that addition of prolyl hydroxylase inhibitors increase cell surface transferrin receptor expression indicates effectiveness of prolyl hydroxylase inhibition at increasing transferrin binding and, therefore, iron binding, to cells. A change in iron uptake by cells treated with prolyl hydroxylase inhibitors is determined as follows. Cells are treated with compound in the presence of $^{59}$Fe. Increased iron uptake by cells treated with prolyl hydroxylase inhibitors is determined by measuring cell-associated $^{59}$Fe. An increase in cell-associated $^{59}$Fe indicates increased iron uptake in cells.

Example 13: Increasing Iron-Regulatory Protein-2 Levels and Activity

The regulation of iron uptake, storage, and utilization occur, in part, through the expression and activity of key proteins involved in iron metabolism, including trans-acting proteins known as iron-regulatory proteins (IRPs). IRP-1 and IRP-2 control mRNA stability and translation by binding to specific iron-responsive elements in various mRNAs of proteins involved in iron metabolism, thereby affecting virtually all aspects of iron metabolism. Iron deficiency increases IRP activity, resulting in increased transferrin receptor expression and reduced ferritin expression. Likewise, in the presence of iron, IRP activity decreases, leading to decreased transferrin receptor expression and increased ferritin expression.

To examine the effect of the present compounds on various aspects of iron metabolism, the following experiment is performed. Mouse Hepa-1 cells are treated with prolyl hydroxylase inhibitors for up to 48 hours. The cells are then harvested and cell lysates analyzed for IRP-2 expression by immunoblotting using an antibody specific for IRP-2 (Alpha Diagnostic International, Inc., San Antonio Tex.). Results showing increased levels of cytoplasmic IRP-2 following addition of compound demonstrates that methods and compounds of the present invention are useful for increasing IRP levels and therefore iron metabolism.

The effect of compounds of the invention on IRP-2 activity, as measured by changes in ferritin and transferrin expression, is determined as follows. Mouse RAW 264.1 macrophage cell line is treated with prolyl hydroxylase inhibitors for up to 48 hours. Cells are then harvested and analyzed for ferritin and transferrin protein expression by immunoblotting (ADI, catalogue #IRP21-S). Decreased levels of ferritin expression and increased levels of transferrin expression following prolyl hydroxylase inhibition indicates that methods and compounds of the present invention are useful for stabilizing and increasing the activity of IRP-2. Increased expression of IRP-2 decreases expression of ferritin, which is responsible for long-term storage of iron, and increases expression of transferrin and transferrin receptor, facilitating iron uptake, transport, and utilization, thus enhancing erythropoiesis. By increasing expression and activity of IRP-2, methods and compounds of the present invention are useful for decreasing expression of ferritin and associated long-term storage of iron, and increasing expression of transferrin and transferrin receptor. Therefore, methods and compounds of the present invention are useful for increasing iron uptake, transport, and utilization, and are thus useful for enhancing erythropoiesis.

Example 14: Enhancing Iron Utilization

Rats are administered either vehicle control or HIF prolyl hydroxylase inhibitors prior to intravenous injection with $^{59}$Fe-radiolabeled ferrous citrate (Amersham). Serial samples of blood are drawn from the tail vein and total free plasma and erythrocyte-associated radioactivity is measured in a scintillation counter to detect iron transport and incorporation into erythrocyte heme and hemoglobin synthesis. Increase in erythrocyte-associated $^{59}$Fe indicates that the present compounds are useful for enhancing iron utilization necessary for heme synthesis, hemoglobin production, and erythropoiesis.

Example 15: Enhanced Expression of Erythropoiesis Genes In Vitro

Hep3B cells (ATCC No. HB-8064) were grown in DMEM containing 8% fetal bovine serum. Hep3B cells were seeded into 6-well culture dishes at ~500,000 cells per well. After 8 hours, the media was changed to DMEM containing 0.5% fetal bovine serum and the cells were incubated for an additional 16 hours. Compound B or compound D was added to the cells (25 µM final concentration) and the cells were incubated for various times. Control cells (no compound treatment, addition of DMSO alone) were harvested at 0, 6 and 48 hours. Harvested cells were assessed for cell viability (GUAVA), or added to RNA extraction buffer (RNeasy, Qiagen) and stored at −20° C. for subsequent RNA purification. Replicate microarrays were generated using RNA isolated from replicate experiments conducted on different days. Total RNA was isolated from cells using the RNeasy kit (Qiagen).

RNA was precipitated in 0.3 M sodium acetate (pH 5.2), 50 ng/ml glycogen, and 2.5 volumes of ethanol for one hour at −20° C. Samples were centrifuged and pellets were washed with cold 80% ethanol, dried, and resuspend in water. Double stranded cDNA was synthesized using a T7-(dT)24 first strand primer (Affymetrix, Inc., Santa Clara Calif.) and the SUPERSCRIPT CHOICE system (Invitrogen) according to the manufacturer's instructions. The final cDNA was extracted with an equal volume of 25:24:1 phenol:chloroform:isoamyl alcohol using a PHASE LOCK GEL insert (Brinkman, Inc., Westbury N.Y.). The aqueous phase was collected and cDNA was precipitated using 0.5 volumes of 7.5 M ammonium acetate and 2.5 volumes of ethanol. Alternatively, cDNA was purified using the GENECHIP sample cleanup module (Affymetrix) according to the manufacturer's instructions.

Biotin-labeled cRNA was synthesized from the cDNA in an in vitro translation (IVT) reaction using a BIOARRAY HighYield RNA transcript labeling kit (Enzo Diagnostics, Inc., Farmingdale N.Y.) according to the manufacturer's instructions. Final labeled product was purified and fragmented using the GENECHIP sample cleanup module (Affymetrix) according to the manufacturer's instructions.

Hybridization cocktail was prepared by bringing 5 μg probe to 100 μl in 1× hybridization buffer (100 mM MES, 1 M [$Na^+$], 20 mM EDTA, 0.01% Tween 20), 100 μg/ml herring sperm DNA, 500 μg/ml acetylated BSA, 0.03 nM control oligo B2 (Affymetrix), and 1×GENECHIP eukaryotic hybridization control (Affymetrix). The cocktail was sequentially incubated at 99° C. for 5 minutes and 45° C. for 5 minutes, and then centrifuged for 5 minutes. The Human Genome U133A array (Affymetrix) was brought to room temperature and then prehybridized with 1× hybridization buffer at 45° C. for 10 minutes with rotation. The buffer was then replaced with 80 μl hybridization cocktail and the array was hybridized for 16 hours at 45° C. at 60 rpm with counter balance. Following hybridization, arrays were washed once with 6×SSPE, 0.1% Tween 20, and then washed and stained using R-phycoerythrin-conjugated streptavidin (Molecular Probes, Eugene Oreg.), goat anti-streptavidin antibody (Vector Laboratories, Burlingame Calif.), and a GENECHIP Fluidics Station 400 instrument (Affymetrix) according to the manufacturer's micro_1v1 protocol (Affymetrix). Arrays were analyzed using a GENEARRAY scanner (Affymetrix) and Microarray Suite software (Affymetrix).

The Human Genome U133A array (Affymetrix) represents all sequences in the Human Unigene database build 133 (National Center for Biotechnology Information, Bethesda Md.), including approximately 14,500 well-characterized human genes.

RNA quality was monitored by capillary electrophoresis (Agilent Bioanalyzer). Hybridization cocktails were prepared as described (Affymetrix), and hybridized to Affymetrix human U133A arrays containing 22,283 probe sets. Array performance was analyzed with Affymetrix MicroArray Suite (MAS) software and individual probe sets were assigned "present", "marginal, and "absent" calls according to software defaults. Statistical analyses and filtered probe set lists were prepared using GeneSpring software (Silicon Genetics). Cutoffs for "expressed" probe sets used a combination of Affymetrix "P" calls and absolute expression values derived from Genespring's intrinsic data error model. Data was normalized to averaged control samples.

As shown in Table 2 below, expression of genes (fold-increase in mRNA levels above control) encoding erythropoietic proteins was increased in Hep3B cells treated with compound of the present invention. (Two ceruloplasmin data points for each condition are presented below in Table 2.) Specifically, ceruloplasmin and transferrin receptor 2 gene expression were increased in Hep3B cells treated with various compounds of the present invention.

TABLE 2

| Compound | Time | Ceruloplasmin (CP) | Transferrin Receptor (TFR2) |
|---|---|---|---|
| D | 6 hr | 2.06/2.387 | Not Determined |
| B | 1 hr | 1.142/0.946 | 0.575 |
| B | 3 hr | 1.123/0.955 | 0.558 |
| B | 6 hr | 1.555/1.103 | 0.822 |
| B | 12 hr | 2.366/2.507 | 1.253 |
| B | 24 hr | 5.136/4.909 | 2.522 |
| B | 48 hr | 5.82/4.678 | 4.169 |

Example 16: Animal Dosing

Animals used in the following examples include Swiss Webster male mice (30-32 g), Sprague Dawley male rats (200-350 g) and Lewis female rates obtained from Simonsen, Inc. (Gilroy Calif.), Charles River (Hollister, Calif.), or Harlan Animals were maintained using standard procedures, and food and water were available to the animals ad libitum. During treatment, animals were monitored for changes in body weight and signs of overt toxicity and mortality.

Compounds were generally administered orally by gavage or IV administration. Animals treated by oral gavage received a 4-10 ml/kg volume of either 0.5% carboxymethyl cellulose (CMC; Sigma-Aldrich, St. Louis Mo.) with or without 0.1% Polysorbate 80 (0 mg/kg/day) or varying doses of a compound of the present invention (e.g., a HIF prolyl hydroxylase inhibitor) in 0.5% CMC, with or without 0.1% Polysorbate 80, using various dosing regimens. Blood samples were collected at appropriate intervals during treatment from, e.g., tail vein (rats), or abdominal vein or cardiocentesis (mice or rats). Generally, animals were anesthetized with isoflurane and blood samples were collected into MICROTAINER serum separator tubes (Becton-Dickinson, Franklin Lakes N.J.). For measurement of serum components, the tubes were incubated at room temperature for 30 minutes, and then centrifuged at 8,000 rpm at 4° C. for 10 minutes. The serum fraction was then processed and analyzed for the presence of specific components, e.g., serum iron (assay performed by Quality Clinical Labs, Mountain View, Calif.). For determination of hematocrit, blood samples were collected into MICROTAINER EDTA-2K tubes (Becton-Dickinson); EDTA-blood was then drawn into 75 mm×1.1-1.2 mm I.D. capillary tubes (Chase Scientific Glass, Inc., Rockwood Tenn.) to approximately ¾ length, one end of the tube was sealed with CRITOSEAL sealant (Sherwood Medical Company), and the tubes were centrifuged in a J-503M MICROHEMATOCRIT centrifuge (Jorgensen Laboratories, Inc., Loveland Colo.) at 12,000 rpm for 5 minutes. Hematocrit was read against a reader card. When indicated, complete blood count (CBC) analysis, including blood hemoglobin level, reticulocyte number, and hematocrit, was performed by Quality Clinical Labs (Mountain View, Calif.).

At the end of each study, animals were euthanized, e.g. by exsanguinations under general anesthesia or by $CO_2$ asphyxiation, and organ and tissue samples were collected. Tissues were either fixed in neutral buffered formalin or stored frozen at −70° C. Tissues for genomic analysis were placed in RNAlater.

Example 17: Increased Expression of Genes Encoding Iron-Processing Proteins In Vivo Swiss Webster male mice were treated as described above with a single dose of 0.5% CMC (Sigma-Aldrich) (0 mg/kg) or 100 mg/kg compound A. At 4, 8, 16, 24, 48, or 72 hours post-administration, animals were anesthetized, sacrificed, and tissue samples of kidney, liver, brain, lung, and heart were isolated and stored in RNALATER solution (Ambion) at −80° C. Alternatively, animals were treated to 4 consecutive daily doses of 0.5% CMC (0 mg/kg/day), 7.5 mg/ml compound A in 0.5% CMC (30 mg/kg/day), or 25 mg/ml compound A in 0.5% CMC (100 mg/kg/day). Four hours after administration of the final dose, animals were anesthetized, sacrificed, and approximately 150 mg of liver and each kidney were isolated and stored in RNALATER solution (Ambion) at −20° C.

RNA isolation was carried out using the following protocol. A section of each organ was diced, 875 µl of RLT buffer (RNEASY kit; Qiagen Inc., Valencia Calif.) was added, and the pieces were homogenized for about 20 seconds using a rotor-stator POLYTRON homogenizer (Kinematica, Inc., Cincinnati Ohio). The homogenate was micro-centrifuged for 3 minutes to pellet insoluble material, the supernatant was transferred to a new tube and RNA was isolated using an RNEASY kit (Qiagen) according to the manufacturer's instructions. The RNA was eluted into 80 µL of water and quantitated with RIBOGREEN reagent (Molecular Probes, Eugene Oreg.). The absorbance at 260 and 280 nm was measured to determine RNA purity and concentration.

Alternatively, tissue samples were diced and homogenized in TRIZOL reagent (Invitrogen Life Technologies, Carlsbad Calif.) using a rotor-stator POLYTRON homogenizer (Kinematica). Homogenates were brought to room temperature, 0.2 volumes chloroform was added, and samples were mixed vigorously. Mixtures were incubated at room temperature for several minutes and then were centrifuged at 12,000 g for 15 min at 4° C. The aqueous phase was collected and 0.5 volumes of isopropanol were added. Samples were mixed, incubated at room temperature for 10 minutes, and centrifuged for 10 min at 12,000 g at 4° C. The supernatant was removed and the pellet was washed with 75% EtOH and centrifuged at 7,500 g for 5 min at 4° C. The absorbance at 260 and 280 nm was measured to determine RNA purity and concentration.

RNA was precipitated in 0.3 M sodium acetate (pH 5.2), 50 ng/ml glycogen, and 2.5 volumes of ethanol for one hour at −20° C. Samples were centrifuged and pellets were washed with cold 80% ethanol, dried, and resuspend in water. Double stranded cDNA was synthesized using a T7-(dT)24 first strand primer (Affymetrix, Inc., Santa Clara Calif.) and the SUPERSCRIPT CHOICE system (Invitrogen) according to the manufacturer's instructions. The final cDNA was extracted with an equal volume of 25:24:1 phenol:chloroform:isoamyl alcohol using a PHASE LOCK GEL insert (Brinkman, Inc., Westbury N.Y.). The aqueous phase was collected and cDNA was precipitated using 0.5 volumes of 7.5 M ammonium acetate and 2.5 volumes of ethanol. Alternatively, cDNA was purified using the GENECHIP sample cleanup module (Affymetrix) according to the manufacturer's instructions.

Biotin-labeled cRNA was synthesized from the cDNA in an in vitro translation (IVT) reaction using a BIOARRAY HighYield RNA transcript labeling kit (Enzo Diagnostics, Inc., Farmingdale N.Y.) according to the manufacturer's instructions. Final labeled product was purified and fragmented using the GENECHIP sample cleanup module (Affymetrix) according to the manufacturer's instructions.

Hybridization cocktail was prepared by bringing 5 µg probe to 100 µl in 1× hybridization buffer (100 mM MES, 1 M [Na$^+$], 20 mM EDTA, 0.01% Tween 20), 100 µg/ml herring sperm DNA, 500 µg/ml acetylated BSA, 0.03 nM control oligo B2 (Affymetrix), and 1×GENECHIP eukaryotic hybridization control (Affymetrix). The cocktail was sequentially incubated at 99° C. for 5 minutes and 45° C. for 5 minutes, and then centrifuged for 5 minutes. The Murine genome MOE430Aplus2 array (Affymetrix) was brought to room temperature and then prehybridized with 1× hybridization buffer at 45° C. for 10 minutes with rotation. The buffer was then replaced with 80 µl hybridization cocktail and the array was hybridized for 16 hours at 45° C. at 60 rpm with counter balance. Following hybridization, arrays were washed once with 6×SSPE, 0.1% Tween 20, and then washed and stained using R-phycoerythrin-conjugated streptavidin (Molecular Probes, Eugene Oreg.), goat anti-streptavidin antibody (Vector Laboratories, Burlingame Calif.), and a GENECHIP Fluidics Station 400 instrument (Affymetrix) according to the manufacturer's EukGE-WS2v4 protocol (Affymetrix). Arrays were analyzed using a GENEARRAY scanner (Affymetrix) and Microarray Suite software (Affymetrix).

The Murine Genome MOE430Aplus2 array (Affymetrix) represents all sequences in the Murine UniGene database build 107 (National Center for Biotechnology Information, Bethesda Md.), including approximately 14,000 well-characterized mouse genes.

Table 3 below shows ceruloplasmin mRNA expression in mouse kidney following administration of compound A. Data was normalized to the average value of that observed in control non-treated animals.

TABLE 3

| Condition | Ceruloplasmin (relative mRNA levels) |
|---|---|
| Untreated | 0.81 |
| CMC control | 1.26 |
| Compound A - 4 hours | 1.16 |
| Compound A - 8 hours | 1.39 |
| Compound A - 16 hours | 1.22 |
| Compound A - 24 hours | 2.45 |
| Compound A - 48 hours | 1.44 |
| Compound A - 72 hours | 2.10 |

Data shown in Table 3 above demonstrated that methods and compounds of the present invention are useful for increasing ceruloplasmin gene expression. Ceruloplasmin, also known as a ferroxidase-1, converts reduced iron released from storage sites (such as ferritin) to the oxidized form. Oxidized iron is able to bind to its plasma transport protein, transferrin. Ceruloplasmin deficiencies are associated with accumulation of iron in liver and other tissues. Evidence indicates that ceruloplasmin promotes efflux of iron from the liver and promotes influx of iron into iron-deficient cells. (See, e.g., Tran et al. (2002) J Nutr 132:351-356.)

Table 4 below shows hepcidin mRNA expression in mouse liver following administration of compound A. Data was normalized to that observed in control non-treated animals

TABLE 4

| Condition/ Animal Study | Time | Hepcidin (relative mRNA levels) |
|---|---|---|
| Control | — | 1.0 |
| I - multi high dose | — | 0.275 |
| II - multi high dose | — | 0.703 |
| II - multi low dose | — | 0.129 |
| III | 4 hour | 0.672 |
| III | 8 hour | 0.305 |
| III | 16 hour | 0.119 |

As shown above in Table 4, administration of compound A resulted in reduced expression of hepcidin mRNA in mouse liver. Decreased hepcidin expression is associated with increased iron release from reticuloendothelial cells and increased intestinal iron absorption. Therefore, methods and compounds of the present invention are useful for decreasing hepcidin expression and increasing intestinal iron absorption.

Figure 6A:
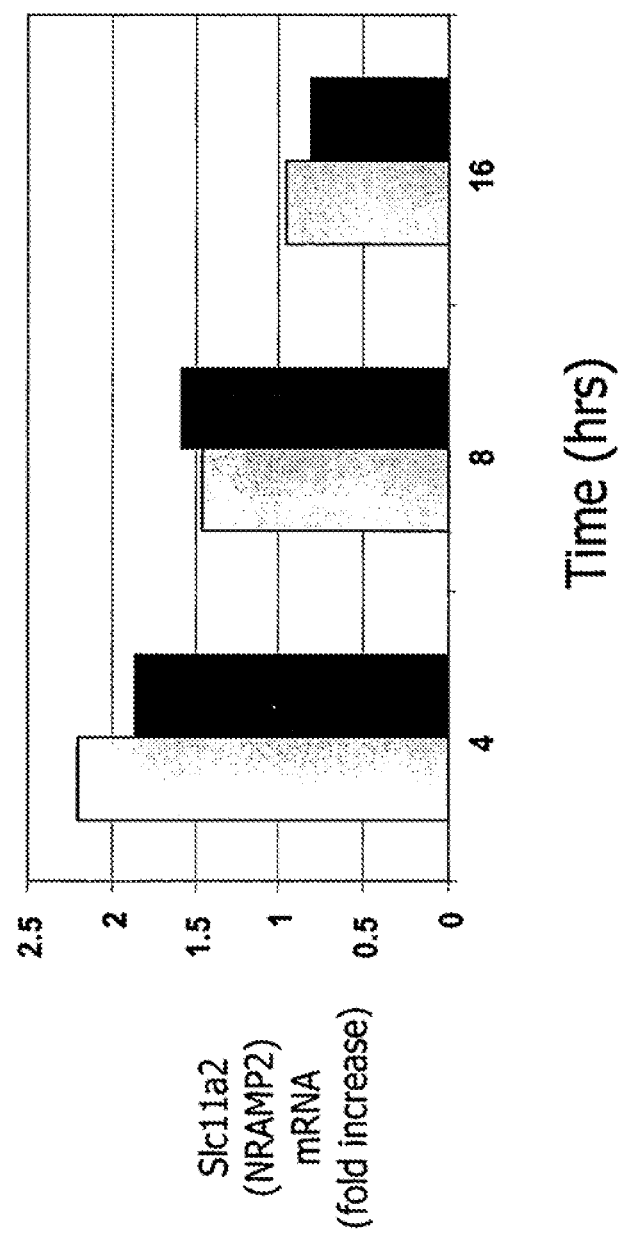
FIGS. 6A, 6B, and 6C set forth data showing increased expression of transferrin receptor and iron transporter (FIG. 6A), intestinal iron transport protein (FIG. 6B), and 5-aminolevulinate synthase (FIG. 6C) following treatment of mice with compounds of the present invention.

FIG. 6A shows relative expression levels of the transferrin receptor (gray bars) in kidney, and the gut duodenal iron transporter NRAMP2 (natural-resistance-associated macrophage protein 2) (also known as Slc11a2 (solute carrier family 11, proton-coupled divalent metal ion transporter, member 2), alternatively called DCT1 (divalent cation transporter 1), DMT1 (divalent metal transporter 1)) (black bars).

Figure 6B:
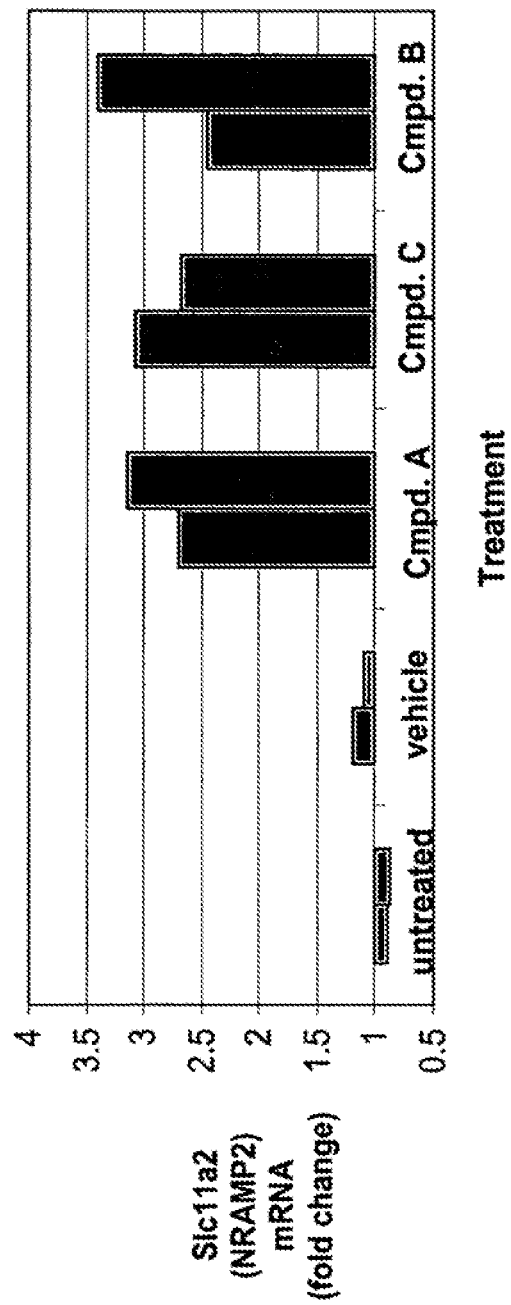

In another experiment, mRNA was isolated from small intestine harvested 4 hours following IV administration of 60 mg/kg compound A, compound B, and compound C to mice. Probes were prepared from each of two animals from 5 treatment groups, and hybridized to Affymetrix mouse MOE430Aplus2 microarrays (one animal per array). Statistical comparisons of data obtained from arrays from treated versus non-treated animals was performed. FIG. 6B shows relative expression levels of NRAMP2 mRNA in small intestine in animals treated with compound A, compound B, and compound C. Expression levels are shown as fold-induction over control, untreated animals for each expressed gene. The results from these experiments indicated that methods and compounds of the present invention are useful for increasing expression of NRAMP2 in intestine. These results further suggested that methods and compounds of the present invention are useful for increasing iron absorption, thereby increasing iron availability for heme synthesis, hemoglobin synthesis, red blood cell production, and erythropoiesis.

Figure 6C:
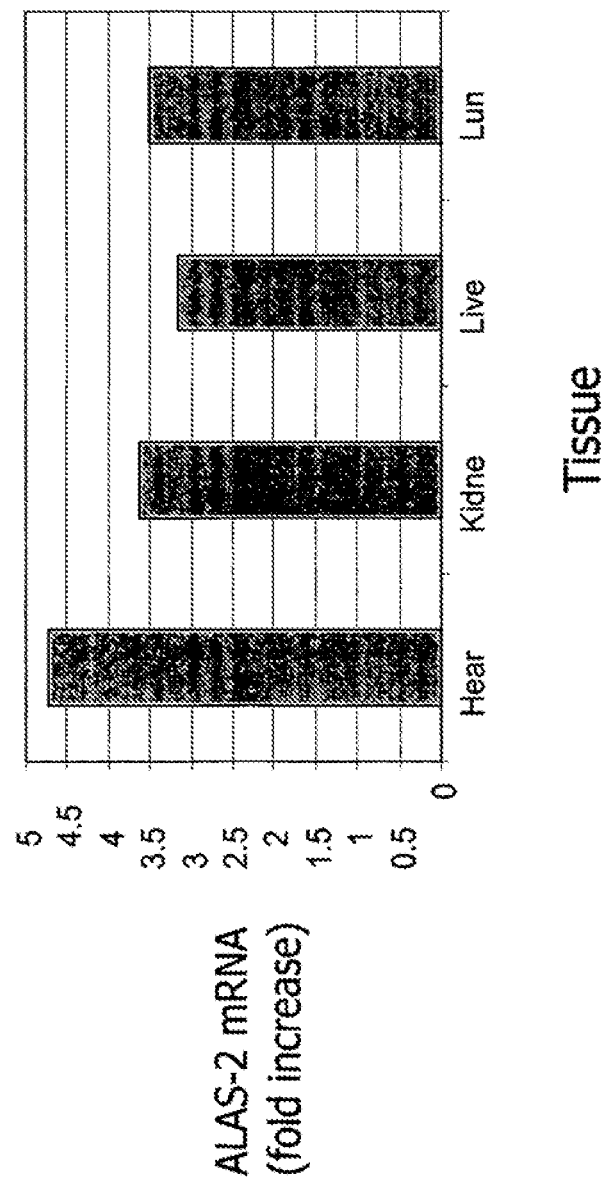

FIG. 6C shows the fold-induction of 5-aminolevulinate synthase (ALAS-2) expression in treated animals as compared to vehicle control. The data showed that treatment of normal animals with prolyl hydroxylase inhibitors resulted in increased expression of genes involved in iron metabolism, including genes involved in iron absorption from the gut and iron transport in the periphery via transferrin receptors. Expression of these genes returned to baseline (control) levels 16 hours after dosing. The data also showed coordinate expression of ALAS-2, the first enzyme in the heme synthetic pathway and rate-limiting enzyme for heme synthesis, in the indicated tissues after prolyl hydroxylase inhibitor treatment. Together these results showed compounds of the present invention coordinated increases in expression of genes encoding proteins involved in promoting erythropoiesis, including iron absorption, iron transport, and heme synthesis.

Alternatively, flow cytometry analysis is used to measure macrophage cell surface marker CD11c and transferrin receptor levels in double immunostained peripheral blood mononuclear cells. Activity is shown for compound treatment by detecting increased macrophage transferrin receptor expression. Also, plasma can be collected and tested for levels of transferrin using a commercially available ELISA kit (see, e.g., KomaBiotech, Korea).

Example 18: Enhanced Erythropoiesis In Vivo

The effect of administration of the present compounds on erythropoiesis is determined as follows. Normal mice are made anemic and maintained in an anemic state by chronic administration of TNF-α, a regimen known to inhibit erythropoiesis due to lack of EPO production and signaling in response to TNF-α. After inducing anemia over a one- to four-week period, animals are administered prolyl hydroxylase inhibitors. Tissues are examined for BFU-E and CFU-E production, and blood samples are analyzed for composition. Results showing increases in the numbers of BFU-E and CFU-E in the marrow, spleen, and periphery, and/or increases serum hemoglobin, reticulocytes, and hematocrit in animals treated with PHIs demonstrate efficacy.

Another experimental animal model is useful for examining the effect of administration of prolyl hydroxylase inhibitors on erythropoiesis. In this model, transgenic mice develop anemia of chronic disease as a result of constitutively over expressing TNF-α. Following onset of anemia in these mice, prolyl hydroxylase inhibitors are administered for various periods of time and using various dosing strategies. Tissue and blood samples are then collected and analyzed. As described above, results showing increases in the numbers of BFU-E and CFU-E in the marrow, spleen and periphery, and/or increased serum hemoglobin, reticulocytes and hematocrit, effectively demonstrate that anemia associated with TNF-α overproduction in transgenic animals is treated by administration of prolyl hydroxylase inhibitors using methods and compounds of the present invention.

Example 19: Increasing Serum Iron Levels

Male and female rats were treated twice weekly (Monday and Thursday) with various concentrations (0, 20, 60, or 150 mg/kg) of compound A for 93 days. Total serum iron levels were determined.

TABLE 5

| Dose | Serum Iron (µg/dL) Male Rats (Mean +/− SD) | Serum Iron (µg/dL) Female Rats (Mean +/− SD) |
|---|---|---|
| 0 mg/kg | 158 +/− 37 | 342 +/− 91 |
| 20 mg/kg | 198 +/− 64 | 505 +/− 41* |
| 60 mg/kg | 357 +/− 111* | 445 +/− 46* |
| 150 mg/kg | 307 +/− 142* | 399 +/− 117 |

As shown in Table 5, administration of compound A increased serum iron levels in both male and female rats. (Data in Table 5 is presented as serum iron levels+/−standard deviation. * indicates a significant difference in serum iron levels from non-treated animals.) These results indicated that methods and compounds of the present invention are useful for increasing serum iron levels, thereby useful for treating disorders associated with iron deficiency.

Example 20: Efficacy in Animal Model of Anemia of Chronic Disease/Impaired Erythropoiesis/Impaired Iron Metabolism Anemia of chronic disease (ACD) is associated with various inflammatory conditions, including arthritis, neoplastic disease, and other disorders associated with chronic inflammation. A rat model of ACD was used to examine the effects of HIF stabilization using methods and compounds of the present invention on treating anemia associated with chronic disease. In this animal model, ACD is induced in rats by peptidoglycan-polysaccharide polymers. (See, e.g., Sartor et al. (1989) Infection and Immunity 57:1177-1185.) In this model, animals develop severe, acute anemia in the initial stages, followed by moderately severe chronic microcytic anemia in later stages.

Animal Model of ACD—Experimental Series 1:

Female Lewis rats of approximately 160 grams were challenged with PG-PS 10S (Lee Laboratories, 15 µg/gm body weight, intra-peritoneal). PG-PS 10S contains purified peptidoglycan-polysaccharide polymers isolated from the cell wall of *Streptococcus pyogenes*, Group A, D58 strain. Arthritis and anemia were allowed to develop for 35 days.

On day 35, blood samples (approximately 400 μl) were taken from the tail vein under general anesthesia (Isoflurane) for CBC and reticulocyte counts (performed by Quality Clinical Labs). Animals with a spun hematocrit level at or above 45% were considered non-anemic and were removed from the study.

On day 35 following PG-PS injection, anemic animals received vehicle alone or were treated with compound A (60 mg/kg, PO) for two consecutive days per week for two weeks. Automated complete blood counts (CBC) were measured on day 35 (see above), 39, 42, and 49; serum iron levels were measured on day 49.

Reticulocyte Count

Figure 7:
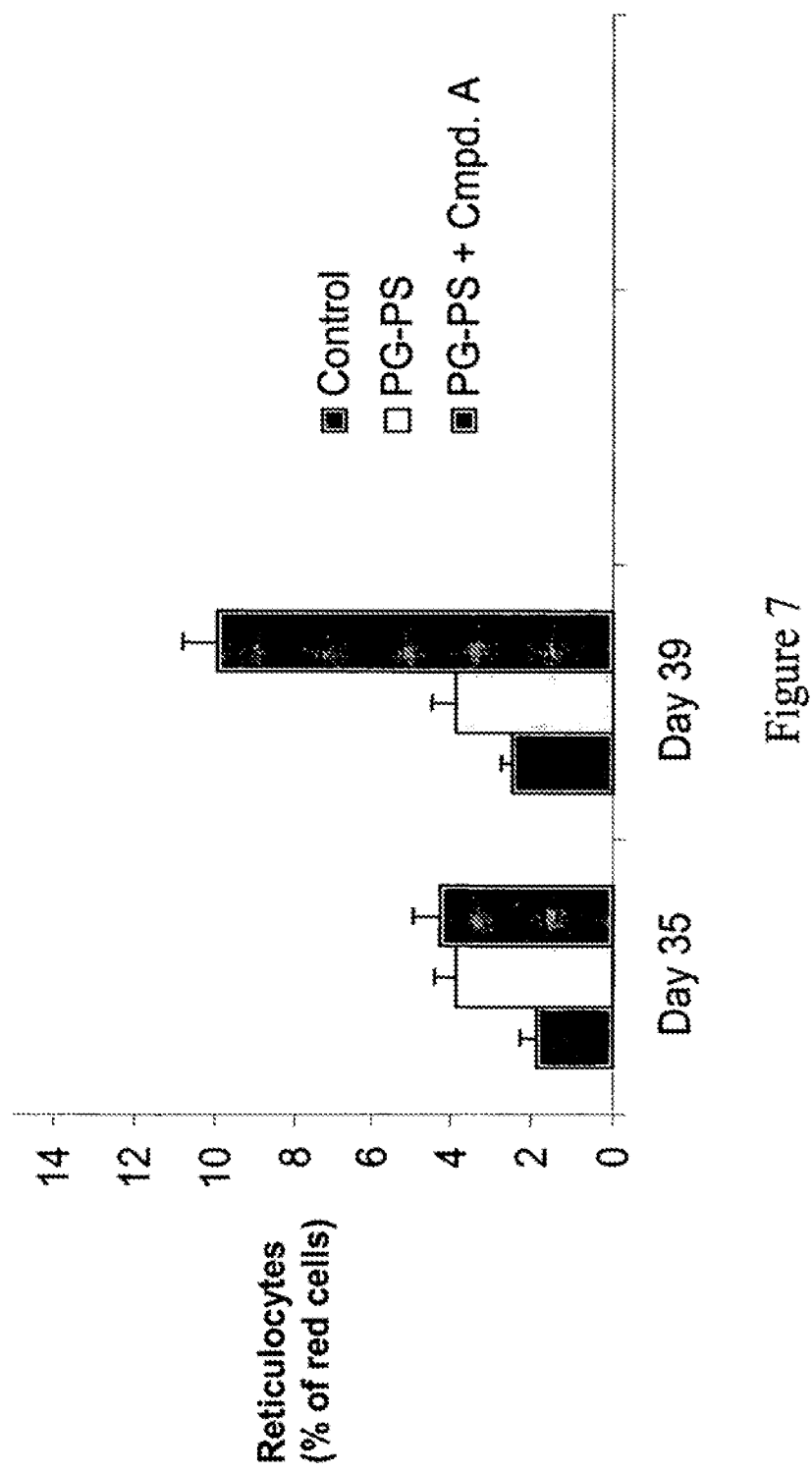
FIG. 7 sets forth data showing methods and compounds of the present invention increased reticulocyte counts in an animal model of anemia of chronic disease.

As shown in FIG. 7, administration of compound A to anemic animals increased reticulocyte count at day 39 (i.e., 5 days after initiation of compound dosing). Reticulocytes levels were approximately 2% and 4% of red cells in control (non-anemic) and anemic (PG-PS treated) animals, respectively. Reticulocyte levels in treated animals, however, were approximately 10% of red cell counts. Compound A treatment increased reticulocyte count in anemic animals. Therefore, compound A stimulated erythropoiesis in a rat animal model of ACD.

Hematocrit

Figure 8:
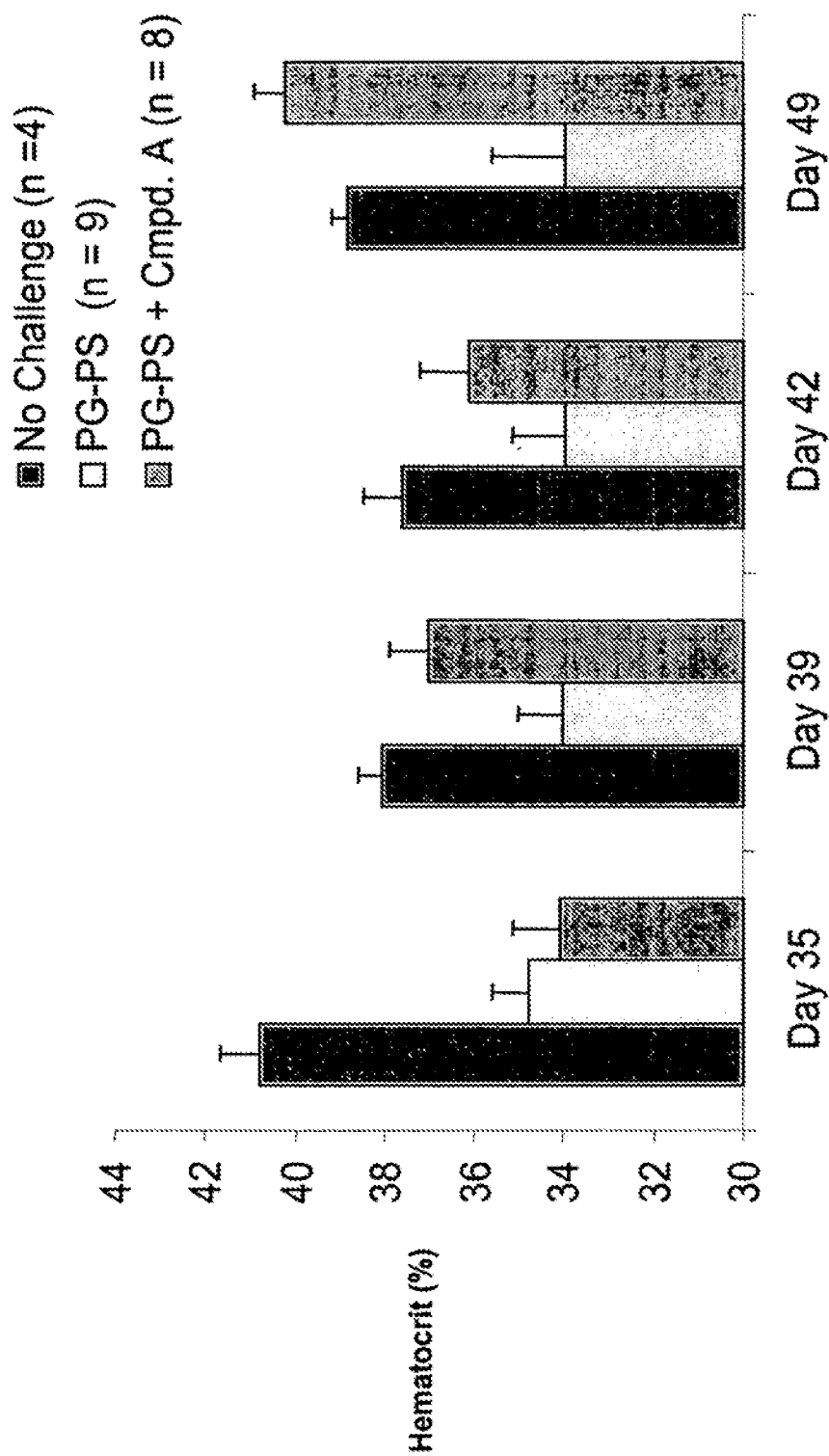
FIG. 8 sets forth data showing methods and compounds of the present invention increased hematocrit in an animal model of anemia of chronic disease.

Hematocrit levels were increased in anemic animals treated with compound A. Hematocrit levels (measured by Baker 9000 at Quality Clinical Labs) in anemic animals (PG-PS treated) were less than 35%, compared to 41% in control non-anemic animals (See FIG. 8.) Administration of compound A to anemic animals increased hematocrit levels to approximately 37% as early as 5 days after initiation of compound treatment. Following a second dosing of compound A, hematocrit levels increased to approximately 40%, comparable to hematocrit levels observed in control non-anemic animals. Compound A increased hematocrit in anemic animals using a rat model of ACD. Therefore, methods and compounds of the present invention are useful for increasing hematocrit and treating anemia of chronic disease.

Hemoglobin

Figure 9:
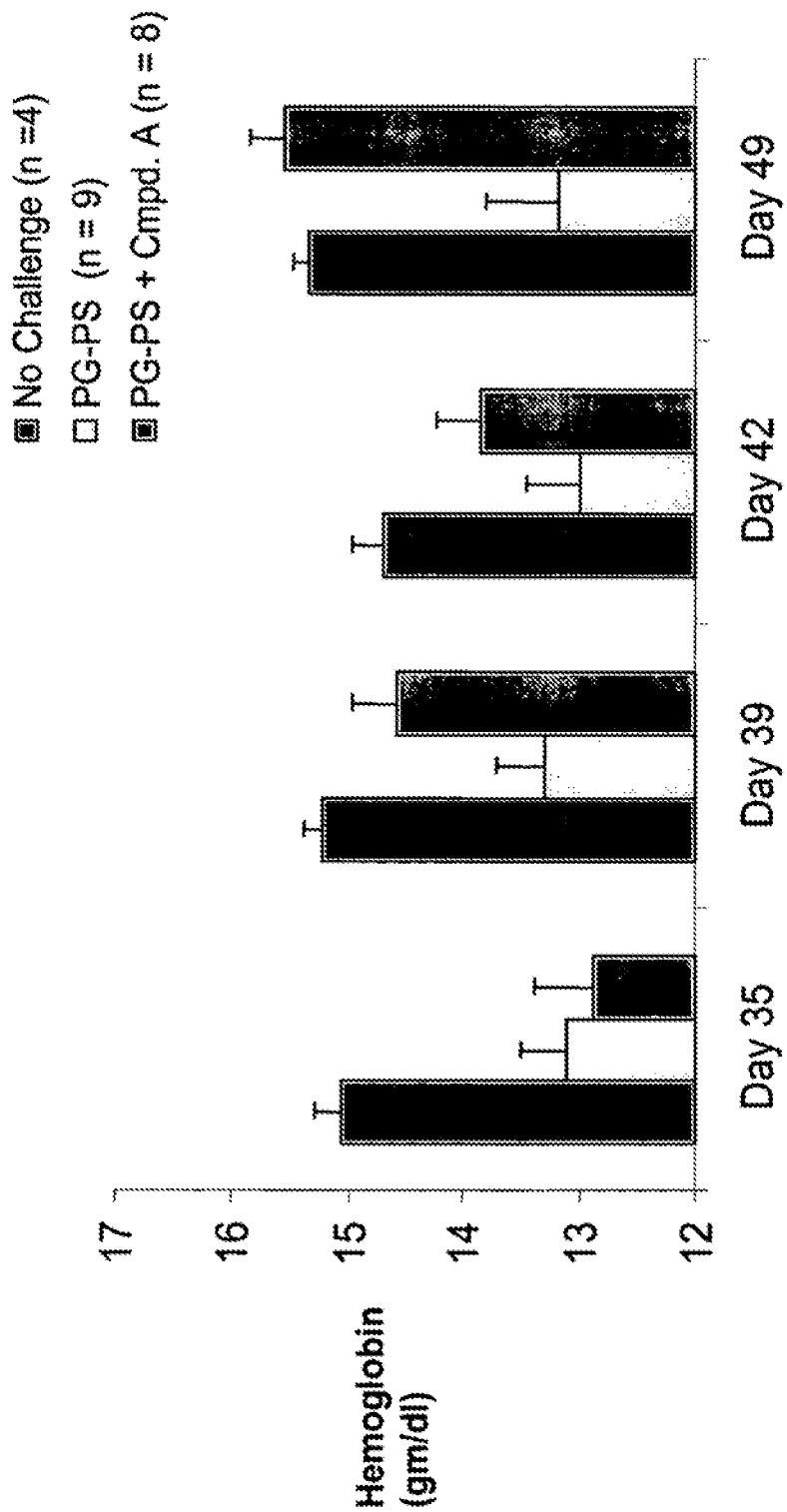
FIG. 9 sets forth data showing methods and compounds of the present invention increased hemoglobin levels in an animal model of anemia of chronic disease.

Compound A administration also increased hemoglobin levels in anemic animals. As shown in FIG. 9, at day 35, control non-anemic animals had hemoglobin levels of approximately 15 gm/dL, whereas hemoglobin levels in PG-PS treated animals (i e, anemic animals) were approximately 13 gm/dL. As shown in FIG. 9, compound A increased hemoglobin levels in anemic animals as early as 5 days (day 39) following compound administration. Hemoglobin levels remained elevated at day 49, reaching a level comparable to control non-anemic animals, indicating compound of the present invention restored normal hemoglobin levels in anemic animals. These results showed compound A increased hemoglobin in anemic animals using a rat model of ACD. Therefore, methods and compounds of the present invention are useful for increasing hemoglobin and treating anemia of chronic disease.

Red Blood Cell Count

Figure 10:
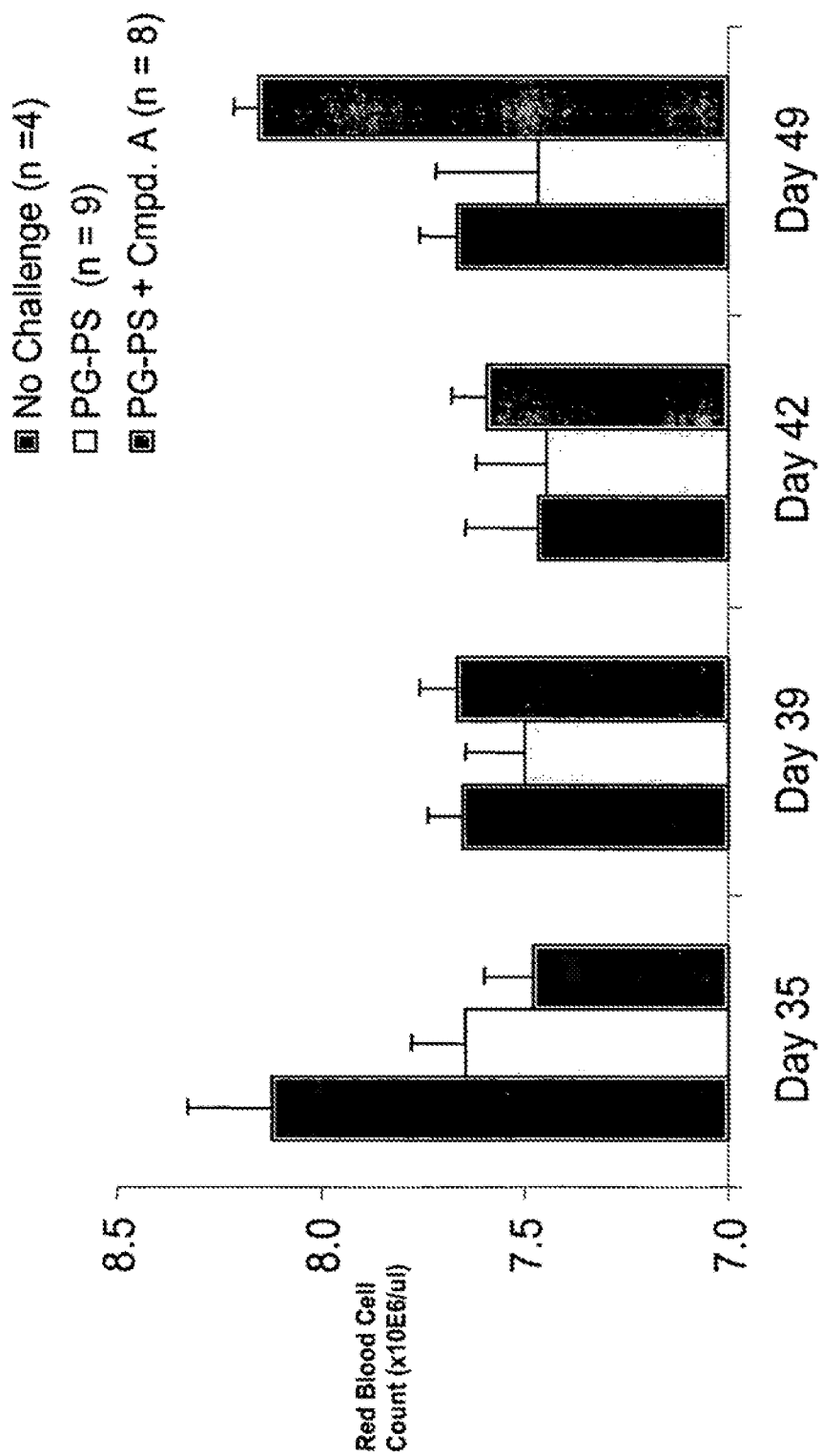
FIG. 10 sets forth data showing methods and compounds of the present invention increased red cell count in an animal model of anemia of chronic disease.

Administration of compound A increased red blood cell count in anemic animals. As shown in FIG. 10, red blood cell counts were increased in anemic animals treated with compound A compared to non-treated anemic animals as early as 5 days after initiation of compound administration (i.e., day 39 in FIG. 10). Compound A increased red blood cell count in anemic animals using a rat model of ACD. Therefore, methods and compounds of the present invention are useful for increasing red blood cell count and treating anemia of chronic disease.

Mean Corpuscular Volume

Figure 11:
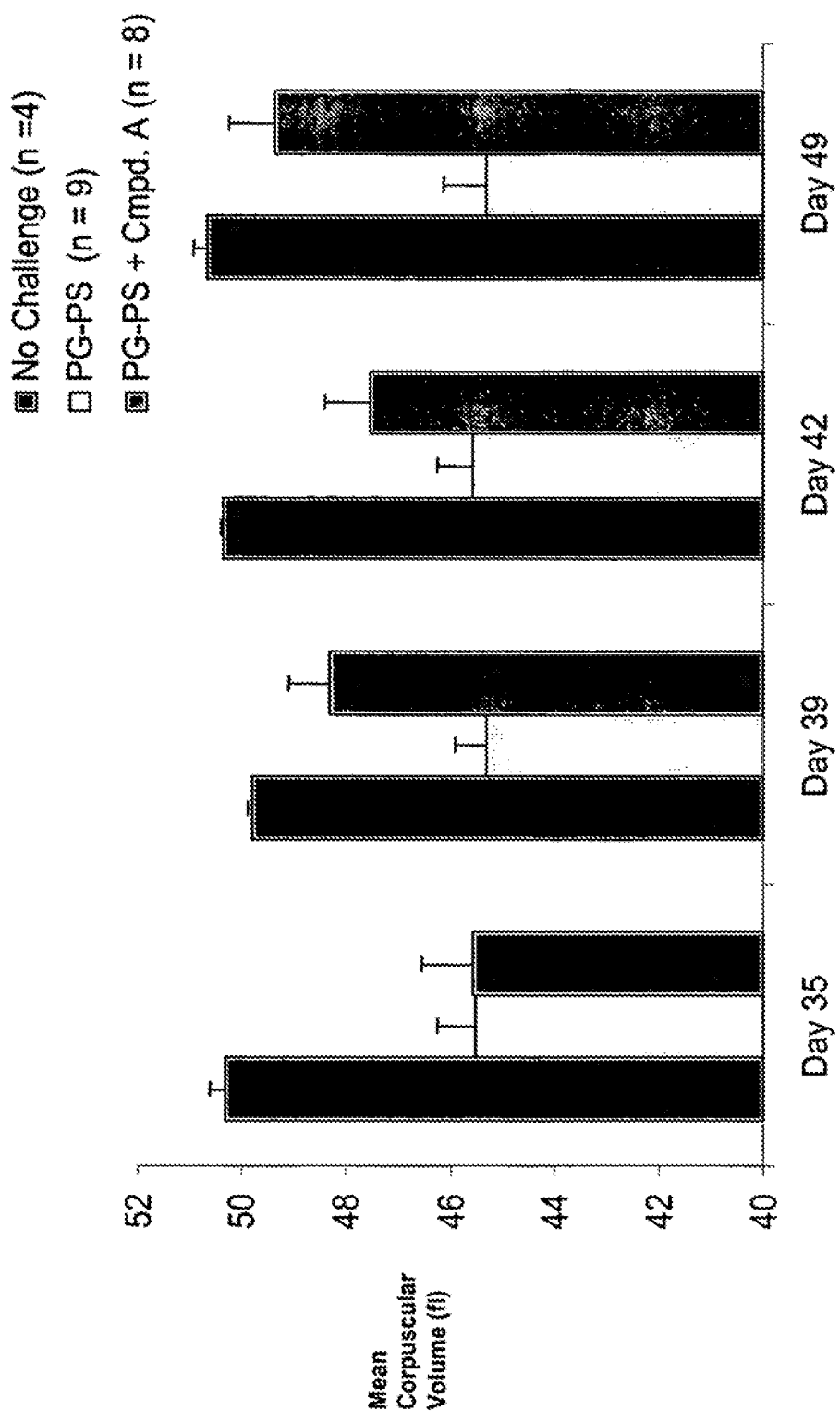
FIG. 11 sets forth data showing methods and compounds of the present invention reduced microcytosis in an animal model of anemia of chronic disease.

Anemic animals showed reduced mean corpuscular volume compared to non-anemic control animals (See FIG. 11.) Anemic animals treated with compound A showed increased mean corpuscular volume as early as 5 days after treatment (day 39 in FIG. 11) compared to non-treated anemic animals Mean corpuscular volume in treated animals remained elevated compared to non-treated anemic animals over the duration of the experiment. These results showed that compound A improved (i.e., reduced) the level of microcytosis (i.e., microcythemia, the presence of many microcytes, abnormally small red blood cells associated with various forms of anemia). Therefore methods and compounds of the present invention improve/reduce microcytosis in anemia of chronic disease.

Mean Corpuscular Hemoglobin

Figure 12:
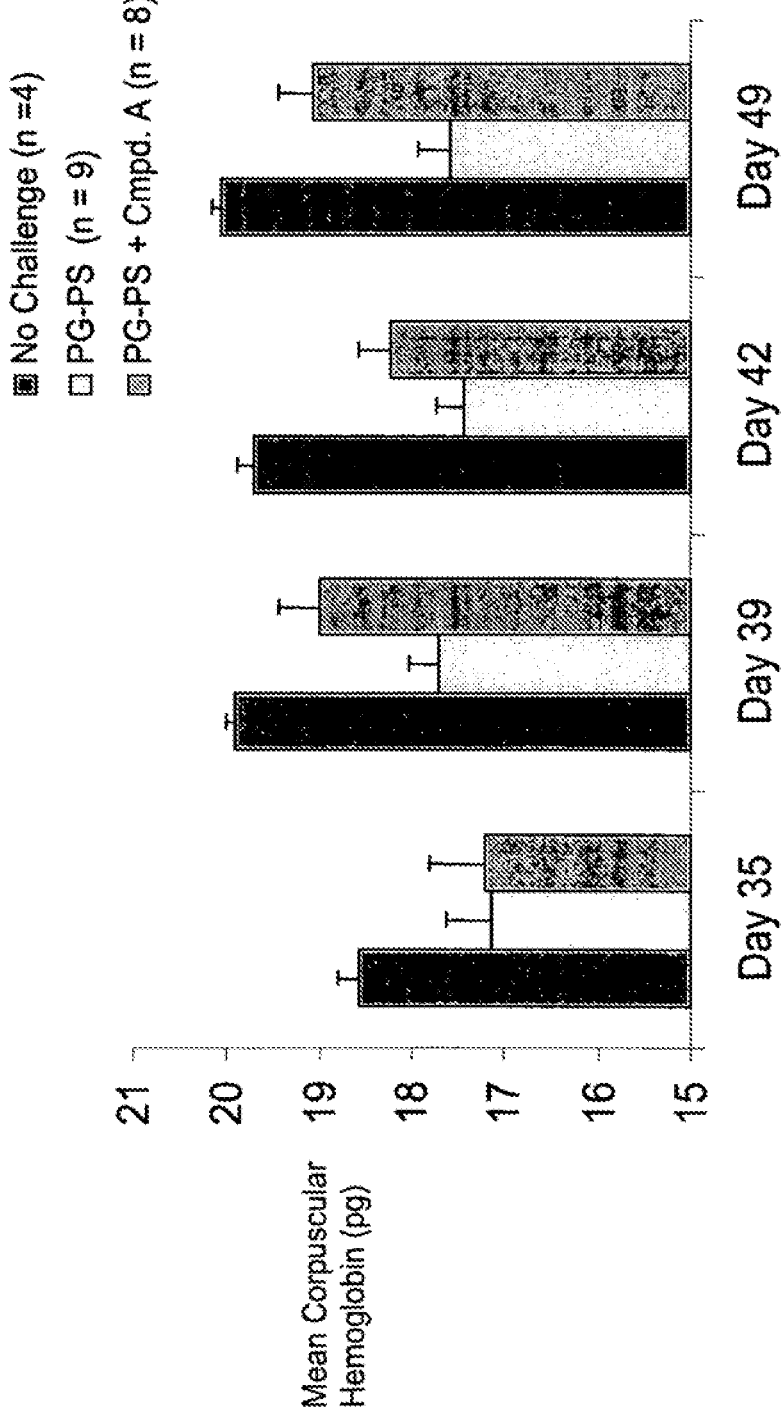
FIG. 12 sets forth data showing methods and compounds of the present invention increased mean corpuscular hemoglobin and improved hypochromia in an animal model of anemia of chronic disease.

Anemic animals also showed reduced mean corpuscular hemoglobin levels. As shown in FIG. 12, treatment of anemic animals with compound A increased mean corpuscular hemoglobin levels above those observed in non-treated anemic animals. These results indicated that methods and compounds of the present invention are useful to increase mean corpuscular hemoglobin levels.

Animal Model of ACD—Experimental Series 2:

Female Lewis rats (approximately 150-200 gm) were injected with PG-PS (intra-peritoneal). Arthritis and anemia were allowed to develop for 28 days Animals were administered compound A by oral gavage twice a week (Monday and Thursday) for six weeks, corresponding to days 28, 31, 35, 38, 42, 45, 49, 52, 56, 59, 63, 66, and 70 from PG-PS injection.

Whole blood was collected via the tail vein for CBC analysis on days 28, 42, 56, and 70. In addition, serum was collected on day 70 for iron binding analysis. CBC and iron binding analysis were performed by Quality Clinical Labs (Mountain View, Calif.).

Hematocrit

Figure 13:
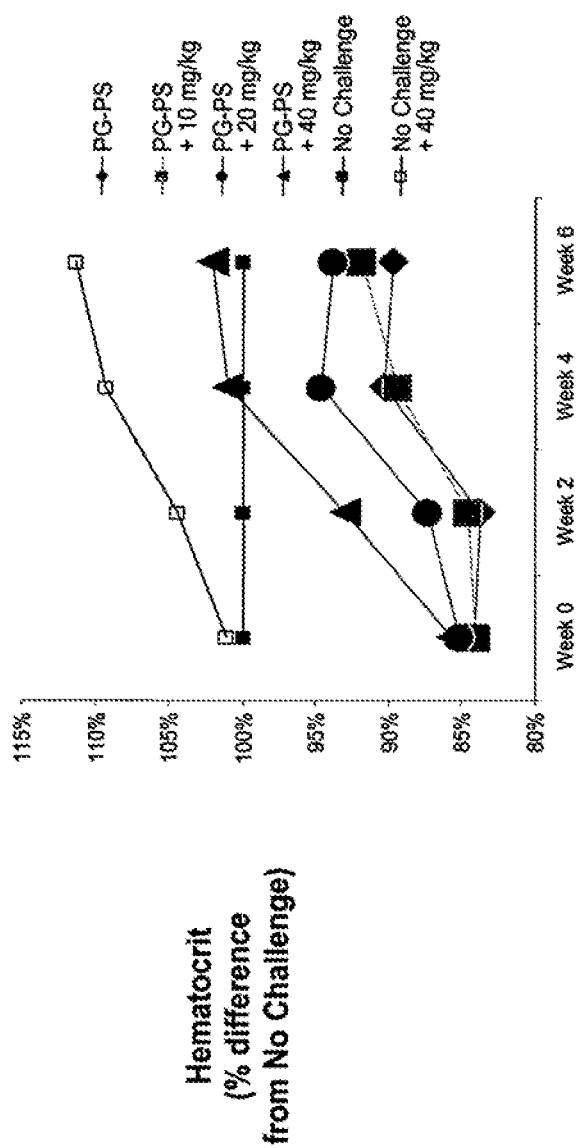
FIG. 13 sets forth data showing methods and compounds of the present invention increased hematocrit in normal animals and in an animal model of anemia of chronic disease.

Hematocrit levels were reduced in animals 28 days following challenge with PG-PS. FIG. 13 shows animals injected with PG-PS were anemic, having a hematocrit of 85% of that in non-challenged (i.e., non-anemic) animals. (Week 0 in FIG. 13 corresponds to day 28 in this experimental protocol.) Non-challenged (i.e., non-anemic) animals treated with compound A (40 mg/kg) showed an increase in hematocrit levels over time, to greater than 110% of that in non-challenged non-treated animals. As shown in FIG. 13, administration of compound A to anemic animals resulted in increased hematocrit levels.

Hemoglobin

Figure 14:
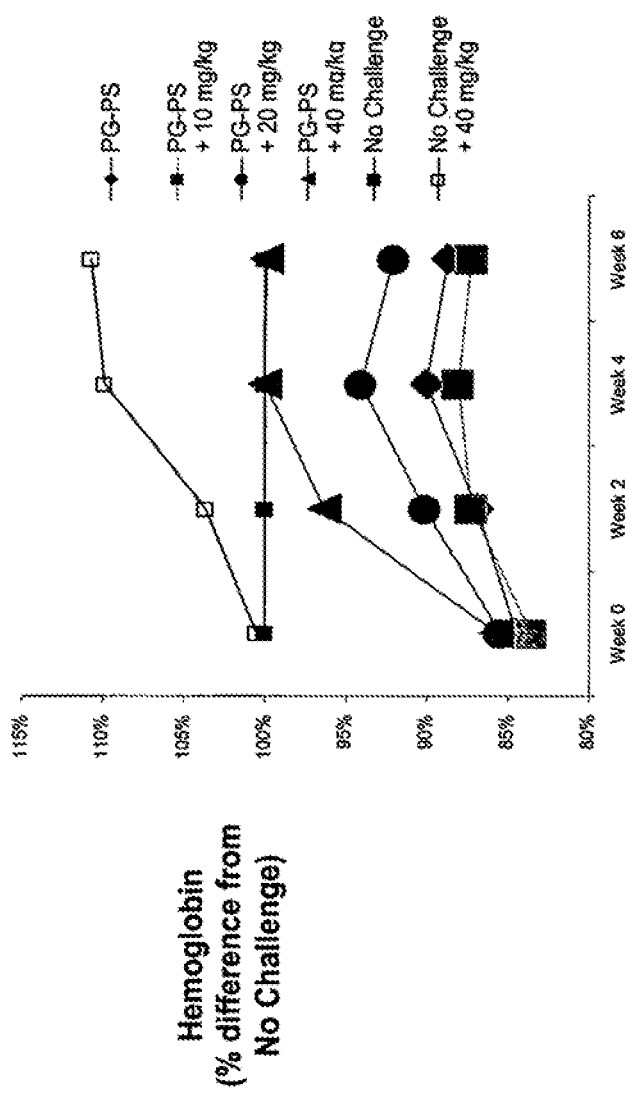
FIG. 14 sets forth data showing methods and compounds of the present invention increased hemoglobin levels in normal animals and in an animal model of anemia of chronic disease.

Compound A administration increased hemoglobin levels in both anemic and non-anemic animals. As shown in FIG. 14, hemoglobin levels in non-anemic animals treated with compound A (40 mg/kg) increased to approximately 110% of that in non-treated control animals (Week 0 in FIG. 14 corresponds to day 28 in this experimental protocol.) In anemic animals, hemoglobin levels increased upon administration twice weekly of 10 mg/kg, 20 mg/kg, or 40 mg/kg compound A. Hematocrit levels continued to increase for at least 4 weeks.

Red Blood Cell Count

Figure 15:
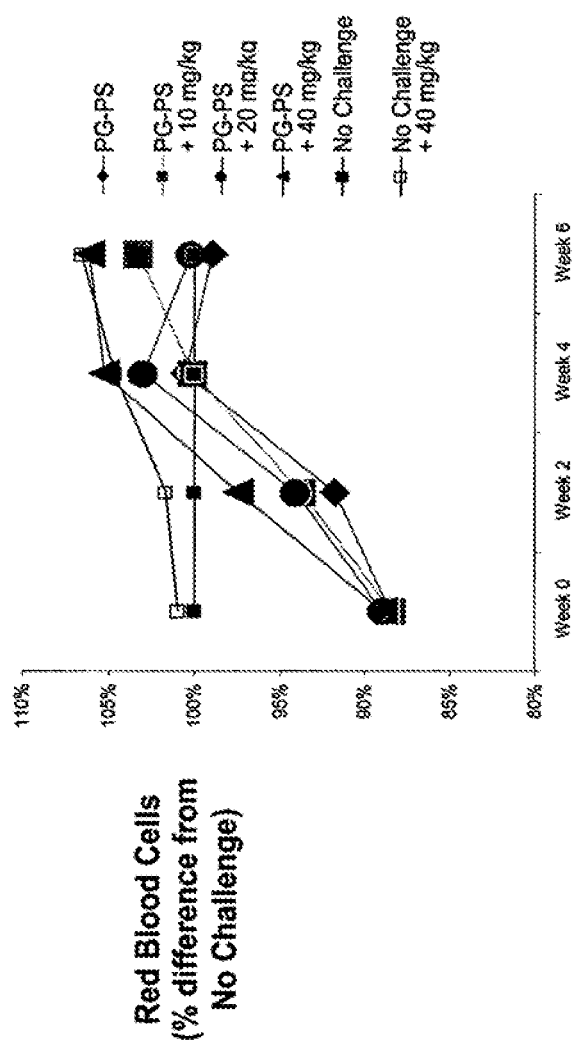
FIG. 15 sets forth data showing methods and compounds of the present invention increased red blood cell counts in normal animals and in an animal model of anemia of chronic disease.

Anemic animals had lower red blood cell counts than non-anemic animals Specifically, red blood cell counts in anemic animals were less than 90% of that observed in non-anemic animals at 28 days following PG-PS injection. As shown in FIG. 15, red blood cell counts were increased in anemic animals treated with compound A compared to non-treated animals. (Week 0 in FIG. 15 corresponds to day 28 in this experimental protocol.) Increased red blood cell counts were observed at 2 weeks following administration of compound, and continued to increase over the 6 week experimental period.

Mean Corpuscular Volume

Figure 16:
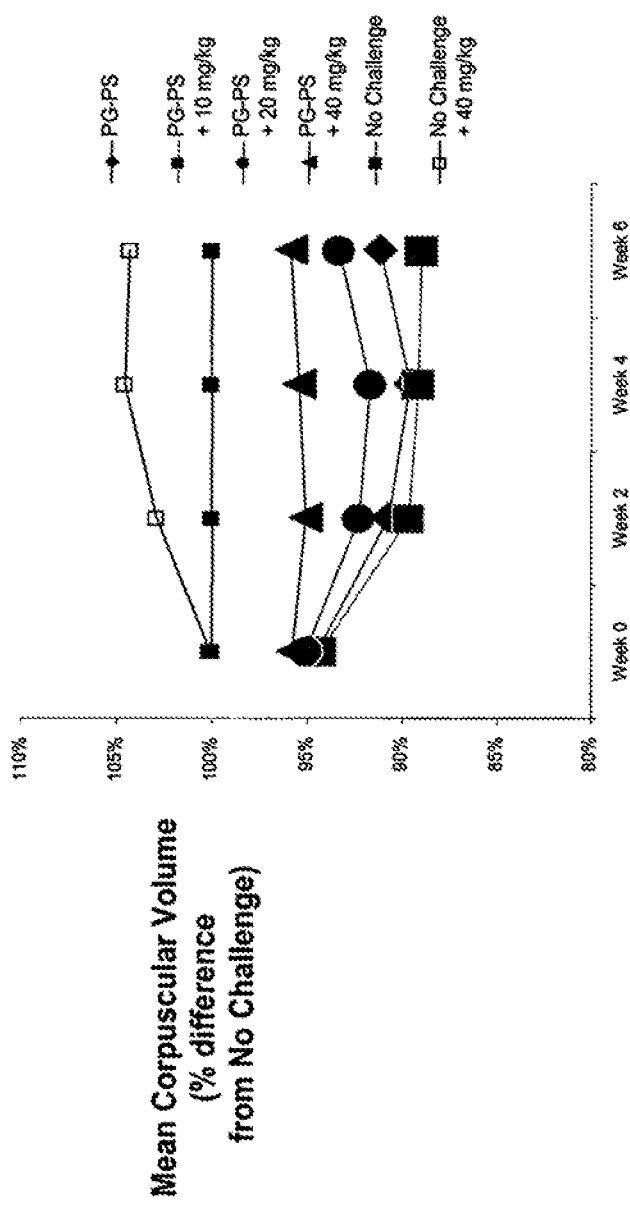
FIG. 16 sets forth data showing methods and compounds of the present invention improved mean corpuscular volume in normal animals and in an animal model of anemia of chronic disease.

Anemic animals showed reduced mean corpuscular volume compared to non-anemic (no challenge) animals. As shown in FIG. 16, mean corpuscular volume in animals treated with PG-PS continued to decrease over time, indicating the effects of anemia of chronic disease resulted in microcytic anemia (characterized, in part, by lower red cell number and smaller red cells), and the inability to produce hemoglobin due to iron stores being unavailable for utilization. (Week 0 in FIG. 16 corresponds to day 28 in this experimental protocol.) Administration of compound A to anemic animals resulted in reduction of the decrease in mean corpuscular volume. Therefore, inhibition of prolyl hydroxylase using compounds and methods of the present invention was effective at reducing the decrease in mean corpuscular volume associated with anemia of chronic disease and anemia associated with iron deficiency, restoring mean corpuscular volume, maintaining mean corpuscular volume, etc. This data further indicated that methods and compounds of the present invention are useful for increasing iron availability from storage for use in hemoglobin production.

Mean Corpuscular Hemoglobin

Figure 17:
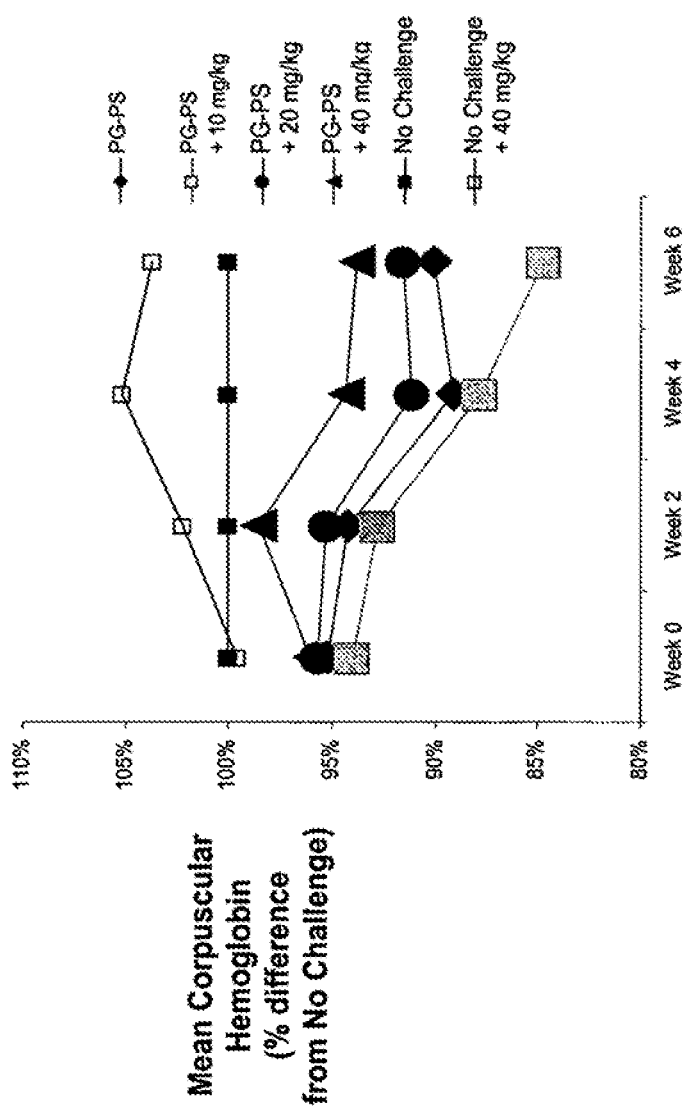
FIG. 17 sets forth data showing methods and compounds of the present invention improved mean corpuscular hemoglobin levels in normal animals and in an animal model of anemia of chronic disease.

Anemic animals had decreased mean corpuscular hemoglobin levels compared to control animals, indicating anemia of chronic disease affected hemoglobin production. As shown in FIG. 17, anemic animals administered compound A showed a reduction in the decrease in mean corpuscular hemoglobin levels over time. (Week 0 in FIG. 17 corresponds to day 28 in this experimental protocol.)

Iron Status—Serum Iron and Transferrin Saturation

Patients with anemia of chronic disease are clinically characterized by reduced plasma iron concentrations and transferrin saturation. The effect of the present compounds on serum iron and transferrin saturation in normal and anemic animals was determined. Using an animal model of anemia of chronic disease, anemia was induced in rats by IP injection of peptidoglycan-polysaccharide polymers, as described above. Arthritis and anemia were allowed to develop for 28 days Animals were then treated with various concentrations of compound A, twice weekly, for 6 weeks. Serum iron levels and transferrin saturation were determined by Quality Clinical Labs.

Figure 18A:
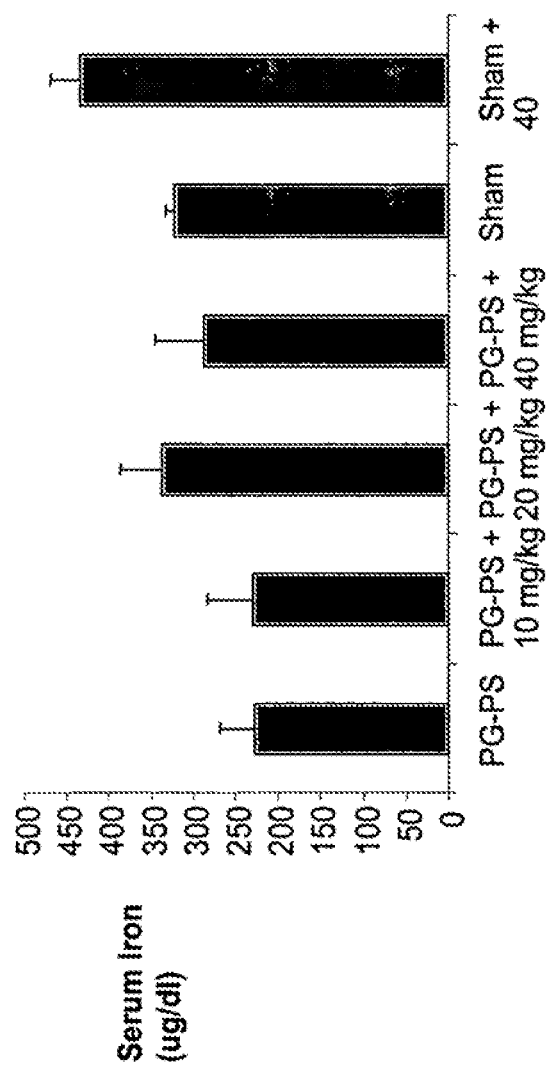
FIGS. 18A and 18B set forth data showing methods and compounds of the present invention increased serum iron levels (FIG. 18A) and transferrin saturation (FIG. 18B) in normal animals and in an animal model of anemia of chronic disease.
Figure 18B:
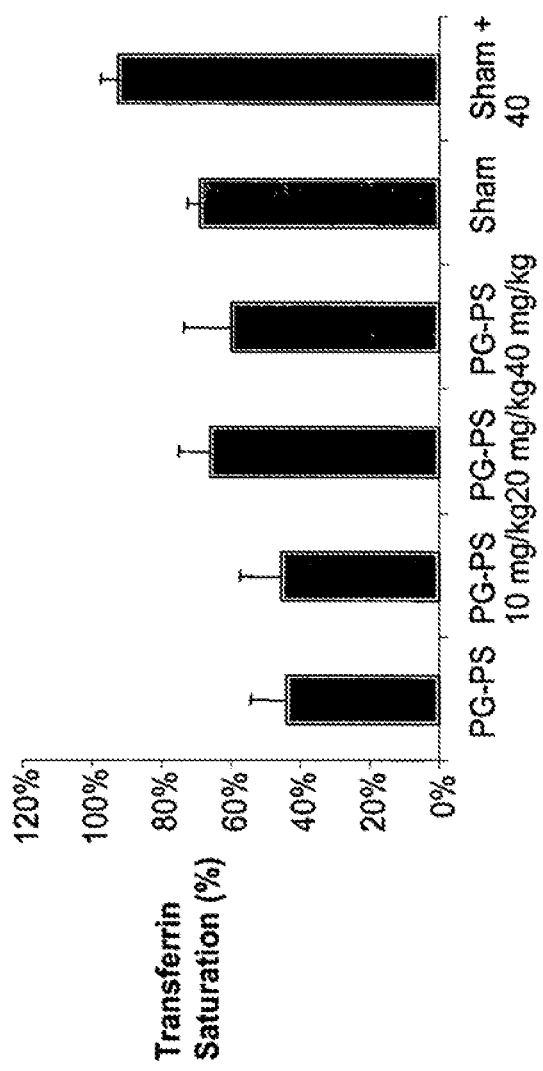

As shown in FIG. 18A, anemic animals (PG-PS) had lower serum iron levels compared to non-anemic animals (sham). Administration of compound A resulted in increased serum iron levels in both anemic (PG-PS) and non-anemic control (sham) animals Animals treated with compound A had increased transferrin saturation compared to non-treated non-anemic animals and to non-treated anemic animals (See FIG. 18B.) These results indicated that methods and compounds of the present invention are useful for increasing serum iron levels and percent transferrin saturation.

Iron Absorption

At week 6 following administration of compound A in anemic animals (40 mg/kg, twice a week), microarray analysis was performed to examine expression of genes encoding proteins involved with iron transport and absorption in intestine. Microarray analysis was performed using methods described above, using The Rat Genome 230A array (Affymetrix), which represents all sequence in the Rat Unigene database build 99 (National Center for Biotechnology Information, Bethesda, Md.), including approximately 4,699 well-characterized rat genes and approximately 10,467 EST sequences and approximately 700 non-EST sequences.

Figure 19:
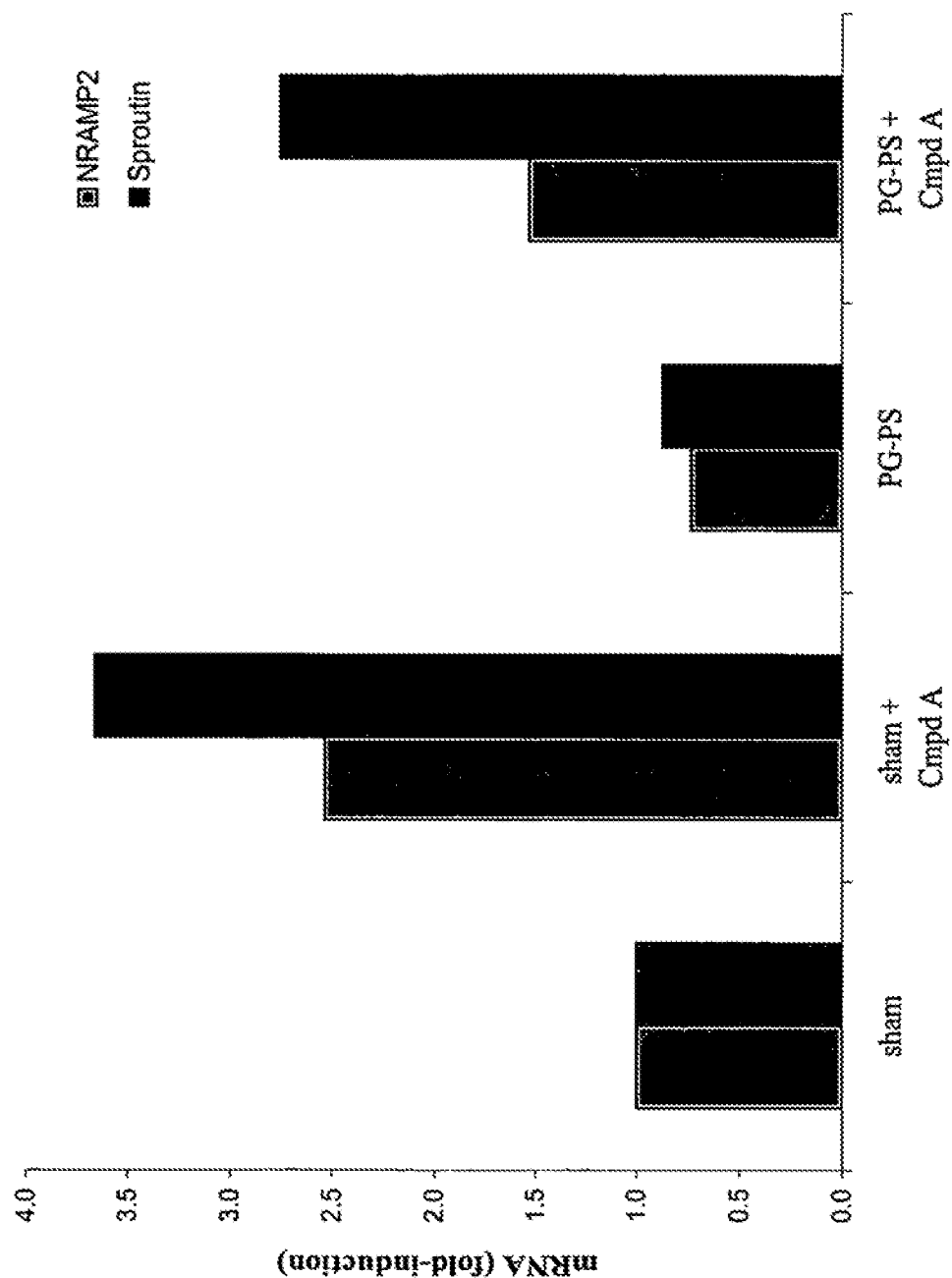
FIG. 19 sets forth data showing methods and compounds of the present invention increased gene expression of NRAMP2 (slc112a) and sproutin (CYBRD1, duodenal cytochrome b reductase 1) in normal animals and in an animal model of anemia of chronic disease.

As shown in FIG. 19, administration of compound A to control animals increased intestinal expression of mRNA for NRAMP2 (open bars) and sproutin (solid bars). Non-treated anemic animals (PG-PS) had reduced mRNA expression levels for both NRAMP2 and sproutin. These results indicated that anemia of chronic disease is associated with reduced expression of proteins involved in iron absorption. Anemic animals treated with compound A, however, showed increased expression of both NRAMP2 and sproutin in intestine (FIG. 19). These results indicated that methods and compounds of the present invention are useful for increasing expression of genes associated with iron transport and absorption. Additionally, these results suggested that compounds of the present invention increase iron absorption and transport in healthy subjects and in subjects with anemia of chronic disease.

Example 21: Enhanced Erythropoiesis in Human Subjects

The effect of prolyl hydroxylase inhibition on erythropoiesis in human subjects was examined as follows. An oral dose of 20 mg/kg of compound A was administered either two or three times per week for four weeks to healthy human volunteers. At various times following compound administration, blood was drawn for analysis of EPO, hemoglobin, hematocrit, red blood cell counts, soluble transferrin receptor, and serum ferritin levels.

Reticulocyte Count

Figure 20:
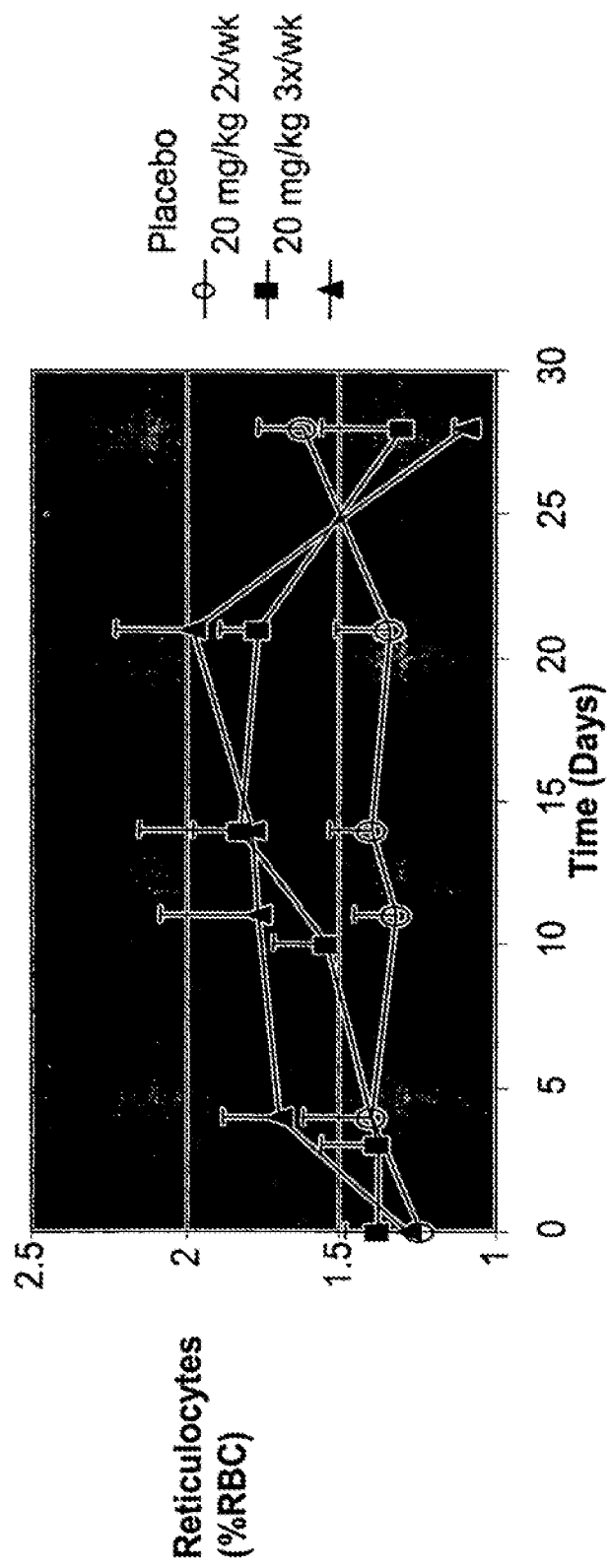
FIG. 20 sets forth data showing increased reticulocytes following administration of compound of the present invention to healthy human subjects.

As shown in FIG. 20, administration of compound A to human subjects increased reticulocyte counts above that of placebo control. Increased reticulocyte counts occurred in subjects administered compound twice or three-times weekly. Reticulocyte levels increased to greater than approximately 1.7% of red blood cells in treated individuals, compared to levels of approximately 1.4% in non-treated individuals. Compound A administration increased reticulocyte counts in human subjects. Therefore, methods and compounds of the present invention are useful for enhancing erythropoiesis and thereby increasing reticulocyte levels.

Hematocrit

Hematocrit levels were increased in human subjects treated with compound A. In human subjects administered compound A twice weekly for three weeks, hematocrit levels were greater than 46% compared to approximately 44% in placebo control subjects. Compound A increased hematocrit in human subjects. Therefore, compounds and methods of the present invention are useful for enhancing erythropoiesis and thereby increasing hematocrit.

Red Blood Cell Count

Figure 21:
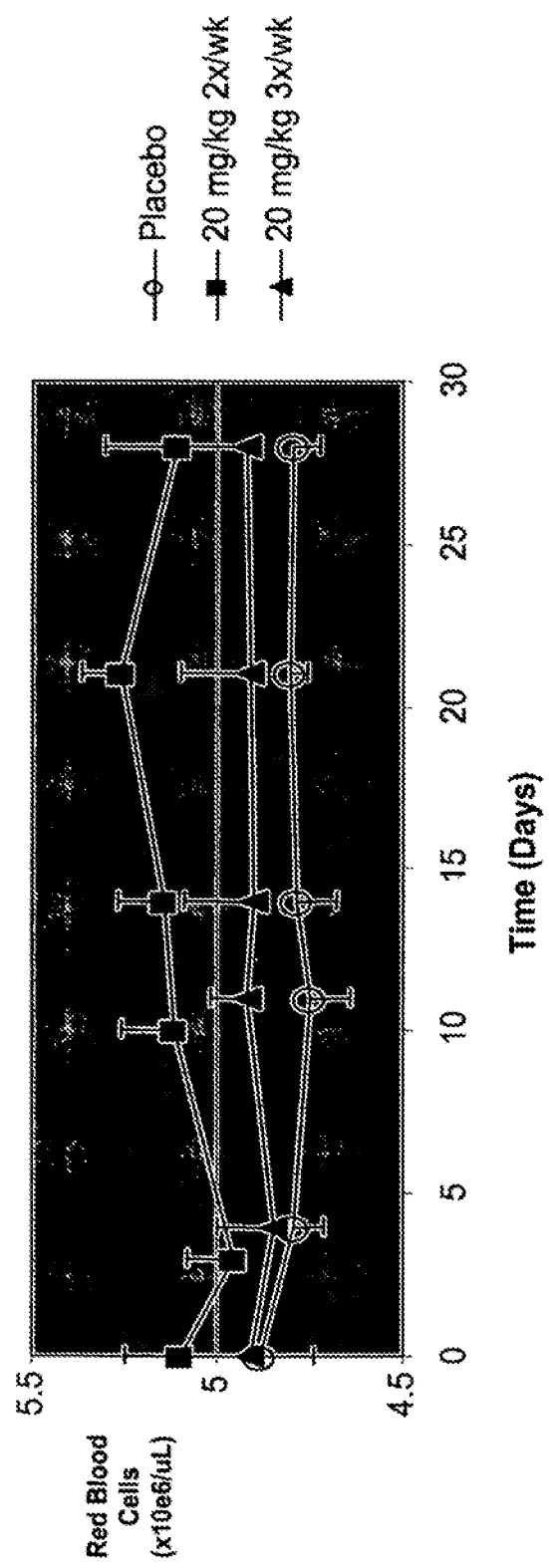
FIG. 21 sets forth data showing increased red blood cell counts in healthy human subjects administered compound of the present invention.

Administration of compound A increased red blood cell count in human subjects. As shown in FIG. 21, red blood cell counts were increased in human subjects treated with 20 mg/kg compound A, either twice weekly or three-times per week, compared to non-treated placebo control subjects. These data indicated that methods and compounds of the present invention are useful for enhancing erythropoiesis and thereby increasing red blood cell count.

Iron Status—Soluble Transferrin Receptor and Serum Ferritin

Figure 22:
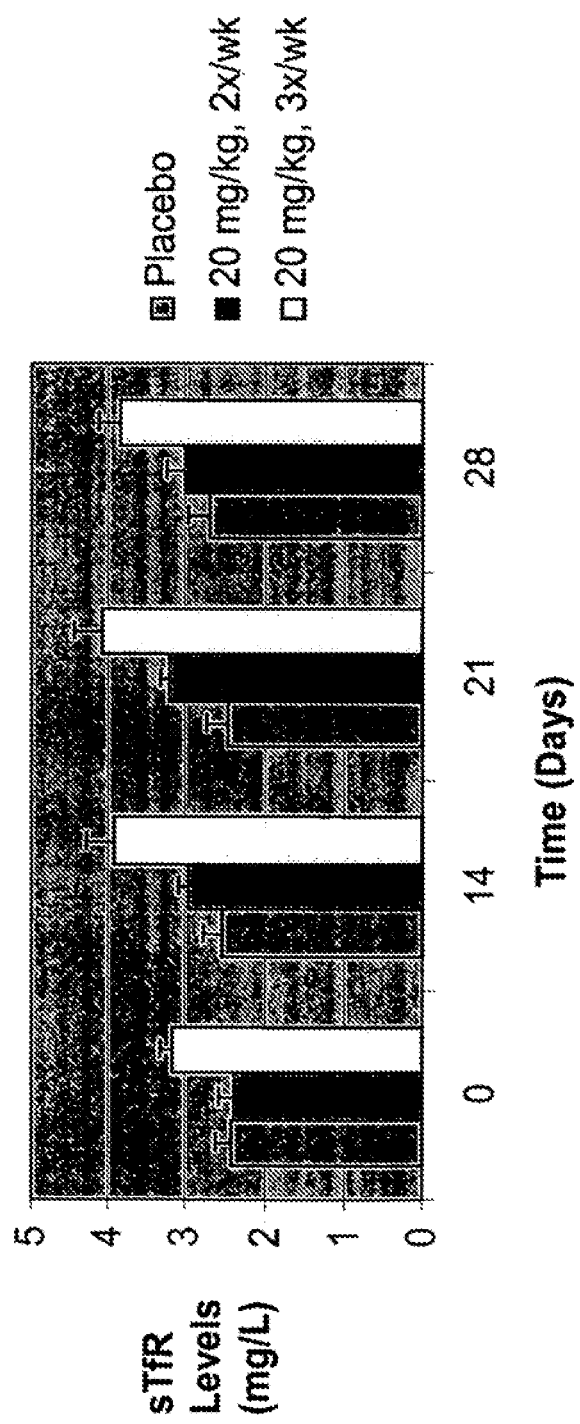
FIG. 22 sets forth data showing increased soluble transferrin receptor levels following administration of compound of the present invention to healthy human subjects.
Figure 23:
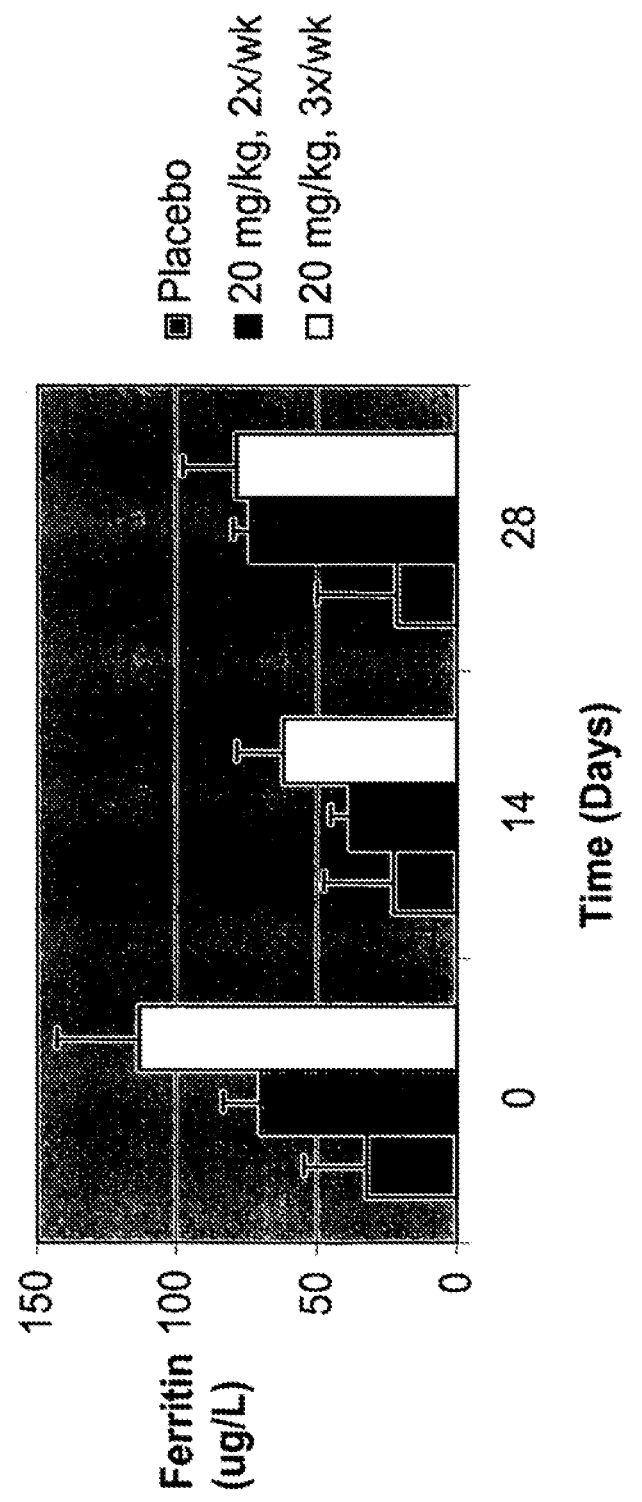
FIG. 23 sets forth data showing decreased serum ferritin levels in healthy human subjects administered compound of the present invention.

Results shown above indicated methods and compounds of the present invention are effective at increasing reticulocyte count, red blood cells, hemoglobin, and hematocrit in human subjects. As shown in FIG. 22, administration of compound A to human subjects increased soluble transferrin receptor levels above that observed in non-treated control subjects. Increased soluble transferrin levels were observed human subjects treated twice or three-times weekly. A maximum response of 35% and 31% was observed on day 21 in patients treated 2-times and 3-times per week, respectively. Mean plasma concentrations of sTfR in placebo patients was unchanged. Additionally, serum ferritin levels decreased approximately 46% in human subject treated with compound A, indicative of increased iron utilization in these subjects. (See FIG. 23.)

Taken together, these data indicated that HIF stabilization using compounds and methods of the present invention resulted in increased mobilization of iron stores, increased transport of iron to bone marrow, and increased utilization of iron for hemoglobin synthesis, erythropoiesis, and red cell production.

Various modifications of the invention, in addition to those shown and described herein, will become apparent to those skilled in the art from the foregoing description. Such modifications are intended to fall within the scope of the appended claims.

All references cited herein are hereby incorporated herein by reference in their entirety.

What is claimed is:

1. A method of treating anemia in a human subject comprising administering to the human subject an effective amount of a compound, wherein the human subject has a transferrin saturation (TSAT) level below 20% prior to said administering and wherein the compound is a compound of Formula I

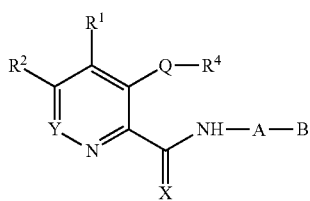

(I)

wherein
A is —$CR^5R^6$— and $R^5$ and $R^6$ are each hydrogen;
B is —$CO_2H$;
X is O;
Q is O;
$R^4$ is hydrogen
Y is $CR^3$;
$R^1$, $R^2$ and $R^3$ are identical or different and are hydrogen, hydroxyl, halogen, cyano, trifluoromethyl, nitro, carboxyl, ($C_1$-$C_{20}$)-alkyl, ($C_3$-$C_8$)-cycloalkyl, ($C_3$-$C_8$)cycloalkyl-($C_1$-$C_{12}$)-alkyl, ($C_3$-$C_8$)-cycloalkoxy, ($C_3$-$C_8$)-cycloalkyl-($C_1$-$C_{12}$)-alkoxy, ($C_3$-$C_8$)-cycloalkyloxy-($C_1$-$C_{12}$)-alkyl, ($C_3$-$C_8$)-cycloalkyloxy-($C_1$-$C_{12}$)-alkoxy, ($C_3$-$C_8$)-cycloalkyl-($C_1$-$C_8$)-alkyl-($C_1$-$C_6$)-alkoxy, ($C_3$-$C_8$)-cycloalkyl-($C_1$-$C_8$)-alkoxy-($C_1$-$C_6$)-alkyl, ($C_3$-$C_8$)-cycloalkyloxy-($C_1$-$C_8$)-alkoxy-($C_1$-$C_6$)-alkyl, ($C_3$-$C_8$)-cycloalkoxy-($C_1$-$C_8$)-alkoxy-($C_1$-$C_8$)-alkoxy, ($C_6$-$C_2$)-aryl, ($C_7$-$C_{16}$)-aralkyl, ($C_7$-$C_{16}$)-aralkenyl, ($C_7$-$C_{16}$)-aralkynyl, ($C_2$-$C_{20}$)-alkenyl, ($C_2$-$C_{20}$)-alkynyl, ($C_1$-$C_{20}$)-alkoxy, ($C_2$-$C_{20}$)-alkenyloxy, ($C_2$-$C_{20}$)-alkynyloxy, retinyloxy, ($C_1$-$C_{20}$)-alkoxy-($C_1$-$C_{12}$)-alkyl, ($C_1$-$C_{12}$)-alkoxy-($C_1$-$C_{12}$)-alkoxy, ($C_1$-$C_{12}$)-alkoxy-($C_1$-$C_8$)-alkoxy-($C_1$-$C_8$)-alkyl, ($C_6$-$C_{12}$)-aryloxy, ($C_7$-$C_{16}$)-aralkyloxy, ($C_6$-$C_{12}$)-aryloxy-($C_1$-$C_6$)-alkoxy, ($C_7$-$C_{16}$)-aralkoxy-($C_1$-$C_6$)-alkoxy, ($C_1$-$C_{16}$)-hydroxyalkyl, ($C_6$-$C_{16}$)-aryloxy-($C_1$-$C_8$)-alkyl, ($C_7$-$C_{16}$)-aralkoxy-($C_1$-$C_8$)-alkyl, ($C_6$-$C_{12}$)-aryloxy-($C_1$-$C_8$)-alkoxy-($C_1$-$C_6$)-alkyl, ($C_7$-$C_{12}$)-aralkyloxy-($C_1$-$C_8$)-alkoxy-($C_1$-$C_6$)-alkyl, ($C_2$-$C_{20}$)-alkenyloxy-($C_1$-$C_6$)-alkyl, ($C_2$-$C_{20}$)-alkynyloxy-($C_1$-$C_6$)-alkyl, retinyloxy-($C_1$-$C_6$)-alkyl, —O—[$CH_2$]$_x$$CfH_{(2f+1-g)}F_g$, —$OCF_2Cl$, —$OCF_2$—$CHFCl$, ($C_1$-$C_{20}$)-alkylcarbonyl, ($C_3$-$C_8$)-cycloalkylcarbonyl, ($C_6$-$C_{12}$)-arylcarbonyl, ($C_7$-$C_{16}$)-aralkylcarbonyl, cinnamoyl, ($C_2$-$C_{20}$)-alkenylcarbonyl, ($C_2$-$C_{20}$)-alkynylcarbonyl, ($C_1$-$C_{20}$)-alkoxycarbonyl, ($C_1$-$C_{12}$)-alkoxy-($C_1$-$C_{12}$)-alkoxycarbonyl, ($C_6$-$C_{12}$)-aryloxycarbonyl, ($C_7$-$C_{16}$)-aralkoxycarbonyl, ($C_3$-$C_8$)-cycloalkoxycarbonyl, ($C_2$-$C_{20}$)-alkenyloxycarbonyl, retinyloxycarbonyl, ($C_2$-$C_{20}$)-alkynyloxycarbonyl, ($C_6$-$C_{12}$)-aryloxy-($C_1$-$C_6$)-alkoxycarbonyl, ($C_7$-$C_{16}$)-aralkoxy-($C_1$-$C_6$)-alkoxycarbonyl, ($C_3$-$C_8$)-cycloalkyl-($C_1$-$C_6$)-alkoxycarbonyl, ($C_3$-$C_8$)-cycloalkoxy-($C_1$-$C_6$)-alkoxycarbonyl, ($C_1$-$C_{12}$)-alkylcarbonyloxy, ($C_3$-$C_8$)-cycloalkylcarbonyloxy, ($C_6$-$C_{12}$)-arylcarbonyloxy, ($C_7$-$C_{16}$)-aralkylcarbonyloxy, cinnamoyloxy, ($C_2$-$C_{12}$)-alkenylcarbonyloxy, ($C_2$-$C_{12}$)-alkynylcarbonyloxy, ($C_1$-$C_{12}$)-alkoxycarbonyloxy, ($C_1$-$C_2$)-alkoxy-($C_1$-$C_{12}$)-alkoxycarbonyloxy, ($C_6$-$C_{12}$)-aryloxycarbonyloxy, ($C_7$-$C_{16}$)-aralkyloxycarbonyloxy, ($C_3$-$C_8$)-cycloalkoxycarbonyloxy, ($C_2$-$C_{12}$)-alkenyloxycarbonyloxy, ($C_2$-$C_{12}$)-alkynyloxycarbonyloxy, carbamoyl, N—($C_1$-$C_{12}$)-alkylcarbamoyl, N,N-di-($C_1$-$C_{12}$)-alkylcarbamoyl, N—($C_3$-$C_8$)-cycloalkylcarbamoyl, N,N-dicyclo-($C_3$-$C_8$)-alkylcarbamoyl, N—($C_1$-$C_{10}$)-alkyl-N—($C_3$-$C_8$)-cycloalkylcarbamoyl, N—(($C_3$-$C_8$)-cycloalkyl-($C_1$-$C_6$)-alkyl)-carbamoyl, N—($C_1$-$C_6$)-alkyl-N—(($C_3$-$C_8$)-cycloalkyl-($C_1$-$C_6$)-alkyl)-carbamoyl, N-(+)-dehydroabietylcarbamoyl, N—($C_1$-$C_6$)-alkyl-N-(+)-dehydroabietylcarbamoyl, N—($C_6$-$C_{12}$)-arylcarbamoyl, N—($C_7$-$C_{16}$)-aralkylcarbamoyl, N—($C_1$-$C_{10}$)-alkyl-N—($C_6$-$C_{16}$)-arylcarbamoyl, N—($C_1$-$C_{10}$)-alkyl-N—($C_7$-$C_{16}$)-aralkylcarbamoyl, N—(($C_1$-$C_{18}$)-alkoxy-($C_1$-$C_{10}$)-alkyl)-carbamoyl, N—(($C_6$-$C_{16}$)-aryloxy-($C_1$-$C_{10}$)-alkyl)-carbamoyl, N—(($C_7$-$C_{16}$)-aralkyloxy-($C_1$-$C_{10}$)-alkyl)-carbamoyl, N—($C_1$-$C_{10}$)-alkyl-N—(($C_1$-$C_{10}$)-alkoxy-($C_1$-$C_{10}$)-alkyl)-carbamoyl, N—($C_1$-$C_{10}$)-alkyl-N—(($C_6$-$C_{12}$)-aryloxy-($C_1$-$C_{10}$)-alkyl)-carbamoyl, N—($C_1$-$C_{10}$)-alkyl-N—(($C_7$-$C_{16}$)-aralkyloxy-($C_1$-$C_{10}$)-alkyl)-carbamoyl; $CON(CH_2)_h$, in which a $CH_2$ group can be replaced by O, S, N—($C_1$-$C_8$)-alkylimino, N—($C_3$-$C_8$)-cycloalkylimino, N—($C_3$-$C_8$)-cycloalkyl-($C_1$-$C_4$)-alkylimino, N—($C_6$-$C_{12}$)-arylimino, N—($C_7$-$C_{16}$)-aralkylimino, N—($C_1$-$C_4$)-alkoxy-($C_1$-$C_6$)-alkylimino, and h is from 3 to 7; a carbamoyl radical of the formula R

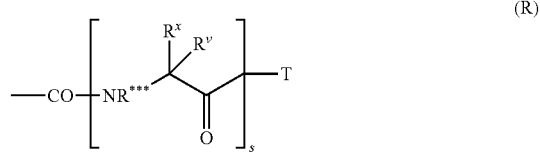

(R)

in which
$R^x$ and $R^v$ are each independently selected from hydrogen, ($C_1$-$C_6$)-alkyl, ($C_3$-$C_7$)-cycloalkyl, aryl, or the substituent of an α-carbon of an α-amino acid, to which the L- and D-amino acids belong, s is 1-5, T is OH, or NR*R**, and R*, R and R* are identical or different and are selected from hydrogen, ($C_6$-$C_{12}$)-aryl, ($C_7$-$C_{11}$)-aralkyl, ($C_1$-$C_8$)-alkyl, ($C_3$-$C_8$)-cycloalkyl, (+)-dehydroabietyl, ($C_1$-$C_8$)-alkoxy-($C_1$-$C_8$)-alkyl, ($C_7$-$C_{12}$)-aralkoxy-($C_1$-$C_8$)-alkyl, ($C_6$-$C_{12}$)-aryloxy-($C_1$-$C_8$)-alkyl, ($C_1$-$C_{10}$)-alkanoyl, optionally substituted ($C_7$-$C_{16}$)-aralkanoyl, optionally substituted ($C_6$-$C_{12}$)-aroyl; or R* and R** together are —[$CH_2$]$_h$, in which a $CH_2$ group can be replaced by O, S, SO, $SO_2$, N-acylamino, N—($C_1$-$C_{10}$)-alkoxycarbonylimino, N—($C_1$-$C_8$)-alkylimino, N—($C_3$-$C_8$)-cycloalkylimino, N—($C_3$-$C_8$)-cycloalkyl-($C_1$-$C_4$)-alkylimino, N—($C_6$-$C_{12}$)-arylimino, N—($C_7$-$C_{16}$)-aralkylimino, N—($C_1$-$C_4$)-alkoxy-($C_1$-$C_6$)-alkylimino, and h is from 3 to 7; carbamoyloxy, N—($C_1$-$C_{12}$)-alkylcarbamoyloxy, N,N-di-($C_1$-$C_{12}$)-alkylcarbamoyloxy, N—($C_3$-$C_8$)-cycloalkylcarbamoyloxy, N—($C_6$-$C_{12}$)-arylcarbamoyloxy, N—($C_7$-$c_{16}$)-aralkylcarbamoyloxy, N—($C_1$-$C_{10}$)-alkyl-N—($C_6$-$C_{12}$)-arylcarbamoyloxy, N—($C_1$-$C_{10}$)-alkyl-N—($C_7$-$C_{16}$)-aralkylcarbamoyloxy, N—(($C_1$-$C_{10}$)-alkyl)-carbamoyloxy, N—(($C_6$-$C_{12}$)-aryloxy-($C_1$-$C_{10}$)-alkyl)-carbamoyloxy, N—(($C_7$-$C_{16}$)-aralkyloxy-($C_1$-$C_{10}$)-alkyl)-carbamoyloxy, N—($C_1$-$C_{10}$)-alkyl-N—(($C_1$-$C_{10}$)-alkoxy-($C_1$-$C_{10}$)-alkyl)-carbamoyloxy, N—($C_1$-$C_{10}$)-alkyl-N—(($C_6$-$C_{12}$)-aryloxy-($C_1$-$C_{10}$)-alkyl)-carbamoyloxy, N—($C_1$-$C_{10}$)-alkyl-N—(($C_7$-$C_{16}$)-aralkyloxy-($C_1$-$C_{10}$)-alkyl)-carbamoyloxyamino, ($C_1$-$C_{12}$)-alkylamino, di-($C_1$-$C_{12}$)-alkylamino, ($C_3$-$C_8$)-cycloalkylamino, ($C_3$-$C_{12}$)-alkenylamino, ($C_3$-$C_{12}$)-alkynylamino, N—($C_6$-$C_{12}$)-arylamino, N—($C_7$-$C_{11}$)-aralkylamino, N-alkyl-aralkylamino, N-alkyl-arylamino, ($C_1$-$C_{12}$)-alkoxyamino, ($C_1$-$C_{12}$)-alkoxy-N—($C_1$-$C_{10}$)-alkylamino, ($C_1$-$C_{12}$)-alkanoylamino, ($C_3$-$C_8$)-cycloalkanoylamino, ($C_6$-$C_{12}$)-aroylamino, ($C_7$-$C_{16}$)-aralkanoylamino, ($C_1$-$C_{12}$)-alkanoyl-N—($C_1$-$C_{10}$)-alkylamino, ($C_3$-$C_8$)-cycloalkanoyl-N—($C_1$-$C_{10}$)-alkylamino, ($C_6$-$C_{12}$)-aroyl-N—($C_1$-$C_{10}$)-alkylamino, ($C_7$-$C_{11}$)-aralkanoyl-N—($C_1$-$C_{10}$)-alkylamino, ($C_1$-$C_{12}$)-alkanoylamino-($C_1$-$C_8$)-alkyl, ($C_3$-$C_8$)-cycloalkanoylamino-($C_1$-$C_8$)-alkyl, ($C_6$-$C_{12}$)-aroylamino-($C_1$-$C_8$)-alkyl, ($C_7$-$C_{16}$)-aralkanoylamino-($C_1$-$C_8$)-alkyl, amino-($C_1$-$C_{10}$)-alkyl, N—($C_1$-$C_{10}$)-alkylamino-($C_1$-$C_{10}$)-alkyl, N,N-di-($C_1$-$C_{10}$)-alkylamino-($C_1$-$C_{10}$)-alkyl, ($C_3$-$C_8$)-cycloalkylamino ($C_1$-$C_{10}$)-alkyl, ($C_1$-$C_{20}$)-alkylmercapto, ($C_1$-$C_{20}$)-alkylsulfinyl, ($C_1$-$C_{20}$)-alkylsulfonyl, ($C_6$-$C_{12}$)-arylmercapto, ($C_6$-$C_{12}$)-arylsulfinyl, ($C_6$-$C_{12}$)-arylsulfonyl, ($C_7$-$C_{16}$)-aralkylmercapto, ($C_7$-$C_{16}$)-aralkylsulfinyl, ($C_7$-$C_{16}$)-aralkylsulfonyl, ($C_1$-$C_{12}$)-alkylmercapto-($C_1$-$C_6$)-alkyl, ($C_1$-$C_{12}$)-alkylsulfinyl-($C_1$-$C_6$)-alkyl, ($C_1$-$C_{12}$)-alkylsulfonyl-($C_1$-$C_6$)-alkyl, ($C_6$-$C_{12}$)-arylmercapto-($C_1$-$C_6$)-alkyl, ($C_6$-$C_{12}$)-arylsulfinyl-($C_1$-$C_6$)-alkyl, ($C_6$-$C_{12}$)-arylsulfonyl-($C_1$-$C_6$)-alkyl, ($C_7$-$C_{16}$)-aralkylmercapto-($C_1$-$C_6$)-alkyl, ($C_7$-$C_{16}$)-aralkylsulfinyl-($C_1$-$C_6$)-alkyl, ($C_7$-$C_{16}$)-aralkylsulfonyl-($C_1$-$C_6$)-alkyl, sulfamoyl, N—($C_1$-$C_{10}$)-alkylsulfamoyl, N,N-di-($C_1$-$C_{10}$)-alkylsulfamoyl, ($C_3$-$C_8$)-cycloalkylsulfamoyl, N—($C_6$-$C_{12}$)-arylsulfamoyl, N—($C_7$-$C_{16}$)-aralkylsulfamoyl, N—($C_1$-$C_{10}$)-alkyl-N—($C_6$-$C_{12}$)-arylsulfamoyl, N—($C_1$-$C_{10}$)-alkyl-N—($C_7$-$C_{16}$)-aralkylsulfamoyl, ($C_1$-$C_{10}$)-alkylsulfonamido, N—(($C_1$-$C_{10}$)-alkyl)-($C_1$-$C_{10}$)-alkylsulfonamido, ($C_7$-$C_{16}$)-aralkylsulfonamido, and N—(($C_1$-$C_{10}$)-alkyl-($C_7$-$C_{16}$)-aralkylsulfonamido;

where an aryl radical may be substituted by 1 to 5 substituents selected from hydroxyl, halogen, cyano, trifluoromethyl, nitro, carboxyl, ($C_2$-$C_{16}$)-alkyl, ($C_3$-$C_8$)-cycloalkyl, ($C_3$-$C_8$)-cycloalkyl-($C_1$-$C_{12}$)-alkyl, ($C_3$-$C_8$)-cycloalkoxy, ($C_3$-$C_8$)-cycloalkyl-($C_1$-$C_{12}$)-alkoxy, ($C_3$-$C_8$)-cycloalkyloxy-($C_1$-$C_{12}$)-alkyl, ($C_3$-$C_8$)-cycloalkyloxy-($C_1$-$C_{12}$)-alkoxy, ($C_3$-$C_8$)-cycloalkyl-($C_1$-$C_8$)-alkyl-($C_1$-$C_6$)-alkoxy, ($C_3$-$C_8$)-cycloalkyl ($C_1$-$C_8$)-alkoxy-($C_1$-$C_6$)-alkyl, ($C_3$-$C_8$)-cycloalkyloxy-($C_1$-$C_8$)-alkoxy-($C_1$-$C_6$)-alkyl, ($C_3$-$C_8$)-cycloalkoxy-($C_1$-$C_8$)-alkoxy-($C_1$-$C_8$)-alkoxy, ($C_6$-$C_{12}$)-aryl, ($C_7$-$C_{16}$)-aralkyl, ($C_2$-$C_{16}$)-alkenyl, ($C_2$-$C_{12}$)-alkynyl, ($C_1$-$C_{16}$)-alkoxy, ($C_1$-$C_{16}$)-alkenyloxy, ($C_1$-$C_{12}$)-alkoxy-($C_1$-$C_{12}$)-alkyl, ($C_1$-$C_{12}$)-alkoxy-($C_1$-$C_{12}$)-alkoxy, ($C_1$-$C_{12}$)-alkoxy($C_1$-$C_8$)-alkoxy-($C_1$-$C_8$)-alkyl, ($C_6$-$C_{12}$)-aryloxy, ($C_7$-$C_{16}$)-aralkyloxy, ($C_6$-$C_{12}$)-aryloxy-($C_1$-$C_6$)-alkoxy, ($C_7$-$C_{16}$)-aralkoxy-($C_1$-$C_6$)-alkoxy, ($C_1$-$C_8$)-hydroxyalkyl, ($C_6$-$C_{16}$)-aryloxy-($C_1$-$C_8$)-alkyl, ($C_7$-$C_{16}$)-aralkoxy-($C_1$-$C_8$)-alkyl, ($C_6$-$C_{12}$)-aryloxy-($C_1$-$C_8$)-alkoxy-($C_1$-$C_6$)-alkyl, ($C_7$-$C_{12}$)-aralkyloxy-($C_1$-$C_8$)-alkoxy-($C_1$-$C_6$)-alkyl, —O—[$CH_2$]$_x$$C_f$$H_{(2f+1-g)}$$F_g$, —$OCF_2Cl$, —$OCF_2$—$CHFCl$, ($C_1$-$C_{12}$)-alkylcarbonyl, ($C_3$-$C_8$)-cycloalkylcarbonyl, ($C_6$-$C_{12}$)-arylcarbonyl, ($C_7$-$C_{16}$)-aralkylcarbonyl, ($C_1$-$C_{12}$)-alkoxycarbonyl, ($C_1$-$C_{12}$)-alkoxy-($C_1$-$C_{12}$)-alkoxycarbonyl, ($C_6$-$C_{12}$)-aryloxycarbonyl, ($C_7$-$C_{16}$)-aralkoxycarbonyl, ($C_3$-$C_8$)-cycloalkoxycarbonyl, ($C_2$-$C_{12}$)-alkenyloxycarbonyl, ($C_2$-$C_{12}$)-alkynyloxycarbonyl, ($C_6$-$C_{12}$)-aryloxy-($C_1$-$C_6$)-alkoxycarbonyl, ($C_7$-$C_{16}$)-aralkoxy-($C_1$-$C_6$)-alkoxycarbonyl, ($C_3$-$C_8$)-cycloalkyl-($C_1$-$C_6$)-alkoxycarbonyl, ($C_3$-$C_8$)-cycloalkoxy-($C_1$-$C_6$)-alkoxycarbonyl, ($C_1$-$C_{12}$)-alkylcarbonyloxy, ($C_3$-$C_8$)-cycloalkylcarbonyloxy, ($C_6$-$C_{12}$)-arylcarbonyloxy, ($C_7$-$C_{16}$)-aralkylcarbonyloxy, cinnamoyloxy, ($C_2$-$C_{12}$)-alkenylcarbonyloxy, ($C_2$-$C_{12}$)-alkynylcarbonyloxy, ($C_1$-$C_{12}$)-alkoxycarbonyloxy, ($C_1$-$C_{12}$)-alkoxy-($C_1$-$C_{12}$)-alkoxycarbonyloxy, ($C_6$-$C_{12}$)-aryloxycarbonyloxy, ($C_7$-$C_{16}$)-aralkyloxycarbonyloxy, ($C_3$-$C_8$)-cycloalkoxycarbonyloxy, ($C_2$-$C_{12}$)-alkenyloxycarbonyloxy, ($C_2$-$C_{12}$)-alkynyloxycarbonyloxy, carbamoyl, N—($C_1$-$C_{12}$)-alkylcarbamoyl, N,N-di($C_1$-$C_{12}$)-alkylcarbamoyl, N—($C_3$-$C_8$)-cycloalkylcarbamoyl, N,N-dicyclo-($C_3$-$C_8$)-alkylcarbamoyl, N—($C_1$-$C_{10}$)-alkyl-N—($C_3$-$C_8$)-cycloalkylcarbamoyl, N—(($C_3$-$C_8$)-cycloalkyl-($C_1$-$C_6$)-alkyl)carbamoyl, N—($C_1$-$C_6$)-alkyl-N—(($C_3$-$C_8$)-cycloalkyl-($C_1$-$C_6$)-alkyl)carbamoyl, N-(+)-dehydroabietylcarbamoyl, N—($C_1$-$C_6$)-alkyl-N-(+)-dehydroabietylcarbamoyl, N—($C_6$-$C_{12}$)-arylcarbamoyl, N—($C_7$-$C_{16}$)-aralkylcarbamoyl, N—($C_1$-$C_{10}$)-alkyl-N—($C_6$-$C_{16}$)-arylcarbamoyl, N—($C_1$-$C_{10}$)-alkyl-N—($C_7$-$C_{16}$)-aralkylcarbamoyl, N—(($C_1$-$C_{16}$)-alkoxy-($C_1$-$C_{10}$)-alkyl)carbamoyl, N—(($C_6$-$C_{16}$)-aryloxy-($C_1$-$C_{10}$)-alkyl)carbamoyl, N—(($C_7$-$C_{16}$)-aralkyloxy-($C_1$-$C_{10}$)-alkyl)carbamoyl, N—($C_1$-$C_{10}$)-alkyl-N—(($C_1$-$C_{10}$)-alkoxy-($C_1$-$C_{10}$)-alkyl)carbamoyl, N—($C_1$-$C_{10}$)-alkyl-N—(($C_6$-$C_{12}$)-aryloxy-($C_1$-$C_{10}$)-alkyl)carbamoyl, N—($C_1$-$C_{10}$)-alkyl-N—(($C_7$-$C_{16}$)-aralkyloxy-($C_1$-$C_{10}$)-alkyl)-carbamoyl, CON($CH_2$)$_h$, in which a $CH_2$ group can be replaced by, O, S, N—($C_1$-$C_8$)-alkylimino, N—($C_3$-$C_8$)-cycloalkylimino, N—($C_3$-$C_8$)-cycloalkyl-($C_1$-$C_4$)-alkylimino, N—($C_6$-$C_{12}$)-arylimino, N—($C_7$-$C_{16}$)-aralkylimino, N—($C_1$-$C_4$)-alkoxy-($C_1$-$C_6$)-alkylimino, and h is from 3 to 7; carbamoyloxy, N—($C_1$-$C_{12}$)-alkylcarbamoyloxy, N,N-di-($C_1$-$C_{12}$)-alkylcarbamoyloxy, N—($C_3$-

$C_8$)-cycloalkylcarbamoyloxy, N—($C_6$-$C_{16}$)-arylcarbamoyloxy, N—($C_7$-$C_{16}$)-aralkylcarbamoyloxy, N—($C_1$-$C_{10}$)-alkyl-N—($C_6$-$C_{12}$)-arylcarbamoyloxy, N—($C_1$-$C_{10}$)-alkyl-N—($C_7$-$C_{16}$)-aralkylcarbamoyloxy, N—(($C_1$-$C_{10}$)-alkyl)carbamoyloxy, N—(($C_6$-$C_{12}$)-aryloxy-($C_1$-$C_{10}$)-alkyl)carbamoyloxy, N—(($C_7$-$C_{16}$)-aralkyloxy-($C_1$-$C_{10}$)-alkyl)carbamoyloxy, N—($C_1$-$C_{10}$)-alkyl-N—(($C_1$-$C_{10}$)-alkoxy-($C_1$-$C_{10}$)-alkyl)carbamoyloxy, N—($C_1$-$C_{10}$)-alkyl-N—(($C_6$-$C_{12}$)-aryloxy-($C_1$-$C_{10}$)-alkyl)carbamoyloxy, N—($C_1$-$C_{10}$)-alkyl-N—(($C_7$-$C_{16}$)-aralkyloxy-($C_1$-$C_{10}$)-alkyl)carbamoyloxy, amino, ($C_1$-$C_{12}$)-alkylamino, di-($C_1$-$C_{12}$)-alkylamino, ($C_3$-$C_8$)-cycloalkylamino, ($C_3$-$C_{12}$)-alkenylamino, ($C_3$-$C_{12}$)-alkynylamino, N—($C_6$-$C_{12}$)-arylamino, N—($C_7$-$C_{11}$)-aralkylamino, N-alkyl-aralkylamino, N-alkyl-arylamino, ($C_1$-$C_{12}$)-alkoxyamino, ($C_1$-$C_{12}$)-alkoxy-N—($C_1$-$C_{10}$)-alkylamino, ($C_1$-$C_{12}$)-alkanoylamino, ($C_3$-$C_8$)-cycloalkanoylamino, ($C_6$-$C_{12}$)-aroylamino, ($C_7$-$C_{16}$)-aralkanoylamino, ($C_1$-$C_{12}$)-alkanoyl-N—($C_1$-$C_{10}$)-alkylamino, ($C_3$-$C_8$)-cycloalkanoyl-N—($C_1$-$C_{10}$)-alkylamino, ($C_6$-$C_{12}$)-aroyl-N—($C_1$-$C_{10}$)-alkylamino, ($C_7$-$C_{11}$)-aralkanoyl-N—($C_1$-$C_{10}$)-alkylamino, ($C_1$-$C_{12}$)-alkanoylamino-($C_1$-$C_8$)-alkyl, ($C_3$-$C_8$)-cycloalkanoylamino-($C_1$-$C_8$)-alkyl, ($C_6$-$C_{12}$)-aroylamino-($C_1$-$C_8$)-alkyl, ($C_7$-$C_{16}$)-aralkanoylamino-($C_1$-$C_8$)-alkyl, amino-($C_1$-$C_{10}$)-alkyl, N—($C_1$-$C_{10}$)-alkylamino-($C_1$-$C_{10}$)-alkyl, N,N-di-($C_1$-$C_{10}$)-alkylamino-($C_1$-$C_{10}$)-alkyl, ($C_3$-$C_8$)-cycloalkylamino-($C_1$-$C_{10}$)-alkyl, ($C_1$-$C_{12}$)-alkylmercapto, ($C_1$-$C_{12}$)-alkylsulfinyl, ($C_1$-$C_{12}$)-alkylsulfonyl, ($C_6$-$C_{16}$)-arylmercapto, ($C_6$-$C_{16}$)-arylsulfinyl, ($C_6$-$C_{16}$)-arylsulfonyl, ($C_7$-$C_{16}$)-aralkylmercapto, ($C_7$-$C_{16}$)-aralkylsulfinyl, or ($C_7$-$C_{16}$)-aralkylsulfonyl;

including the physiologically active salts derived therefrom.

2. The method of claim 1, wherein the compound inhibits hypoxia-inducible factor (HIF) prolyl hydroxylase enzyme activity.

3. A method of treating anemia in a human subject comprising administering to the human subject an effective amount of a compound, wherein the human subject has a transferrin saturation (TSAT) level below 20% prior to said administering and wherein the compound is a compound of Formula I $$\text{(I)}$$

wherein
A is —$CR^5R^6$ and $R^5$ and $R^6$ are each hydrogen;
B is —$CO_2H$;
X is O;
Q is O;
Y is $CR^3$
$R^1$, $R^2$ and $R^3$ are identical or different and are hydrogen, halogen, ($C_1$-$C_{20}$)-alkyl, ($C_6$-$C_{12}$)-aryl, ($C_1$-$C_{20}$)-alkoxy, ($C_6$-$C_{12}$)-aryloxy, N—(($C_1$-$C_{18}$)-alkoxy-($C_1$-$C_{10}$)-alkyl)-carbamoyl, ($C_6$-$C_{12}$)-arylmercapto; where an aryl radical may be substituted by 1 to 5 substituents selected from halogen;

including the physiologically active salts derived therefrom.

4. The method of claim 3, wherein the compound inhibits hypoxia-inducible factor (HIF) prolyl hydroxylase enzyme activity.

5. The method of claim 1, wherein the compound is orally administered to the human subject.

6. The method of claim 1, wherein the erythropoietin plasma level in the human subject is increased following administration of the effective amount of the compound.

7. The method of claim 1, wherein the iron level in the human subject is increased following administration of the effective amount of the compounds.

8. The method of claim 1, wherein the human subject has a transferrin saturation level below 16%, below 15%, or below 10%.

9. The method of claim 1, wherein the method increases the transferrin saturation level in the subject to a level above 20%, above 30%, above 40%, or above 50%.

10. The method of claim 1, wherein the anemia does not respond to treatment with exogenously administered erythropoietin.

11. The method of claim 1, wherein the percent transferrin saturation in the human subject is increased to a value between 25% to 50% following administration of the effective amount of the compound.

12. The method of claim 1, wherein the hemoglobin level in the human subject is increased following administration of the effective amount of the compound.

13. The method of claim 1, wherein the human subject is a subject having iron deficiency.

14. The method of claim 13, wherein the human subject is a subject having a functional iron deficiency.

15. The method of claim 3, wherein the compound is orally administered to the human subject.

16. The method of claim 3, wherein the erythropoietin plasma level in the human subject is increased following administration of the effective amount of the compound.

17. The method of claim 3, wherein the iron level in the human subject is increased following administration of the effective amount of the compounds.

18. The method of claim 3, wherein the human subject has a transferrin saturation level below 16%, below 15%, or below 10%.

19. The method of claim 3, wherein the method increases the transferrin saturation level in the human subject to a level above 20%, above 30%, above 40%, or above 50%.

20. The method of claim 3, wherein the anemia does not respond to treatment with exogenously administered erythropoietin.

21. The method of claim 3, wherein the percent transferrin saturation in the human subject is increased to a value between 25% to 50% following administration of the effective amount of the compound.

22. The method of claim 3, wherein the hemoglobin level in the human subject is increased following administration of the effective amount of the compound.

23. The method of claim 3, wherein the human subject is a subject having iron deficiency.

24. The method of claim 23, wherein the human subject is a subject having a functional iron deficiency.

* * * * *